(12) United States Patent
Li et al.

(10) Patent No.: US 8,921,370 B2
(45) Date of Patent: Dec. 30, 2014

(54) BICYCLO[3.2.1]OCTYL AMIDE DERIVATIVES AND USES OF SAME

(75) Inventors: Guiying Li, River Edge, NJ (US); Hao Zhou, Paramus, NJ (US); Jesse Weiss, Woodbridge, NJ (US); Dario Doller, Sparta, NJ (US); James Ford Burns, Glen Ridge, NJ (US)

(73) Assignee: H. Lundbeck A/S, Valby (DK)

( * ) Notice: Subject to any disclaimer, the term of this patent is extended or adjusted under 35 U.S.C. 154(b) by 171 days.

(21) Appl. No.: 13/334,129

(22) Filed: Dec. 22, 2011
(Under 37 CFR 1.47)

(65) Prior Publication Data

US 2012/0190686 A1 Jul. 26, 2012

Related U.S. Application Data

(60) Provisional application No. 61/426,379, filed on Dec. 22, 2010.

(51) Int. Cl.
| | | |
|---|---|---|
| *A61K 31/497* | (2006.01) | |
| *A61K 31/44* | (2006.01) | |
| *A61K 31/4965* | (2006.01) | |
| *A61K 31/425* | (2006.01) | |
| *C07D 401/04* | (2006.01) | |
| *C07D 241/24* | (2006.01) | |
| *C07D 239/28* | (2006.01) | |
| *C07D 417/12* | (2006.01) | |
| *C07D 403/12* | (2006.01) | |
| *C07D 213/81* | (2006.01) | |
| *C07D 401/12* | (2006.01) | |
| *C07D 241/20* | (2006.01) | |
| *C07D 277/56* | (2006.01) | |
| *C07D 213/75* | (2006.01) | |
| *C07D 239/42* | (2006.01) | |

(52) U.S. Cl.
CPC ............ *C07D 241/20* (2013.01); *C07D 401/12* (2013.01); *C07D 403/12* (2013.01); *C07D 277/56* (2013.01); *C07D 213/75* (2013.01); *C07D 239/42* (2013.01); *C07D 239/28* (2013.01); *C07D 213/81* (2013.01); *C07D 241/24* (2013.01); *C07D 417/12* (2013.01)
USPC . 514/252.11; 514/332; 514/354; 514/255.05; 514/255.06; 514/256; 514/342; 514/365; 544/405; 544/357; 544/295; 544/333; 544/335; 544/406; 546/262; 546/269.7; 546/323; 548/200

(58) Field of Classification Search
CPC . A61K 31/497; A61K 31/44; A61K 31/4695; A61K 31/425; A61K 31/444; A61K 31/506; A61K 31/426; A61K 31/4439; C07D 401/04; C07D 401/12; C07D 214/02; C07D 241/24; C07D 403/02; C07D 403/12; C07D 213/81; C07D 239/28; C07D 277/56; C07D 417/12
USPC ............... 514/252.11, 354, 332, 255.06, 256, 514/365, 342, 255.05; 544/335, 357, 295, 544/406, 333, 405; 546/262, 323, 269.7; 548/200

See application file for complete search history.

(56) References Cited

U.S. PATENT DOCUMENTS 6,143,783 A 11/2000 Monn et al.

FOREIGN PATENT DOCUMENTS

| EP | 2080757 A1 | 7/2009 |
|---|---|---|
| WO | 01/16121 A1 | 3/2001 |
| WO | 2010/011570 A1 | 1/2010 |

OTHER PUBLICATIONS

International Search Report and Written Opinion issued May 2, 2012 in International Application No. PCT/US2011/66690 filed Dec. 22, 2011.
Examination and Search Report issued Jul. 4, 2014 in Singapore Application No. 201304055.8 filed Dec. 22, 2011.

*Primary Examiner* — Kamal Saeed
*Assistant Examiner* — Ebenezer O Sackey
(74) *Attorney, Agent, or Firm* — Mary Catherine Di Nunzio

(57) ABSTRACT

The present invention provides bicyclo[3.2.1]octyl amide derivatives of formula (I):

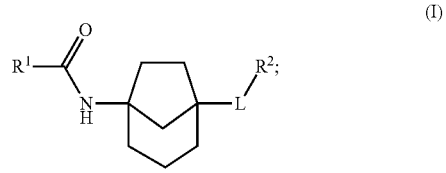

wherein L, $R^1$ and $R^2$ are as defined herein, or a pharmaceutically acceptable salt thereof; and pharmaceutical compositions and methods using the same.

16 Claims, No Drawings

BICYCLO[3.2.1]OCTYL AMIDE DERIVATIVES AND USES OF SAME

FIELD OF THE INVENTION

The present invention provides bicyclo[3.2.1]octyl amide derivatives, as well as pharmaceutical compositions and methods of treatment using same.

BACKGROUND OF THE INVENTION

This invention concerns bicyclo[3.2.1]octyl amide derivatives, which act as allosteric modulators of the metabotropic glutamate receptor 5 (mGlu5 receptors or mGluR5), as well as pharmaceutical compositions and methods of treatment utilizing these compounds.

Glutamate is the major excitatory neurotransmitter in the mammalian central nervous system. One means of modulating glutamate neurotransmission is through metabotropic glutamate receptors (mGluRs); another means being ionotropic receptors. Presently, eight mGluRs have been cloned and classified into three groups based on sequence homology, preferred signal transduction pathway and pharmacology. Group I of mGluRs includes mGluR1 and mGluR5, while Group II comprises mGluR2 and mGluR3 and Group III comprises mGlu4, 6, 7 and 8 receptors.

mGlu receptors have an essential role in normal brain functions, as well as in neurological, psychiatric, and neuromuscular disorders. mGlu5 receptors are located primarily postsynaptically and highly expressed in the limbic brain regions. mGlu5 receptors also are expressed in the thalamus, spinal cord, and vagal nerve systems, as well as peripherally in the skin on nerve endings and C fibers.

Ligands to the mGlu5 receptors have been shown to have promise for peripheral and central nervous system disorders. See e.g., G. Jaeschke et al., "mGlu5 receptor antagonists and their therapeutic potential," *Expert Opin. Ther. Patents*, 2008, 18, 2: 123-142. Yet some proffer that glutamate analogs targeting the orthosteric binding site may be limited by low brain penetration and insufficient selectivity with respect to the different mGluRs subtypes. Synthetic agonists may lead to continuous stimulation of the receptor since they are often designed to be metabolically stable. This continuous stimulation is not necessarily desirable, due to potential receptor desensitization issues. Also, with respect to receptor occupancy, synthetic antagonists may lead to prolonged blockade of receptor function, which may not be compatible with the kinetics of the pathology of a central nervous system disorder.

However, a more selective and controlled "fine-tuning" action on the mGlu5 receptor is feasible through allosteric modulation. See e.g., P. Bach et al., "Metabotropic glutamate receptor 5 modulators and their potential therapeutic applications," *Expert Opin. Ther. Patents*, 2007, 17, 4: 371-381. Allosteric modulation refers to binding by a modulator ligand to a site on a receptor that is different from the orthosteric primary substrate or ligand binding site. This ligand binding process results in conformational changes, which may profoundly influence the function of the protein (e.g., G protein-coupled receptors such as mGluRs, including mGluR5). Novel mGluR5 ligands that allosterically modulate the mGlu5 receptor may improve the therapeutic window of traditional central nervous system agents and/or the treatment of central nervous system disorders. The present invention is directed these, and other important, ends.

SUMMARY OF THE INVENTION

The present invention provides a compound of formula (I):

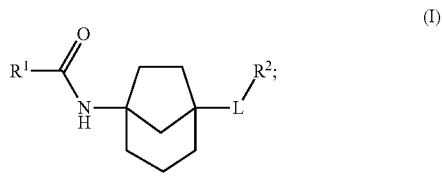

wherein:
L is —NHCO— or —CONH—; and
$R^1$ and $R^2$ are each independently alkyl, cycloalkyl, ketocycloalkyl, heterocyclyl, aryl or heteroaryl, which is optionally mono-, di-, or tri-substituted independently with alkyl, alkoxy, halogen, cyano, nitro, trifluoroalkyl, amino, alkylamino, dialkylamino, acyl, aryl, heteroaryl, heterocyclyl, heterocyclyl-$R^3$, —$NHR^3$, —$N(alkyl)R^3$, —$C(O)NHR^3$, —$C(O)N(alkyl)R^3$, —$NHC(O)R^3$, —$N(alkyl)C(O)R^3$, —OH or —$OR^3$, wherein:
$R^3$ is $C_1$-$C_6$alkyl or $C_1$-$C_6$cycloalkyl, which is optionally substituted with halogen, —CN, —$NH_2$, —$NH(C_1$-$C_3$alkyl), —$N(C_1$-$C_3$alkyl)$_2$, $C_1$-$C_3$alkylheterocyclyl, $C_1$-$C_3$alkylcarbamate, —$C(O)NH(C_1$-$C_3$alkyl), —$C(O)N(C_1$-$C_3$alkyl)$_2$, —NHC(O)—$C_1$-$C_3$alkyl, —$N(C_1$-$C_3$alkyl)-C(O)—$C_1$-$C_3$alkyl, OH, or —O—$C_1$-$C_6$alkyl; or a pharmaceutically acceptable salt thereof.

The present invention also provides a pharmaceutical composition comprising at least one compound of the invention or a pharmaceutically acceptable salt thereof, and at least one pharmaceutically acceptable carrier.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder. In some embodiments of the method, a symptom of the disease or disorder is treated.

DETAILED DESCRIPTION OF THE INVENTION

In one aspect, the present invention provides bicyclo[3.2.1] octyl amide derivatives. The present invention comprises a compound of formula (I-A) or (I-B):

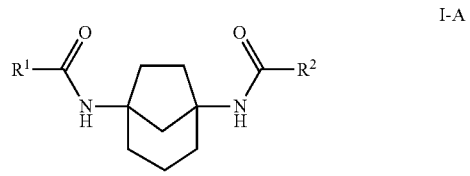

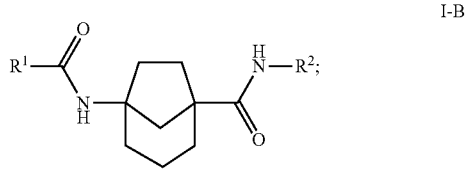

wherein:
   R$^1$ and R$^2$ are each independently alkyl, cycloalkyl, ketocycloalkyl, heterocyclyl, aryl or heteroaryl, which is optionally mono-, di-, or tri-substituting independently with alkyl, alkoxy, halogen, cyano, nitro, trifluoroalkyl, amino, alkylamino, dialkylamino, acyl, aryl, heteroaryl, heterocyclyl, heterocyclyl-R$^3$, —NHR$^3$, —N(alkyl)R$^3$, —C(O)NHR$^3$, —C(O)N(alkyl)R$^3$, —NHC(O)R$^3$, —N(alkyl)C(O)R$^3$, —OH or —OR$^3$, wherein:
      R$^3$ is C$_1$-C$_6$alkyl or C$_1$-C$_6$cycloalkyl, which is optionally substituted with halogen, —CN, —NH(C$_1$-C$_3$alkyl), —N(C$_1$-C$_3$alkyl)$_2$, C$_1$-C$_3$alkylheterocyclyl, C$_1$-C$_3$alkylcarbamate, —C(O)NH(C$_1$-C$_3$alkyl), —C(O)N(C$_1$-C$_3$alkyl)$_2$, —NHC(O)—C$_1$-C$_3$alkyl, —N(C$_1$-C$_3$alkyl)-C(O)—C$_1$-C$_3$alkyl, OH, or —O—C$_1$-C$_6$alkyl; or
a pharmaceutically acceptable salt thereof.

The term "alkyl", employed alone or as part of a group, is defined herein, unless otherwise stated, as either a straight-chain or branched saturated hydrocarbon of 1 to 8 carbon atoms. In some embodiments, the alkyl moiety contains 8, 7, 6, 5, 4, 3, 2 or 1 carbon atoms. Where the term "alkyl" appears herein without a carbon atom range it means a range of C$_1$-C$_8$. Examples of saturated hydrocarbon alkyl moieties include, but are not limited to, chemical groups such as methyl, ethyl, n-propyl, isopropyl, n-butyl, tert-butyl, iso-butyl, sec-butyl, n-pentyl, n-hexyl, and the like.

The term "alkoxy", employed alone or in combination with other terms, is defined herein, unless otherwise stated, as —O-alkyl, where "alkyl" is as previously defined herein. Examples of alkoxy moieties include, but are not limited to, chemical groups such as methoxy, ethoxy, iso-propoxy, sec-butoxy, tert-butoxy, and homologs, isomers, and the like. Alkoxy also refers to —O-alkyl moieties where the alkyl group is substituted by hydroxy, cyano, alkoxy, alkylamino, dialkylamino, alkylamide, dialkylamide, and the like, including without limitation, —OC$_1$-C$_4$alkyl-OH, —OC$_1$-C$_4$alkyl-OCH$_3$, —OC$_1$-C$_4$alkyl-NHCH$_3$, —OC$_1$-C$_4$alkyl-N(CH$_3$)$_2$, —OC$_1$-C$_4$alkyl-CONHCH$_3$, —OC$_1$-C$_4$alkyl-CON(CH$_3$)$_2$, —OC$_1$-C$_4$alkyl-NHCOCH$_3$, and —OC$_1$-C$_4$alkyl-N(CH$_3$)COCH$_3$.

As used herein, the term "cycloalkyl", employed alone or in combination with other terms, is defined herein, unless otherwise stated, as a cyclized alkyl group having from 3 to 8 ring carbon atoms, where "alkyl" is as defined herein. Examples of cycloalkyl moieties include, but are not limited to, chemical groups such as cyclopropyl, cyclobutyl, cyclopentyl, and cyclohexyl.

As used herein, the term "ketocycloalkyl", employed alone or in combination with other terms, is defined herein, unless otherwise stated, as a cycloalkyl having a keto radical attached thereto, where "cycloalkyl" is as defined herein. Examples include cyclopentanone or cyclohexanone.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (e.g., bicyclic, tricyclic, polycyclic) fused together or linked covalently. Any suitable ring position of the aryl moiety can be covalently linked to the defined chemical structure. Examples of aryl moieties include, but are not limited to, chemical groups such as phenyl, benzyl, 1-naphthyl, 2-naphthyl, and the like. An aryl group can be unsubstituted or substituted as described herein.

The term "heteroaryl" employed alone or in combination with other terms, is defined herein, unless otherwise stated, as a monocyclic or polycyclic (fused together or linked covalently) aromatic hydrocarbon ring comprising one or more heteroatoms independently selected from nitrogen, oxygen, and sulfur. A heteroaryl group comprises up to 14 carbon atoms and 1 to 6 heteroatoms. Examples of heteroaryl groups include, but are not limited to, pyridinyl, pyridazinyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, oxazolyl, 2-quinolinyl, 2-quinazolinyl, 3-phenyl-2-quinolinyl and the like. A heteroaryl group can be unsubstituted or substituted as described herein.

The term "heterocyclyl" employed alone or in combination with other terms, is defined herein, unless otherwise stated, as a univalent group formed by removing a hydrogen atom from any ring atom of a heterocycle.

The term "acyl" employed alone or in combination with other terms, is defined herein, unless otherwise stated, as groups of formula —C(O)-alkyl, where alkyl is a previously described herein; i.e., an alkylcarbonyl, such as formyl, acetyl and the like.

The term "aminoalkyl" employed alone or in combination with other terms, is defined herein, unless otherwise stated, as alkyl-amino, where the term "alkyl" is as previously defined herein and the term "amino" is —NH$_2$, —NH—, or —N<. Non-limiting examples include —CH$_3$NH— and CH$_3$CH$_2$NH—.

The term "alkylamino" employed alone or in combination with other terms, is defined herein, unless otherwise stated, as amino-alkyl, where the term "alkyl" is as previously defined herein and the term "amino" is —NH$_2$, —NH—, or —N<. Non-limiting examples include —NHCH$_3$ and —NHCH$_2$CH$_3$.

In some embodiments of the invention, R$^1$ and R$^2$ are both aryl. In some embodiments, R$^1$ and R$^2$ are both heteroaryl. In some embodiments, R$^1$ is aryl and R$^2$ is heteroaryl. In some embodiments, either R$^1$ or R$^2$ is heteroaryl. In some embodiments, either R$^1$ or R$^2$ is aryl.

In some embodiments of the invention, at least one aryl is phenyl. In some embodiments, at least one heteroaryl is benzofuranyl, benzo[c]isoxazolyl, benzooxazolyl, benzothiazolyl, dihydrothieno[3,4-b][1,4]dioxinyl, furanyl, imidazo[1,2-a]pyridinyl, indazolyl, indolinyl, indolyl, isoquinolinyl, isoxazolyl, naphthyridinyl, oxazolyl, pyrazinyl, pyrazolyl, pyridazinyl, pyridinyl, pyrimidinyl, pyrrolo[3,2-c]pyridine, quinolinyl, quinoxalinyl, thiazolyl, or thiophenyl.

In some embodiments, both aryls are phenyl. In some embodiments, both heteroaryls are selected from a group consisting of at least one heteroaryl is benzofuranyl, benzo[c]isoxazolyl, benzoxazolyl, benzothiazolyl, dihydrothieno[3,4-b][1,4]dioxinyl, furanyl, imidazo[1,2-a]pyridinyl, indazolyl, indolinyl, indolyl, isoquinolinyl, isoxazolyl, naphthyridinyl, oxazolyl, pyrazinyl, pyrazolyl, pyridazinyl, pyridinyl, pyrimidinyl, pyrrolo[3,2-c]pyridinyl, quinolinyl, quinoxalinyl, thiazolyl, or thiophenyl.

In some embodiments, the heteroaryl is pyridinyl, and the pyridinyl is mono-, di-, or tri-substituted as previously defined. In some such embodiments, the mono-, di-, or tri-substitutions are independently heteroaryl, heterocyclyl, heterocyclyl-R$^3$, —N(alkyl)R$^3$, wherein R$^3$ is as previously defined.

In some embodiments of the invention, R$^1$ is aryl or heteroaryl and R$^2$ is cycloalkyl, ketocycloalkyl or heterocyclyl. In some embodiments, either R$^1$ or R$^2$ is cycloalkyl. In some embodiments, at least one cycloalkyl is cyclobutyl, cyclohexyl, cyclopentyl, or cyclopropyl. In some embodiments, the cycloalkyl is further substituted beyond the tri-substitution previously defined, i.e., the cycloalkyl is substituted more than three times as previously described; for example, the cycloalkyl is tetra-substituted with fluorine.

In some embodiments of the invention, at least one cycloalkyl, ketocycloalkyl, heterocyclyl, aryl, or heteroaryl is substituted as previously described. In some such embodiments, the 1, 2, or 3 substituents are independently selected from the group consisting of methyl, methoxy, dimethylamino-ethoxy, amino, methylamino, dimethylamino, cyano, chloro, fluoro, furanyl and thiophenyl.

In some embodiments, the mono-, di-, or tri-substituents are independently selected from the group consisting of amino, chloro, cyano, dimethylamino, dimethylaminoethoxy, methyl, methylamino, methoxy, fluoro, —C(O)NHCH$_3$, furanyl, pyrrolidinyl, thiophenyl and trifluoromethyl.

In some embodiments, the compound of the present invention is a compound disclosed in the Experimental Section below. In some embodiments, the compound is one from Table 1 or Table 2, below.

Another aspect of the present invention is a composition that comprises a pharmaceutically effective amount of a compound according to the present invention, and a pharmaceutically acceptable carrier or excipient.

A composition of the present invention may be adapted to any mode of administration, such as orally (including sublingually), via implants, parentally (including intravenous, intraperitoneal, intraarticularly and subcutaneous injections), rectally, intranasally, topically, ocularly (via eye drops), vaginally, and transdermally.

A compound of the present invention can be used either as a free base or in the form of a salt derived from pharmaceutically acceptable acids or bases. The salt includes without limitation the following: salts with inorganic acids, e.g., hydrochloric acid, hydrobromic acid, sulfuric acid, nitric acid, and phosphoric acid, and organic acids e.g., acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium and magnesium, or with organic bases, including quaternary ammonium salts. Further non-limiting examples of pharmaceutically acceptable inorganic and organic acid addition salts include those listed in [S. M. Berge et al., *J. Sci.* 1977, 66, 1: 2, and G. S. Paulekuhn, et al., *J. Med. Chem.* 2007, 50, 26: 6665-6672].

A compound of the present invention can also be used in the form of an ester, carbamate and other conventional prodrug form, which generally will be a functional derivative of the compound that is readily converted to the active moiety in vivo. Also included are metabolites of a compound of the present invention defined as active species produced upon introduction of the compound into a biological system.

When a compound of the present invention is employed as described above, it may be combined with one or more pharmaceutically acceptable excipients or carriers, e.g., solvents, diluents and the like. Such pharmaceutical preparations may be administered orally in such forms as tablets, capsules (including, e.g., time release and sustained release formulations), pills, lozenges, aerosols, dispersible powders, granules, solutions, suspensions (containing, e.g., a suspending agent, at, e.g., from about 0.05 to about 5% of suspending agent), syrups (containing, e.g., sugar or a sugar substitute such as aspartame, at, e.g., about 10 to about 50% sugar or sugar substitute), elixirs and the like, or parenterally in the form of sterile injectable solutions, suspensions or emulsions containing, e.g., from about 0.05 to about 5% suspending agent in an isotonic medium. Such preparations may contain, e.g., from about 25 to about 90% of the active ingredient in combination with the carrier, more customarily from about 5% and about 60% by weight. The effective dosage of an active ingredient (e.g., a compound or salt of the present invention and a prodrug or metabolite thereof) employed may vary depending on the particular compound, salt, prodrug or metabolite used, the mode of administration, age, weight, sex and medical condition of the patient, and the severity of the disease, disorder, condition, and/or system being treated. The selection of the appropriate administration and dosage form for an individual mammal will be apparent to those skilled in the art. Such determinations are routine to a physician, veterinarian or clinician of ordinary skill in the art (see e.g., *Harrison's Principles of Internal Medicine*, Anthony Fauci et al. (eds.) 14$^{th}$ ed. New York: McGraw Hill (1998)). Further, the dosage regimen may be adjusted to provide the optimal therapeutic response. For example, several divided doses may be administered daily or the dose may be proportionally reduced as indicated by the needs of the therapeutic situation.

Solid carriers, e.g., starch, lactose, dicalcium phosphate, microcrystalline cellulose, sucrose and kaolin, liquid carriers, e.g., sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Non-limiting examples of adjuvants include flavoring agents, coloring agents, preserving agents, and antioxidants, such as vitamin E, ascorbic acid, BHT and BHA.

An active compound also may be administered parenterally or intraperitoneally. Solutions or suspensions of the active compound as a free base, neutral compound or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations may contain a preservative to prevent the growth of microorganisms under ordinary conditions of storage and use.

The pharmaceutical forms suitable for injectable or infusing use include sterile aqueous solutions, suspensions or dispersions, and sterile powders for the extemporaneous preparation of sterile injectable or infusing solutions, suspension or dispersions. In all cases, the form must be sterile and must be fluid to the extent that easy injectability and infusing exists. It must be stable under conditions of manufacture and storage and must be preserved against the contaminating action of microorganisms. The carrier can be a solvent or dispersion medium containing, for example, water, ethanol, and polyol (e.g., glycerol, propylene glycol, and liquid polyethylene glycol), suitable mixtures thereof, and vegetable oil.

Furthermore, active compounds of the present invention can be administered intranasally or transdermally using vehicles suitable for intranasal or transdermal delivery known to those ordinarily skilled in the art. Transdermal administration includes all administrations across the surface of the body and the inner linings of bodily passages including epithelial and mucosal tissues, using carrier systems such as lotions, creams, foams, pastes, patches, suspensions, solutions, and suppositories (rectal and vaginal). Creams and ointments may be viscous liquid or semisolid emulsions of either the oil-in-water or water-in-oil type. Pastes comprised of absorptive powders dispersed in petroleum or hydrophilic petroleum containing the active ingredient also may be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature. When using a transdermal delivery system, the dosage administration will be continuous rather than a single or divided daily dose.

A compound of the present invention can also be administered in the form of a liposome delivery system where the liposomal lipid bilayer is formed from a variety of phospholipids. A compound of the present invention also may be delivered by the use of a carrier such as monoclonal antibodies to which the compound is coupled. Other carriers to which a compound of the present invention also may be coupled are a soluble polymer or a biodegradable polymer useful in achieving controlled release of an active ingredient.

It is understood by those practicing the art that some of the compounds of the present invention may contain one or more asymmetric centers, and thus may give rise to enantiomers and diastereomers. The present invention includes all stereoisomers including individual diastereomers and resolved, enantiomerically pure stereoisomers, as well as racemates, and all other variations of stereoisomers, and mixtures and pharmaceutically acceptable salts thereof, which possess the indicated activity. Optical isomers may be obtained in pure form by customary procedures known to those skilled in the art, and include, but are not limited to, chiral chromatographic separations, diastereomeric salt formation, kinetic resolution, and asymmetric synthesis. It is also understood that this invention encompasses all possible regioisomers, endo-exo isomers, and mixtures thereof that possess the indicated activity. Such isomers can be obtained in pure form by customary procedures known to those skilled in the art, and include, but are not limited to, column chromatography, thin-layer chromatography, and high-performance liquid chromatography. It is understood by those practicing the art that some of the compounds of the present invention may be chiral due to hindered rotation, and give rise to atropisomers, which can be resolved and obtained in pure form by customary procedures known to those skilled in the art. It is further understood by those practicing the art that some of the compounds of the present invention include structural isomers, including tautomers.

Included also in this invention are all polymorphs and hydrates of the compounds of the present invention.

Another aspect of the present invention is a use or a method for using the compounds of the invention. The invention is to be understood as embracing all simultaneous, sequential or separate use of any combination of the compounds of the invention with any pharmaceutical composition useful in the methods described herein.

In some embodiments, the use or method includes administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt, neutral or free base forms; i.e., includes the administration of such compounds each in the base form, each in the neutral form or each in the salt form, or one or more in the base form and one or more in the neutral form, or one or more in the base form and one or more in the salt form, or one or more in the neutral form and one or more in the salt form, in any proportion of the neutral and/or basic compounds and/or salts.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In some embodiments, the method of the present invention provides for administration of combinations of compounds. In such instances, the "effective amount" is the amount of the combination sufficient to cause the intended biological effect.

The term "treatment" or "treating" as used herein means curing, ameliorating or reversing the progress of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The term "prevent" or "preventing" as used herein means to keep from happening or existing. The term "administering" as used herein refers to either directly administering a compound of the present invention, or administering a prodrug, derivative, or analog of same, that will form an effective amount of the compound within a mammal.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder.

The present invention also provides a use of a compound of formula (I), including a pharmaceutically acceptable salt thereof, in the preparation of a medicament for the treatment of a central nervous system disease or disorder. The present invention further provides a compound of formula (I) for use in treating a disease or disorder.

A compound of formula (I) can allosterically modulate the mGlu5 receptor. An allosteric modulator that enhances or potentiates the affinity of an orthosteric ligand for the mGluR5 receptor and/or enhances or potentiates an orthosteric agonist's efficacy is an allosteric enhancer (or potentiator) or positive allosteric modulator (PAM). See e.g., May, L. T. *Annu. Rev. Pharmacol. Toxicol.* 2007, 47, 1-51. An allosteric modulator that reduces or diminishes the affinity of an orthosteric ligand for the mGluR5 receptor and/or reduces or diminishes an orthosteric agonist's efficacy is an allosteric antagonist (or inhibitor) or negative allosteric modulator (NAM). Id.

In some embodiments, the mammal of the method of the invention is a human.

In some embodiments of the method or use of the invention, the central nervous system disease or disorder is a cognitive or neurodegenerative disease or disorder. In some such embodiments, the cognitive or neurodegenerative disease or disorder is selected from a group consisting of a mood disorder, an anxiety, a schizophrenia (including schizoaffective disorders), Alzheimer's disease, Parkinson's disease, multiple sclerosis, Huntington's chorea, amyotrophic lateral sclerosis, Creutzfeld-Jakob disease, a trauma-induced neurodegeneration, AIDS-induced encephalopathy, another infection-related encephalopathy (i.e., a non-AIDS-induced encephalopathy), Fragile X syndrome, an autism spectrum disorder, and a combination thereof.

As used herein, the phrase "mood disorder" refers to any of several psychological disorders characterized by abnormalities of emotional state, such as, without limitation, bipolar disorders, depressive disorders, cyclothymic disorders, dysthymic disorders, mood disorders due to a general medical condition, mood disorders not otherwise specified and substance-induced mood disorders; and as characterized by the *Diagnostic and Statistical Manual of Mental Disorders*, Fourth Edition (DSM-IV) (American Psychiatric Association: Arlington, Va., 1994).

As used herein, the phrase "autism spectrum disorder" (ASD) refers to a disorder that causes severe and pervasive impairment in thinking, feeling, language, and the ability to relate to others, which is often first diagnosed in early childhood and range from a severe form, called autistic disorder ("classic" autism), through pervasive development disorder not otherwise specified (PDD-NOS), to a much milder form, Asperger syndrome. The phrase, as used herein, also includes Rett syndrome and childhood disintegrative disorder, and as used herein, is synonymous with the phrase, "pervasive developmental disorders" (PDDs).

In some such embodiments, the mood disorder is a depression (i.e., a depressive disorder). In some such embodiments, the depression is selected from the group consisting of atypical depression, bipolar depression, unipolar depression, major depression, endogenous depression (i.e., acute depression with no obvious cause), involutional depression (i.e., depression that occurs in mid-life or the elderly), reactive depression (i.e., depression caused by an obvious traumatic life episode), postpartum depression, primary depression (i.e., depression that has no obvious physical or psychological cause such as a medical illness or disorder), psychotic depression, and secondary depression (i.e., depression that seems to be caused by some other underlying condition such another medical illness or disorder).

In some such embodiments, the anxiety disease or disorder is selected from a group comprising generalized anxiety disorder, panic anxiety, obsessive compulsive disorder, social phobia, performance anxiety, post-traumatic stress disorder, acute stress reaction, an adjustment disorder, a hypochondriacal disorder, separation anxiety disorder, agoraphobia, a specific phobia, anxiety disorder due to general medical condition, substance-induced anxiety disorder, alcohol withdrawal-induced anxiety, and a combination thereof.

In some embodiments, the central nervous system disease or disorder of the method or use comprising a compound of the invention is a seizure disease or disorder. In some embodiments, the seizure disease or disorder is selected from the group consisting of a convulsion, epilepsy, status epilepticus, and a combination thereof.

In some embodiments, the central nervous system disease or disorder of the method or use comprising a compound of the invention is a pain disease or disorder selected from the group consisting of inflammatory pain, neuropathic pain and migraine pain. In some embodiments, the neuropathic pain or migraine pain disease or disorder is selected from the group consisting of allodynia, hyperalgesic pain, phantom pain, neuropathic pain related to diabetic neuropathy, neuropathic pain related to migraine, and a combination thereof.

In some embodiments, the central nervous system disease or disorder of the method or use comprising a compound of the invention is a neuronal hyperexcitation state disease or disorder. In some embodiments, the neuronal hyperexcitation state disease or disorder is a neuronal hyperexcitation state in medicament withdrawal, a neuronal hyperexcitation state in intoxication, or a combination thereof.

In some embodiments of the method or use comprising a compound of the invention, at least one symptom of the cognitive neurodegenerative, psychiatric or neurological disease or disorder is treated.

In some embodiments, the cognitive, neurodegenerative, psychiatric or neurological disease or disorder is a depression. In some such embodiments, the at least one symptom of the depression is depressed feeling, depressed mood, loss of interest or pleasure in some or all activities, changes in appetite, changes in weight, changes in sleep patterns, lack of energy, fatigue, low self esteem, diminished capacity for thinking, concentration, or decisiveness, feelings of hopelessness or worthlessness, psychomotor agitation or retardation, self-reproach, inappropriate guilt, frequent thoughts of death or suicide, plans or attempts to commit suicide, or a combination thereof.

In some embodiments, the cognitive, neurodegenerative, psychiatric or neurological disease or disorder is an anxiety. In some such embodiments, the at least one symptom of anxiety is apprehension, fear, trembling, muscle aches, insomnia, abdominal upsets, dizziness, irritability, persistent, recurring thoughts, compulsions, heart palpitations, chest pain, chest discomfort, sweating, tingling sensations, feeling of choking, fear of losing control, flashbacks, nightmares, intrusive thoughts, intrusive recollections, avoidance behaviors, emotional numbing, an inability to sleep, anxious feelings, overactive startle response, hypervigilance, outbursts of anger, faintness, blushing, profuse sweating, or a combination thereof.

In some embodiments, the cognitive, neurodegenerative, psychiatric or neurological disease or disorder is schizophrenia. In some such embodiments, the at least one symptom of schizophrenia is a positive symptom selected from the group consisting of hallucination, delusion, paranoia, and a combination thereof. In some such embodiments, the symptom of schizophrenia is a negative symptom selected from the group consisting of social withdrawal, flat affect, anhedonia, decreased motivation, and a combination thereof. In some such embodiments, the symptom of schizophrenia is a cognitive symptom selected from the group consisting of severe deficit in attention, severe deficit in object naming, severe deficit in working memory, severe deficit in long-term memory storage, severe deficit in executive functioning, a slowing of information processing, a slowing of neural activity, long term depression, and a combination thereof.

In some embodiments of the method or use comprising a compound of the invention, the cognitive, neurodegenerative, psychiatric or neurological disease or disorder is Parkinson's disease. In some such embodiments, the at least one symptom of Parkinson's disease is levodopa-induced dyskinesia, poor balance, Parkinsonian gait, bradykinesia, rigidity, tremor, change in speech, loss of facial expression, micrographia, difficulty swallowing, drooling, pain, dementia, confusion, a sleep disturbance, constipation, a skin problem, depression, fear, anxiety, difficulty with memory, slowed thinking, sexual dysfunction, an urinary problem, fatigue, aching, loss of energy, or a combination thereof.

In some embodiments, the cognitive, neurodegenerative, psychiatric or neurological disease or disorder is Alzheimer's disease. In some such embodiments, the at least one symptom of Alzheimer's disease is impairment in memory, impairment in attention, impairment in judgment, impairment in decision-making, impairment in orientation to physical surroundings, language impairment, impairment in speed-dependent activities, impairment in abstract reasoning, impairment in visuospatial abilities, impairment in executive functioning, impairment in behavioral disturbances, disinterest and passivity, apathy, inappropriate dressing, poor self care, agitation, violent outburst, aggression, depression, anxiety, hallucination, delusion, change in personality, change in mood, dementia, or a combination thereof.

In some embodiments, the cognitive, neurodegenerative, psychiatric or neurological disease or disorder is multiple sclerosis. In some such embodiments, the at least one symptom of multiple sclerosis is optic neuritis blurred vision, eye pain, loss of color vision, blindness, diplopia double vision, nystagmus jerky eye movements, ocular dysmetria, constant under- or overshooting eye movements, internuclear ophthalmoplegia, nystagmus, diplopia, movement and sound phosphenes, diplopia, afferent pupillary defect, motor paresis, monoparesis, paraparesis, hemiparesis, quadraparesis plegia, paraplegia, hemiplegia, tetraplegia, quadriplegia, spasticity, dysarthria, muscle atrophy, spasms, cramps, hypotonia, dorms, myoclonus, myokymia, restless leg syndrome, foot-drop dysfunctional reflexes (MRSs, Babinski's, Hoffman's, Chaddock's), paraesthesia, anaesthesia, neuralgia, neuropathic pain, neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, retrograde ejaculation, frigidity, constipation, fecal urgency, depression, cognitive dysfunction, dementia, mood swings, emotional lability, euphoria, bipolar syndrome, anxiety, aphasia, dysphasia, fatigue, uhthoffs symptom, gastroesophageal reflux, a sleeping disorder, or a combination thereof.

The present invention further provides a method of treating gastroesophageal reflux, the method comprises administering a therapeutically effective amount of at least one compound of claim 1 or a pharmaceutically acceptable salt thereof to a mammal in need thereof. The present invention further provides a use of a compound of the invention in the preparation of a medicament for the treatment of gastroesophageal reflux. The present invention further provides a compound of the invention for use in treating gastroesophageal reflux.

The present invention further provides a method of treating alcohol dependence, the method comprises administering a therapeutically effective amount of at least one compound of claim 1 or a pharmaceutically acceptable salt thereof to a mammal in need thereof. The present invention further provides a use of a compound of the invention in the preparation of a medicament for the treatment of alcohol dependence. The present invention further provides a compound of the invention for use in treating alcohol dependence.

In some embodiments, the compound of the present invention is used in the preparation of a medicament for treatment of a central nervous system disease or disorder. In some embodiments, the central nervous disease or disorder is as previously disclosed herein.

Another aspect of the present invention is a process for producing the compounds of the present invention.

Preparation of the Compounds of the Present Invention

The compounds of the present invention may be prepared, without limitation, according to one of the general methods outlined below. For example, Schemes 1-9 that follow are intended as an illustration of some embodiments of the invention and no limitation of the present invention is implied because of them.

The following defines acronyms as used herein unless specified otherwise in a particular instance.

BINAP=2,2'-bis(diphenylphosphino)-1,1'-binaphthyl, CAS No. 98327-87-8; BOP=benzotriazole-1-yl-oxy-tris-(dimethylamino)-phosphonium hexafluorophosphate, CAS No. 56602-33-6; DCM=dichloromethane or methylene chloride; DIEA=DIPEA=N,N-diisopropylethylamine, CAS No. 7087-68-5; DMA=N,N-dimethylacetamide, CAS No. 127-19-5; DMC=dimethylimidazolinium chloride; DMF=N,N-dimethylformamide, CAS No. 68-12-2; DPPA=Diphenylphosphoryl azide, CAS No. 26386-88-9; EDCI=N-Ethyl-N'-(3-dimethylaminopropyl)carbodiimide hydrochloride, CAS No. 93128-40-6; HATU=2-(7-Azabenzotriazole-1-yl)-1,1,3,3-tetramethyluronium tetrafluoroborate, CAS No. 873798-09-5; HBTU=2-(1H-Benzotriazole-1-yl)-1,1,3,3-Tetramethyluronium hexafluorophosphate, CAS No. 94790-37-1; NMP=N-Methyl-Pyrrolidone, CAS No. 872-50-4; PyBOP=benzotriazol-1-yl-oxytripyrrolidinophosphonium hexafluorophosphate, CAS No. 128625-52-5; RT or rt=room temperature; TEA=triethanolamine, CAS No. 102-71-6; THF=tetrahydrofuran, CAS No. 109-99-9; and TMSOK=potassium trimethylsilanolate, CAS No. 10519-96-7

Symmetrical amides of the formula (I-A) ($R^1=R^2$) can be prepared via the process outlined in Scheme 1 using customary amidation procedures from intermediate A, where $R^1$ is equal to $R^2$, and $R^1$ and $R^2$ are as previously defined herein.

Scheme 1

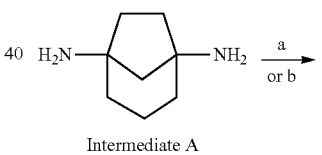

Intermediate A

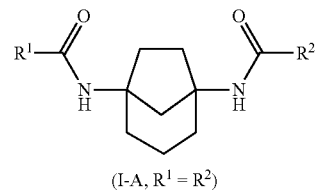

(I-A, $R^1 = R^2$)

a) $R^1CO_2H$, PyBOP (or BOP or EDCl), DIEA or Et$_3$N, CH$_2$Cl$_2$ (or THF or DMF);
b) $R^1COCl$, DIEA or Et$_3$N, CH$_2$Cl$_2$

Unsymmetrical amides of formula (I-A) ($R^1 \neq R^2$) can be prepared via the process outlined in Scheme 2. Amidation of intermediate A with a mixture of $R^1COCl$ and $R^2COCl$, or a mixture of $R^1CO_2H$ and $R^2CO_2H$ using customary amidation procedures affords unsymmetrical amides of formula (I-A), where $R^1$ and $R^2$ are as previously defined herein.

Scheme 2

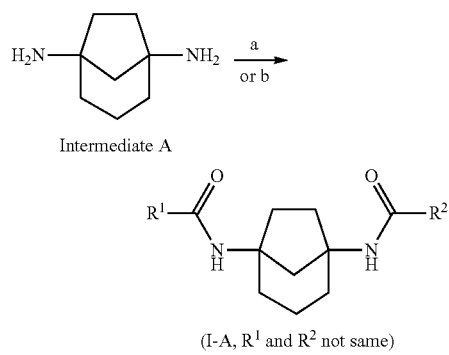

(I-A, R¹ and R² not same)

a) 1.0 eq. R¹CO₂H, 1.0 eq. R²CO₂H, DIEA, PyBOP (or BOP, DMC, EDCl), CH₂Cl₂
b) 1.0 eq. R¹COCl, 1.0 eq. R²COCl, DIEA, CH₂Cl₂

Compounds of formula (I-A) can also be made via the process outlined in Scheme 3. Amidation of intermediate B with R²COCl or R²CO₂H using customary amidation procedures affords unsymmetrical amides of formula (I-A).

Scheme 3

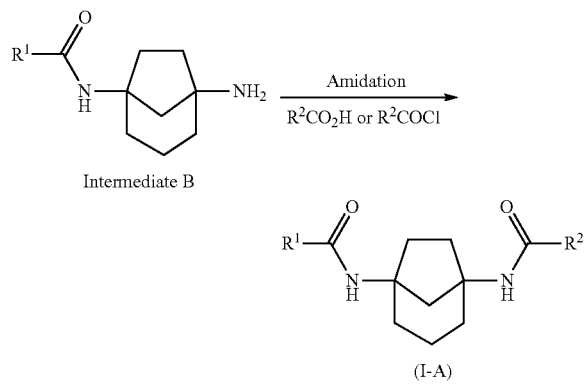

Compounds of formula (I-B) can be made via the process outlined in Scheme 4 or 5 using customary amidation procedures from intermediate C or D, respectively

Scheme 4

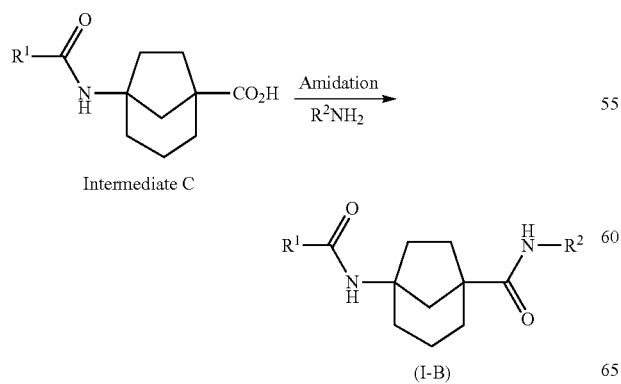

Scheme 5

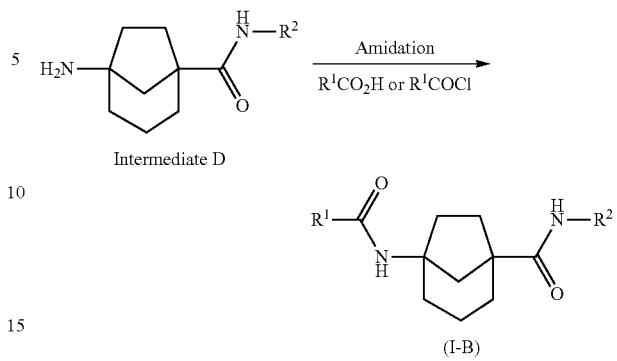

Intermediate A can be made via the process outlined in Scheme 6. Esterification of commercially available cyclohexane-1,3-dicarboxylic acid 1 under conditions such as in methanol in the presence of chlorotrimethylsilane affords ester 2. Alkylation of compound 2 with 1-bromo-2-chloroethane in the presence of base produces bicyclic compound 3. Saponification of 3 under standard conditions gives carboxylic acid 4, which is converted to diamine intermediate A via a standard Curtius rearrangement, followed by the treatment with aqueous (aq.) HCl.

Scheme 6

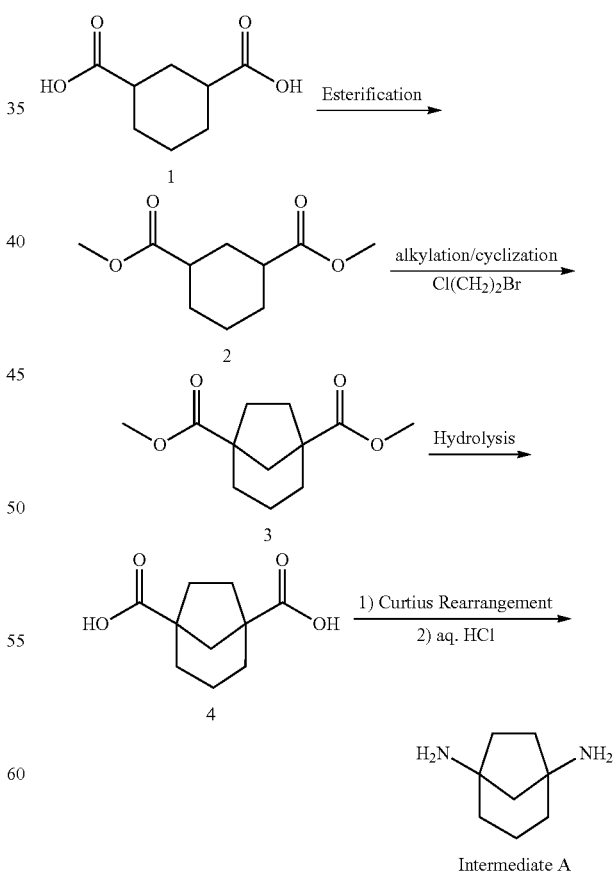

Intermediate B can be made via the process outlined in Scheme 7. Mono-hydrolysis of di-ester 2 by treatment with base such as 0.5 eq Ba(OH)$_2$ in methanol affords carboxylic acid 5, which was converted to benzyl carbamate 6 via standard Curtius rearrangement, followed by the treatment with benzyl alcohol. Saponification of compound 6 under standard conditions produces carboxylic acid 7, which was converted to compound 8 via standard Curtius rearrangement, followed by the treatment with tert-butyl alcohol. Removal of benzyl group under standard conditions such as hydrogenation gives amine 9. Customary amidation of amine 9 with R$^1$CO$_2$H followed by removal of BOC (butoxycarbonyl) protecting group under standard conditions affords intermediate B.

gives amine 10. Customary amidation of 1.0 with R$^1$CO$_2$H or R$^1$COCl yields amide 11. Saponification of compound 11 under standard conditions produces intermediate C, which upon Curtius rearrangement followed by the treatment with aq. HCl, affords intermediate B.

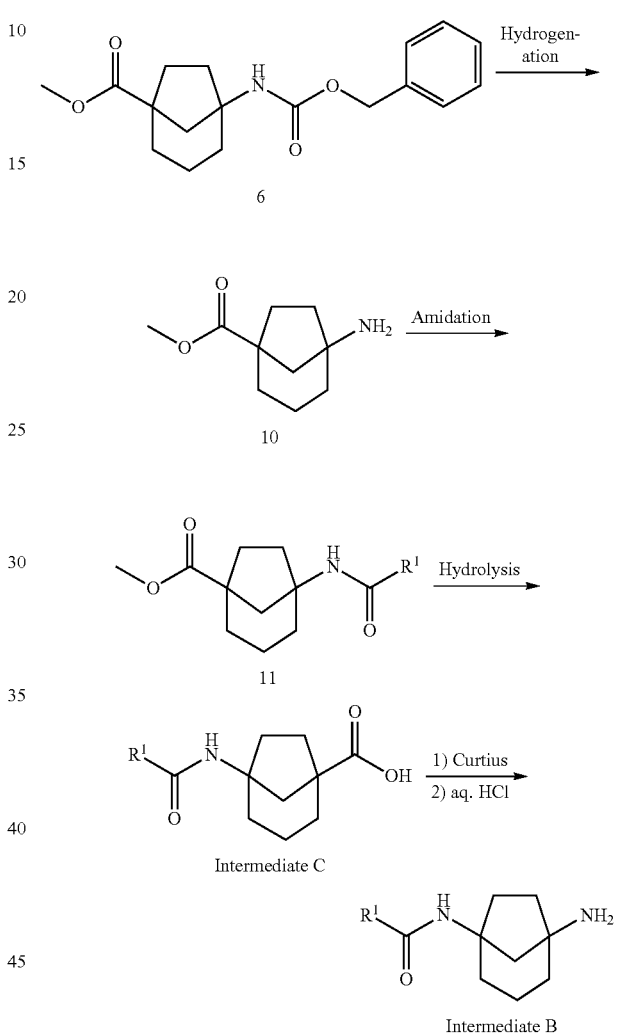

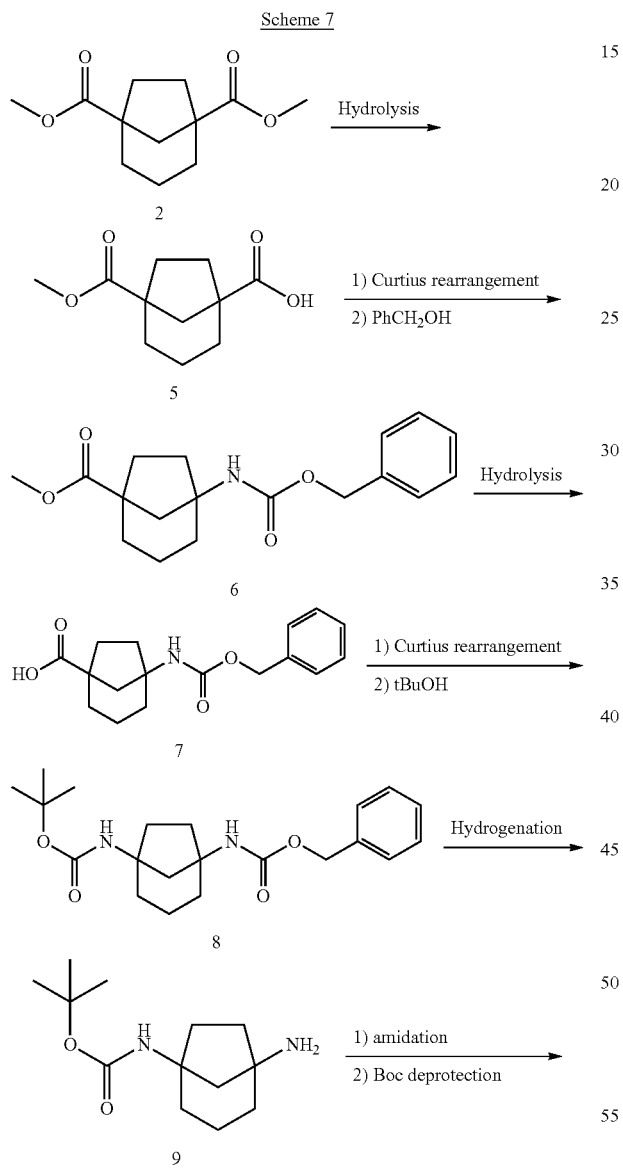

Intermediate B and C can be made via the process outlined in Scheme 8. Removal of benzyl protecting group of compound 6 under standard conditions such as hydrogenation Intermediate D can be made via the process outlined in Scheme 9. Amidation of compound 5 and R$^2$NH$_2$ using customary conditions affords compound 12. Saponification of ester 12 under standard conditions yields carboxylic acid 13, which upon standard Curtius rearrangement followed by the treatment of aq. HCl, yields intermediate D.

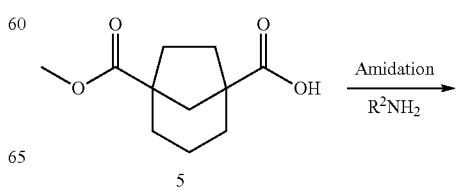

-continued

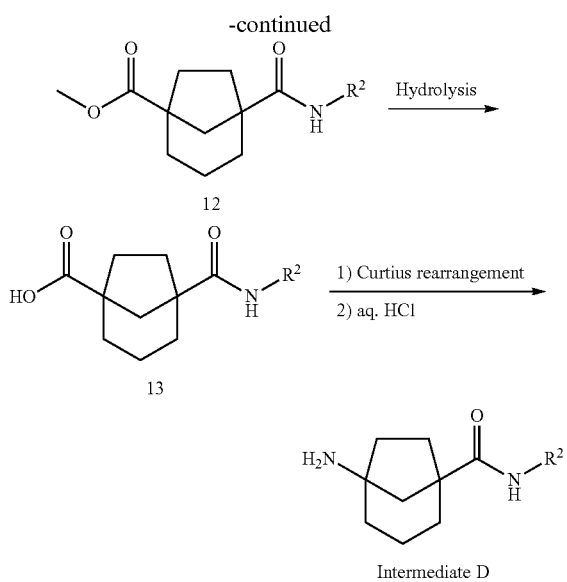

Intermediate D

Experimental Section

1. General Methods

Unless specifically stated otherwise, the experimental procedures were performed under the following conditions. All operations were carried out at room temperature (about 18° C. to about 25° C.) under nitrogen atmosphere. Evaporation of solvent was carried out using a rotary evaporator under reduced pressure or in a high performance solvent evaporation system HT-4X (Genevac Inc., Gardiner, N.Y., USA). The course of the reaction was followed by thin layer chromatography (TLC) or liquid chromatography-mass spectrometry (LC-MS), and reaction times are given for illustration only. Silica gel chromatography was carried out on a CombiFlash® system (Teledyne Isco, Inc., Lincoln, Nebr., USA) with pre-packed silica gel cartridge or performed on Merck silica gel 60 (230-400 mesh). The structure and purity of all final products was assured by at least one of the following analytical methods: nuclear magnetic resonance (NMR) and LC-MS. NMR spectra was recorded on a Bruker Avance™ 300 spectrometer (Bruker BioSpin Corp., Billerica, Mass., USA) or a Varian UNITY INOVA™ 400 (Varian, Inc., Palo Alto, Calif., USA) or Bruker AVANCE III 500 MHz UltraShield-Plus™ Digital NMR Spectrometer using the indicated solvent. Chemical shift (δ) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; br=broad; etc. Unless stated otherwise, mass spectra were obtained using electrospray ionization (ESMS) via a Micromass® Platform II system or a Quattro Micro™ system (both from Waters Corp., Milford, Mass., USA) or 1200RRLC/6140 SQ system (Agilent Technologies, Santa Clara, Calif., USA), and $(M+H)^+$ is reported.

PREPARATION OF INTERMEDIATES OF THE INVENTION

Unless specified otherwise, all starting materials and reagents were obtained from commercial suppliers, such as Sigma-Aldrich (St. Louis, Mo., USA) and its subsidiaries, and used without further purification.

Intermediate 1

Bicyclo[2.1]octane-1,5-diamine dihydrochloride

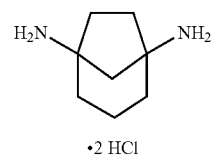

Intermediate 1 was prepared via the process of Scheme 6, supra, as follows:

Step 1: Cyclohexane-1,3-dicarboxylic acid dimethyl ester

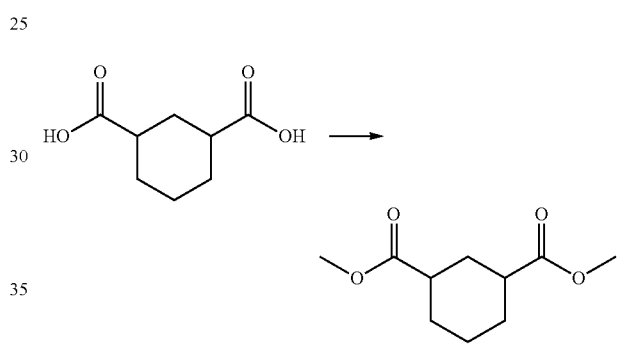

1,3-Cyclohexanedicarboxylic acid (45.0 g, 261.4 mmol) was dissolved in methanol (250 mL). Chlorotrimethylsilane (10.00 mL, 78.79 mmol) was added and the reaction was stirred at room temperature for 4 days. The reaction was checked by LC-MS with the product mass $[M+H]^+$ 201 seen. The mixture was concentrated under reduced pressure. The resulting residue was diluted with dichloromethane (200 mL). The organic layer was then washed with saturated. $NaHCO_3$, dried over sodium sulfate, filtered and concentrated under reduced pressure to give a slightly viscous, clear and colorless oil. The oil was redissolved in anhydrous THF and concentrated to yield 49.5 g (95%) of cyclohexane-1,3-dicarboxylic acid dimethyl ester, which was used in the next step without further purification.

Step 2: Bicyclo[3.2.1]octane-1,5-dicarboxylic acid dimethyl ester

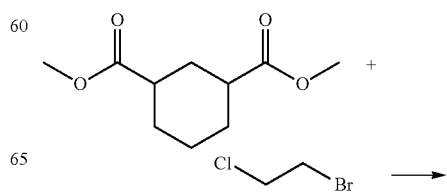

-continued

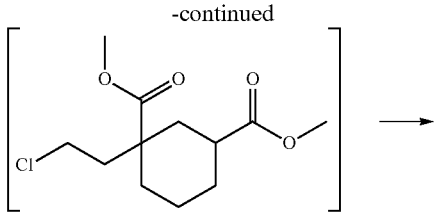

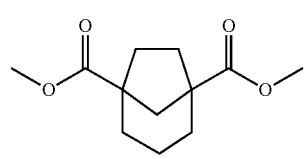

A solution of N,N-diisopropylamine (4.5 mL, 32 mmol) in tetrahydrofuran (25 mL) was cooled at −78° C. and treated with 1.6 M of n-butyllithium in hexane (19 mL). The reaction was warmed to 0° C., stirred for 5 minutes, then cooled back to −78° C. 1,3-Dimethyl-3,4,5,6-tetrahydro-2(1H)-pyrimidinone (15 mL, 120 mmol) was added dropwise over 20 minutes, then a solution of cyclohexane-1,3-dicarboxylic acid dimethyl ester (5.0 g, 25 mmol) in tetrahydrofuran (10 mL) was added dropwise and the mixture stirred for 1 hour at the same temperature. Then a solution of 1-bromo-2-chloroethane (2.9 mL, 35 mmol) in tetrahydrofuran (8 mL) was added dropwise. The reaction was allowed to return slowly to room temperature and stirred overnight. The reaction mixture was cooled to 0° C. and quenched with saturated ammonium chloride solution. The reaction mixture was concentrated under reduced pressure and the resulting residue was diluted with a small amount of water and extracted with dichloromethane (4×50 mL). The organic layers were combined, dried over anhydrous sodium sulfate, filtered, and concentrated under reduced pressure. The resulting residue was purified with chromatography to give the intermediate 1-(2-chloro-ethyl)-cyclohexane-1,3-dicarboxylic acid dimethyl ester (1.22 g). A solution of N,N-diisopropylamine (0.91 mL, 6.50 mmol) in tetrahydrofuran (10 mL) was cooled at −78° C. and treated with 1.6 M of n-butyllithium in hexane (4.06 mL). The reaction was warmed to 0° C., stirred for 5 minutes, and then cooled back to −78° C. 1,3-Dimethyl-3,4,5,6-tetrahydro-2(1H)-pyrimidinone (2.24 mL, 18.6 mmol) was added dropwise over 20 minutes, then a solution of 1-(2-chloro-ethyl)-cyclohexane-1,3-dicarboxylic acid dimethyl ester (1.22 g, 4.64 mmol) in tetrahydrofuran (10 mL) was added dropwise and the mixture was stirred for 1 hour at the same temperature. The reaction was allowed to return slowly at room temperature and stirred overnight. The reaction was quenched with saturated ammonium chloride solution and concentrated under reduced pressure. The resulting residue was diluted with a small amount of water and extracted with dichloromethane (4×50 mL). The organic layers were combined, dried over anhydrous sodium sulfate, filtered, and evaporated to give crude product (3.05 g) containing DMPU. The product was used in the next step without further purification.

Step 3: Bicyclo[3.2.1]octane-1,5-dicarboxylic acid

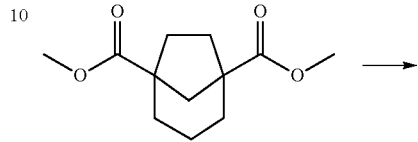

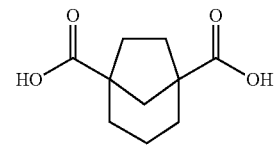

A solution of bicyclo[3.2.1]octane-1,5-dicarboxylic acid dimethyl ester (crude 3.01 g from step 2) in tetrahydrofuran (100 mL) was treated with 1 M of lithium hydroxide in water (75 mL) and warmed at 70° C. for 6 hours. The reaction was concentrated under reduced pressure and the resulting residue was partitioned between water and ethyl acetate. The aqueous layer was collected and washed again with ethyl acetate. The aqueous layer was acidified with 1N HCl to pH 2, and then extracted with ethyl acetate. The organic layer was collected, dried over anhydrous sodium sulfate, filtered, and evaporated to afford 725 mg of white solid, which was used in the next step without further purification.

Step 4: Bicyclo[3.2.1]octane-1,5-diamine dihydrochloride

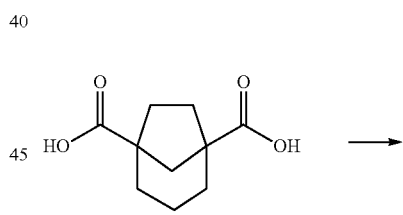

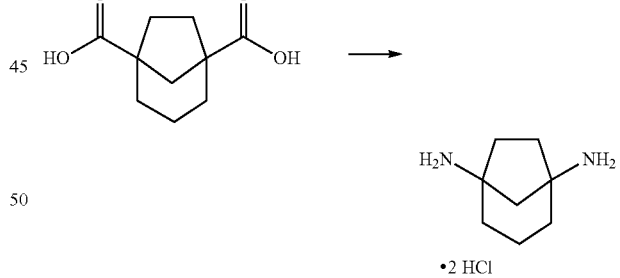

A mixture of bicyclo[3.2.1]octane-1,5-dicarboxylic acid (725 mg, 3.66 mmol) in toluene (60 mL) was treated with triethylamine (1.53 mL, 11.0 mmol) followed by diphenylphosphonic azide (1.97 mL, 9.14 mmol). The reaction was heated at 90° C. for 3 hours, then cooled down to rt and concentrated under reduced pressure. The resulting residue was cooled in an ice bath and treated with 6 M of hydrogen chloride in water (60 mL). The ice bath was removed and the reaction was stirred overnight. Most of the water was removed in vacuo and the resulting residue was stirred with acetonitrile in an ice bath until a colorless precipitate deposited. The precipitate was collected by filtration and dried under vacuum to give product as a colorless solid (250 mg, 32%), which was used in the next step without further purification.

Intermediate 2

6-Methyl-pyrazine-2-carboxylic acid (5-amino-bicyclo[3.2.1]oct-1-yl)-amide HCl salt

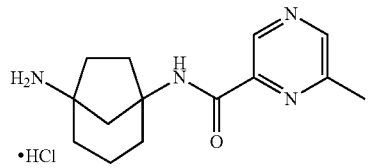 [SMILES: Cl ; Cc1cncc(C(=O)NC23CCCC(N)(CC2)C3)n1]

Intermediate 2 was prepared via the processes of Schemes 7 and 8, supra, as follows:

Step 1: Bicyclo[3.2.1]octane-1,5-dicarboxylic acid diethyl ester

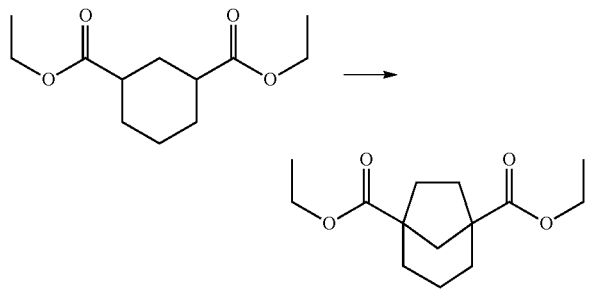

Using the similar experimental procedure described in the synthesis of intermediate 1 (step 2), bicyclo[3.2.1]octane-1,5-dicarboxylic acid diethyl ester was prepared from cyclohexane-1,3-dicarboxylic acid diethyl ester at 0.18 mol reaction scale. ESI-MS m/z: 277 (M+H)$^+$ Step 2: Bicyclo[3.2.1]octane-1,5-dicarboxylic acid monoethyl ester

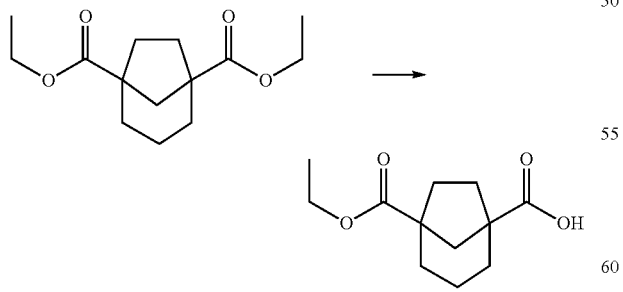

Partial hydrolysis of the cyclized diethyl ester 4 (1.3 g) was done by using barium hydroxide (0.5 equiv) in ethanol (13 mL) and water (3 mL) at ambient temperature for 18 hours. The reaction was concentrated under reduced pressure and the resulting residue was partitioned between water and ethyl acetate. The aqueous layer was collected and washed again with ethyl acetate. The aqueous layer was acidified with 1N HCl to pH 2, and then extracted with ethyl acetate. The organic layer was collected, dried over anhydrous sodium sulfate, filtered and concentrated under reduced pressure. The residue was purified by column chromatography to afford 500 mg (47%) of the desired product. ESI-MS m/z: 227 (M+H)$^+$ Step 3: 5-Benzyloxycarbonylamino-bicyclo[3.2.1]octane-1-carboxylic acid ethyl ester

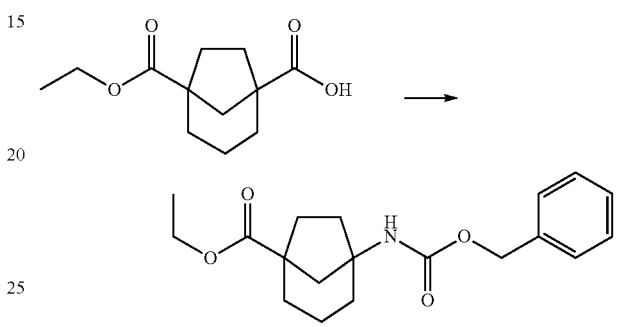

Using the similar experimental procedure described in the synthesis of intermediate 1 (step 4), 5-benzyloxycarbonylamino-bicyclo[3.2.1]octane-1-carboxylic acid ethyl ester was made from bicyclo[3.2.1]octane-1,5-dicarboxylic acid monoethyl ester via Curtius rearrangement with DPPA and TEA in toluene, and quenched with BnOH at 1.1-10.3 mmol reaction scales. ESI-MS m/z: 332 (M+H)$^+$ Step 4: 5-Amino-bicyclo[3.2.1]octane-1-carboxylic acid ethyl ester

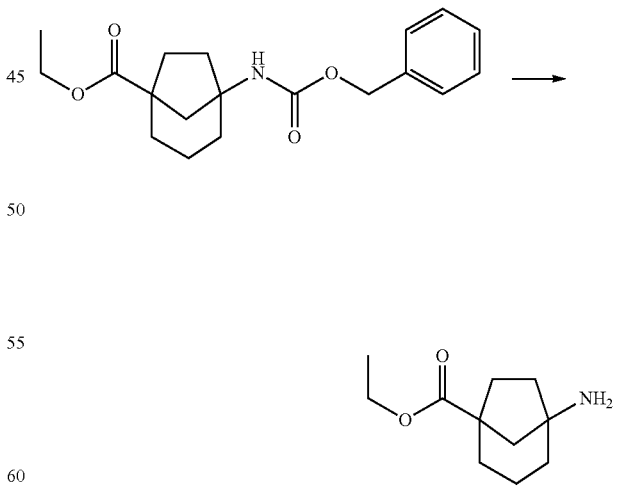

5-Benzyloxycarbonylamino-bicyclo[3.2.1]octane-1-carboxylic acid ethyl ester (2.0 g, 6.05 mmol) was dissolved in ethanol (50.0 mL). Pd/C (10%) (0.32 g, 0.30 mmol) was added. The mixture was hydrogenated under 50 psi H$_2$ at rt for 6 hrs. The catalyst was removed by filtration through a layer of Celite®. The filtrate was concentrated under reduced pressure to afford 1.0 g (84%) of the desired product. ESI-MS m/z: 198 (M+H)⁺.

Step 5: 5-[(6-Methyl-pyrazine-2-carbonyl)-amino]-bicyclo[3.2.1]octane-1-carboxylic acid ethyl ester

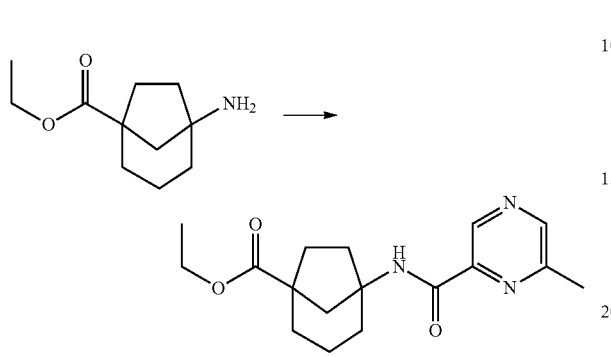

5-Amino-bicyclo[3.2.1]octane-1-carboxylic acid ethyl ester (0.5 g, 2.53 mmol) was dissolved in methylene chloride (10.0 mL, 156 mmol). 6-Methylpyrazine-2-carboxylic acid (0.35 g, 2.53 mmol), benzotriazol-1-yloxytris(dimethylamino)phosphonium hexafluorophosphate (1.12 g, 2.53 mmol) and triethylamine (0.71 mL, 5.07 mmol) in methylene chloride (10.0 mL, 156 mmol) were added. The mixture was stirred at rt for 2 hours. The mixture was concentrated under reduced pressure. The resulting residue was purified on the CombiFlash® system (hexane/ethyl acetate: 100/0 to 30/70 in 8 min, then hexane/ethyl acetate: 30/70) to afford 0.60 g (75%) of the desired product. ESI-MS m/z: 318 (M+H)⁺

Step 6: 5-[(6-Methyl-pyrazine-2-carbonyl)-amino]-bicyclo[3.2.1]octane-1-carboxylic acid

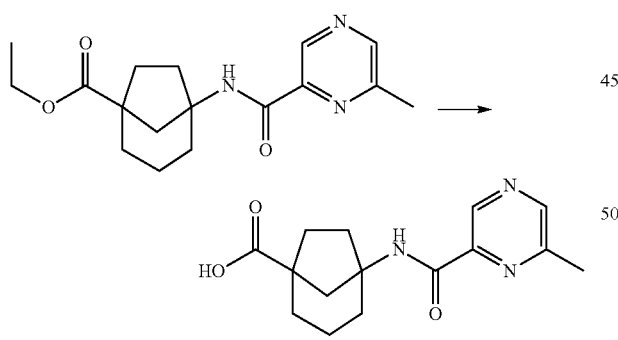

5-[6-Methyl-pyrazine-2-carbonyl)-amino]-bicyclo[3.2.1]octane-1-carboxylic acid ethyl ester (0.60 g, 1.89 mmol) was dissolved in tetrahydrofuran (10.0 mL, 123 mmol). Lithium hydroxide monohydrate (0.40 g, 9.45 mmol) in water (6.0 mL, 333 mmol) was added. The mixture was stirred at rt overnight. The mixture was concentrated under reduced pressure. The resulting residue was participated in ethyl acetate (20 mL) and water (20 mL). The aqueous layer was collected, acidified with 1N HCl to pH 2, and extracted with ethyl acetate (60 mL). The organic layer was washed with brine, dried over Na₂SO₄ and concentrated to afford 340 mg (62%) of the desired product as white solid. It was used in the next step without further purification. ESI-MS m/z: 290 (M+H)⁺

Step 7: 6-Methyl-pyrazine-2-carboxylic acid (5-amino-bicyclo[3.2.1]oct-1-yl)-amide HCl salt

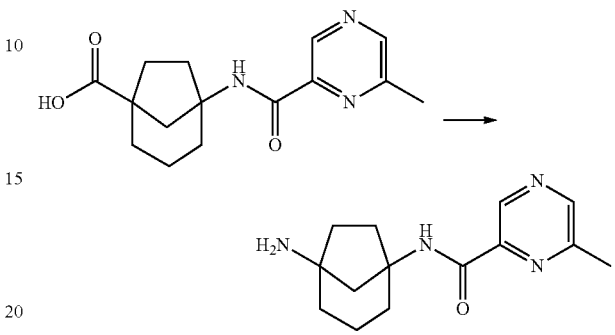

5-[(6-Methyl-pyrazine-2-carbonyl)-amino]-bicyclo[3.2.1]octane-1-carboxylic acid (0.340 g, 1.18 mmol) was suspended in toluene (10.0 mL, 93.9 mmol). Triethylamine (0.20 mL, 1.41 mmol) was added, followed by the addition of diphenylphosphonic azide (0.25 mL, 1.18 mmol). The mixture was stirred at rt for 2 hours. Then the mixture was heated at 90° C. for 1 hour. The mixture was cooled down and poured into ice-cold 6M aqueous HCl and stirred overnight. The aqueous layer was collected, cooled down at 0° C., basified with solid K₂CO₃ to pH 11, and extracted with CH₂Cl₂ (4×25 mL). The combined organic layer was dried over Na₂SO₄ and concentrated under reduced pressure. The resulting residue was dissolved in CH₂Cl₂, 4 M HCl/dioxane (1.0 mL). The mixture was concentrated under reduced pressure to afford 345 mg (99%) of 6-methyl-pyrazine-2-carboxylic acid (5-amino-bicyclo[3.2.1]oct-1-yl)-amide HCl salt as a white solid. It was used in the next step without further purification. ESI-MS m/z: 261 (M+H)⁺.

Intermediate 3

N-(5-Aminobicyclo[3.2.1]octan-1-yl)-3-fluorobenzamide

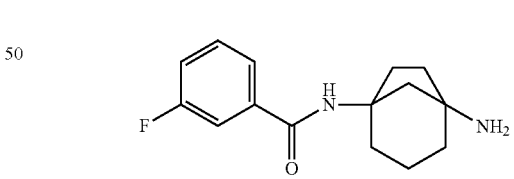

Step 1: Dimethyl cyclohexane-1,3-dicarboxylate

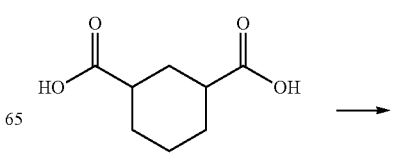

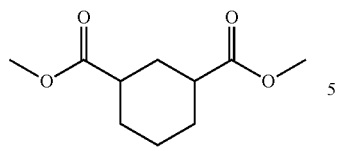

To a solution of 1,3-cyclohexanedicarboxylic acid (25 g, 0.145 mol) in methanol (250 mL) was added concentrated $H_2SO_4$ (10 mL) and the reaction solution was refluxed overnight. After cooled to room temperature, methanol was removed under reduced pressure. The residue was diluted with ethyl acetate (500 mL), washed with Sat. $Na_2CO_3$ (2×300 mL) and brine (100 mL), dried over $MgSO_4$ and concentrated under reduced pressure to give 27.4 g (94%) of dimethyl cyclohexane-1,3-dicarboxylate as a light yellow oil. ESI-MS m/z: 201 $(M+H)^+$.

Step 2: Dimethyl 1-(3-chloropropyl)cyclohexane-1,3-dicarboxylate

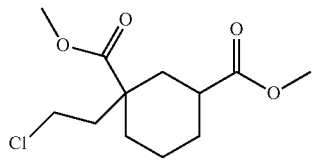

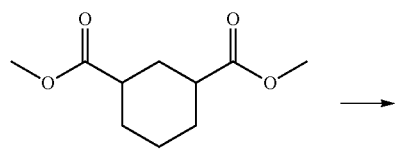

To a pre-cooled (−78° C.) solution of lithium diisopropylamide (36 mL, 78 mmol) in THF (250 mL) was added DMPU (30.5 g, 238 mmol) dropwise (not allowing the temperature to exceed −65° C.), followed by an addition of a solution of dimethyl cyclohexane-1,3-dicarboxylate (11.9 g, 59.5 mmol) in THF (50 mL) at −78° C. over 20 min. After stirring at −78° C. for one hour, 1-bromo-2-chloroethane (11.1 g, 77.4 mmol) was added and the reaction mixture was slowly warmed up to room temperature overnight. After quenched with Sat. $NH_4Cl$ (100 mL), the mixture was concentrated under reduced pressure. The resulting residue was diluted with water (200 mL) and extracted with dichloromethane (4×100 mL). The combined organic layer was washed with water (100 mL) and brine (100 mL), dried over $MgSO_4$ and concentrated under reduced pressure. The resulting residue was purified by column chromatography (silica gel, petroleum ether/ethyl acetate: 20/1) to afford 11.7 g (75%) of dimethyl 1-(3-chloropropyl)cyclohexane-1,3-dicarboxylate as a yellow oil. ESI-MS m/z: 263 $(M+H)^+$.

Step 3: Dimethyl bicyclo[3.3.1]nonane-1,5-dicarboxylate

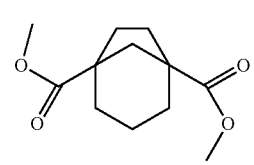

To a pre-cooled (−78° C.) solution of lithium diisopropylamide (27 mL, 54 mmol) in THF (80 mL) was added DMPU (30.2 g, 236 mol) dropwise, followed by an addition of dimethyl 1-(3-chloropropyl)cyclohexane-1,3-dicarboxylate (11.7 g, 44.7 mmol) in THF (50 mL) within 20 min. The reaction mixture was stirred for 30 min at −78° C. and then allowed to warm up to room temperature over a period of 1.5 h. After quenched with saturated ammonium chloride (100 mL), the mixture was concentrated under reduced pressure. The residue was diluted with water (300 mL) and extracted with dichloromethane (4×100 mL). The combined organic layer was washed with water (100 mL) and brine (100 mL), dried over $MgSO_4$ and concentrated under reduced pressure. The residue was purified by column chromatography (silica gel, petroleum ether/ethyl acetate: 20/1) to afford 8.32 g (82%) of dimethyl bicyclo[3.3.1]nonane-1,5-dicarboxylate as a light yellow oil. ESI-MS m/z: 227 $(M+H)^+$.

Step 4: 5-(methoxycarbonyl)bicyclo[3.3.1]nonane-1-carboxylic acid

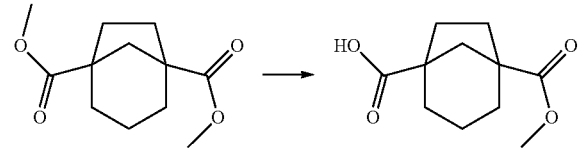

A solution of dimethyl bicyclo[3.3.1]nonane-1,5-dicarboxylate (8.32 g, 36.8 mmol) and $Ba(OH)_2 \cdot 8H_2O$ (5.80 g, 18.4 mmol) in ethanol (40 mL) and $H_2O$ (10 mL) was refluxed overnight. After cooled to room temperature, the mixture was concentrated under reduced pressure. The resulting residue was added diluted with water (100 mL) and extracted with diethyl ether (3×200 mL). The combined organic layer was washed with brine (100 mL), dried over sodium sulfate and concentrated under reducer pressure to recover starting material as an orange oil. The aqueous phase was adjusted to pH 1~2 with 2N aq. HCl, and extracted with dichloromethane (3×100 mL). The combined organic layer was washed with brine (100 mL), dried over sodium sulfate and concentrated under reduced pressure to afford 1.8 g (67%) of 5-(methoxycarbonyl)bicyclo[3.3.1]nonane-1-carboxylic acid as a white solid. ESI-MS m/z: 213 (M+H)+.

Step 5: Methyl 5-(benzyloxycarbonylamino)bicyclo[3.2.1]octane-1-carboxylate

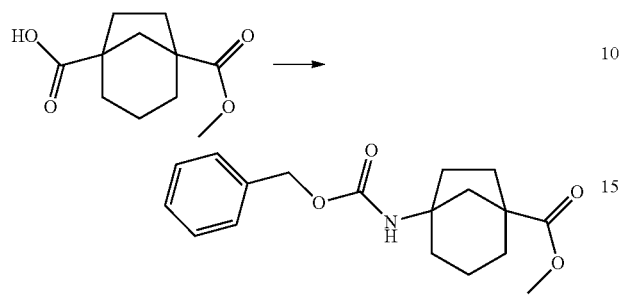

A mixture of 5-(methoxycarbonyl)bicyclo[3.3.1]nonane-1-carboxylic acid (5.23 g, 24.7 mmol), diphenylphosphonic azide (8.0 mL, 36.9 mmol) and triethylamine (1.0 mL, 136 mmol) in toluene (150 mL) was stirred at room temperature for one hour, and then refluxed for three hours. Benzyl alcohol (4.0 mL, 38.7 mmol) was added, and the mixture was continued to reflux overnight. After cooled to room temperature, the reaction mixture was diluted with ethyl acetate (100 mL), washed with Sat. NaHCO$_3$ and brine, dried over sodium sulfate, and concentrated under reduced pressure. The resulting residue was purified by column chromatography (silica gel, petroleum ether/ethyl acetate: 20/1) to afford 10 g of methyl 5-(benzyloxycarbonylamino)bicyclo-[3.2.1]octane-1-carboxylate (containing BnOH) as a brown oil. ESI-MS m/z: 318 (M+H)+. It was used in the next step without purification.

Step 6: 5-(benzyloxycarbonylamino)bicyclo[3.2.1]octane-1-carboxylic acid

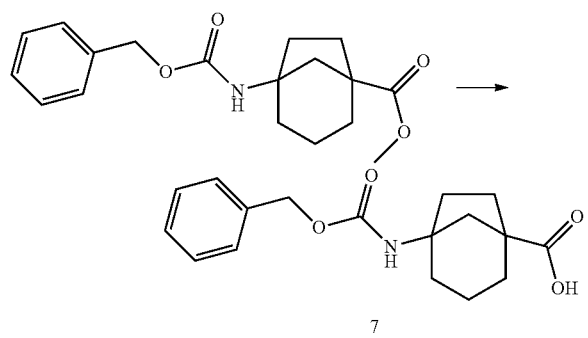

To a solution of methyl 5-(benzyloxycarbonylamino)bicyclo-[3.2.1]octane-1-carboxylate (25 g, crude product) in methanol (200 mL) was added NaOH (5N, 50 mL) and the reaction mixture was refluxed for two hours. After cooled to room temperature, the mixture was concentrated under reduced pressure. The residue was diluted with water (100 mL) and extracted with diethyl ether (3×100 mL) to remove the organic impurities. The aqueous phase was adjusted to pH 1~2 with 2N aq. HCl, and extracted with dichloromethane (3×100 mL). The combined organic layer was washed with brine, dried over sodium sulfate and concentrated under reduced pressure to afford 8.5 g (49%, steps 5 and 6) of 5-(benzyloxycarbonylamino)bicyclo[3.2.1]octane-1-carboxylic acid as a yellow oil. ESI-MS m/z: 304 (M+H)+.

Step 7: Benzyl 5-aminobicyclo[3.2.1]octan-1-ylcarbamate

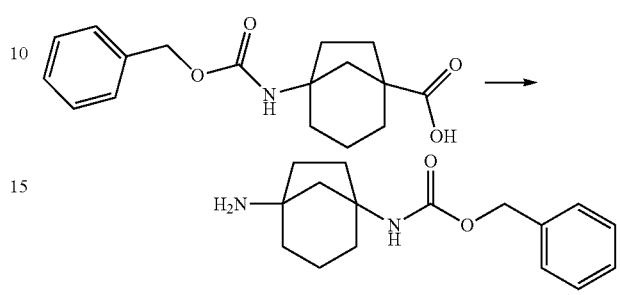

A mixture of 5-(benzyloxycarbonylamino)bicyclo[3.2.1]octane-1-carboxylic acid (8.5 g, 28.0 mmol), diphenylphosphonic azide (9.3 g, 33.8 mmol) and triethylamine (5 mL, 68 mmol) in toluene (150 mL) was stirred at room temperature for one hour, and then refluxed for three hours. After cooled to 0° C., a solution of TMSOK (10.7 g, 83.6 mmol) in THF (85 mL) was added. The reaction mixture was warmed to room temperature and stirred for 1 h, and then quenched with 5% citric acid (20 mL) and concentrated under reduced pressure. The residue was treated with aq. HCl (2 N, 200 mL) at 0° C. The resulting mixture was extracted with ethyl acetate (3×100 mL). The aqueous phase was adjusted to pH 9~10 with Na$_2$CO$_3$ and extracted with dichloromethane/methanol (10/1, 3×150 mL). The combined organic layer was washed with water and brine, dried over sodium sulfate and concentrated under reduced pressure to afford 5.13 g (42%) of benzyl 5-aminobicyclo[3.2.1]octan-1-ylcarbamate as a yellow solid. ESI-MS m/z: 275 (M++1).

Step 8: Benzyl (5-(3-fluorobenzamido)bicyclo[3.2.1]octan-1-yl)carbamate

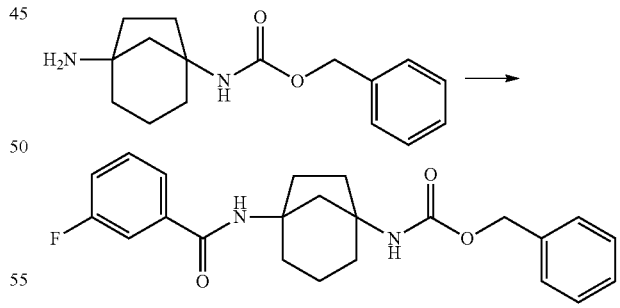

To a solution of benzyl 5-aminobicyclo[3.2.1]octan-1-ylcarbamate (402 mg, 1.47 mmol) and 3-fluorobenzoic acid (309 mg, 2.21 mmol) in DMF (20 mL) was added HATU (1.12 g, 2.95 mmol) and DIPEA (1 mL). After stirring at room temperature for 1 hour, water (100 mL) was added and the mixture was extracted with ethyl acetate (3×50 mL). The combined organic layer was washed with brine, dried over Na$_2$SO$_4$, and concentrated under reduced pressure. The resulting residue was purified by column chromatography (silica gel, petroleum ether/ethyl acetate: 2/1) to give 513 mg (88%) of benzyl (5-(3-fluorobenzamido)bicyclo[3.2.1]octan-1-yl) carbamate as a white solid. ESI-MS m/z: 397 (M+H)⁺.

Step 9: N-(5-aminobicyclo[3.2.1]octan-1-yl)-3-fluorobenzamide

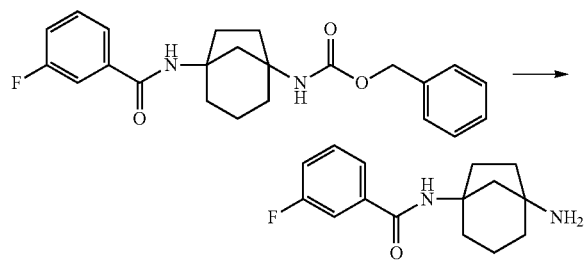

To a solution of N-(5-aminobicyclo[3.2.1]octan-1-yl)-3-fluorobenzamide (513 mg, 1.30 mmol) in methanol (50 mL) was added Pd/C (10%, 100 mg) and the reaction mixture was hydrogenated (1 atm) at room temperature overnight. The reaction mixture was then filtered through a Celite pad, and the filtrate was concentrated under reduced pressure to afford N-(5-aminobicyclo[3.2.1]octan-1-yl)-3-fluorobenzamide (329 mg, 97%) as a white solid. ESI-MS m/z: 263 (M+H)⁺.

Intermediate 4

6-Methyl-pyrazine-2-carboxylic acid(5-amino-bicyclo[3.2.1]oct-1-yl)-amide

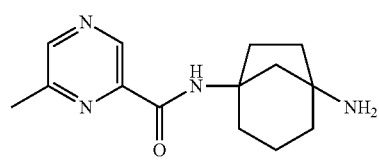 [SMILES: Cc1cncc(C(=O)NC23CCCC(N)(CC2)C3)n1]

Intermediate 4 (6.2 g) was prepared analogously to intermediate 3. ¹H NMR (500 MHz, CD₃OD): δ 8.87 (s, 1H), 8.56 (s, 1H), 2.51 (s, 3H), 2.11-2.01 (m, 3H), 1.89-1.88 (m, 1H), 1.71-1.40 (m, 8H). ESI-MS m/z: 261 (M+H)⁺.

Intermediate 5

N-(5-aminobicyclo[3.2.1]oct-1-yl)-3-chlorobenzamide

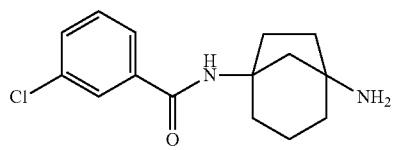 [SMILES: NC12CCCC(NC(=O)c3cccc(Cl)c3)(CC1)C2]

Intermediate 5 (2.3 g) was prepared analogously to intermediate 3. ¹H NMR (500 MHz, CDCl₃): δ 7.71 (s, 1H), 7.61 (d, J=2.5 Hz, 1H), 7.46 (d, J=2.0 Hz, 1H), 7.37-7.34 (m, 1H), 6.13 (s, 1H), 2.21-1.98 (m, 4H), 1.79-1.52 (m, 10H). ESI-MS m/z: 279 (M+H)⁺.

Intermediate 6

N-(5-aminobicyclo[3.2.1]oct-1-yl)-3-methylbenzamide

Intermediate 6 (2.2 g) was prepared analogously to intermediate 3. ¹H NMR (500 MHz, CDCl₃): δ 7.54-7.50 (m, 2H), 7.22 (d, J=6.0 Hz, 2H), 6.78 (s, 1H), 2.32 (s, 1H), 2.12-1.96 (m, 4H), 1.69-1.41 (m, 10H). ESI-MS m/z: 259 (M+H)⁺.

Intermediate 7

N-(5-aminobicyclo[3.2.1]oct-1-yl)-5-fluoropyridine-2-carboxamide

Intermediate 7 (50 mg) was prepared analogously to intermediate 3. ESI-MS m/z: 264 (M+H)⁺.

Intermediate 8

N-(5-aminobicyclo[3.2.1]oct-1-yl)-5-methylpyrazine-2-carboxamide

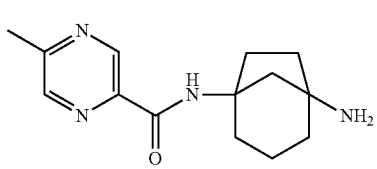 [SMILES: Cc1cnc(C(=O)NC23CCCC(N)(CC2)C3)cn1]

Intermediate 8 (500 mg) was prepared analogously to intermediate 3. ESI-MS m/z: 261 (M+H)⁺.

Intermediate 9

N-(5-aminobicyclo[3.2.1]oct-1-yl)pyrazine-2-carboxamide

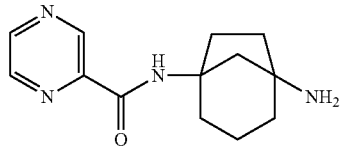 [SMILES: NC12CCCC(NC(=O)c3cnccn3)(CC1)C2]

Intermediate 9 (800 mg) was prepared analogously to intermediate 3. $^1$H NMR (500 MHz, CDCl$_3$): δ 9.39 (d, J=1.0 Hz, 1H), 8.74 (d, J=2.0 Hz, 1H), 8.50 (d, J=2.0 Hz, 1H), 7.88 (s, 1H), 2.27-1.97 (m, 4H), 1.82-1.70 (m, 6H), 1.60-1.54 (m, 4H). ESI-MS m/z: 247 (M+H)⁺.

Intermediate 10

N-(5-aminobicyclo[3.2.1]oct-1-yl)pyridine-2-carboxamide

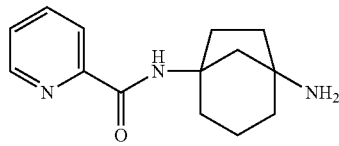 [SMILES: NC12CCCC(NC(=O)c3ccccn3)(CC1)C2]

Intermediate 10 (2.8 g) was prepared analogously to intermediate 3. $^1$H NMR (500 MHz, CDCl3): δ 8.53-8.52 (m, 1H), 8.18-8.15 (m, 2H), 7.86-7.82 (m, 1H), 7.42-7.40 (m, 1H), 2.28-1.97 (m, 4H), 1.80-1.55 (m, 10H). ESI-MS m/z: 246 (M+H)⁺.

Intermediate 11

6-Methyl-pyridine-2-carboxylic acid (5-amino-bicyclo[3.2.1]oct-1-yl)-amide

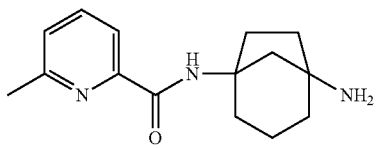 [SMILES: Cc1cccc(C(=O)NC23CCCC(N)(CC2)C3)n1]

Intermediate 11 (3.2 g) was prepared analogously to intermediate 3. $^1$H NMR (500 MHz, CDCl$_3$): δ 8.20 (s, 1H), 7.96 (d, =9.5 Hz, 1H), 7.69 (t, J=9.5 Hz, 1H), 7.26 (d, J=9.5 Hz, 1H), 2.56 (s, 3H), 2.28-1.96 (m, 4H), 1.80-1.55 (m, 10H); ESI-MS m/z: 260 (M+H)⁺.

Intermediates 12 and 13

{(1S,5R)-5-[(6-Methyl-pyrazine-2-carbonyl)-amino]-bicyclo[3.2.1]oct-1-yl}-carbamic acid tert-butyl ester and {(1R,5S)-5-[(6-methyl-pyrazine-2-carbonyl)-amino]-bicyclo[3.2.1]oct-1-yl}-carbamic acid tert-butyl ester Intermediate 12

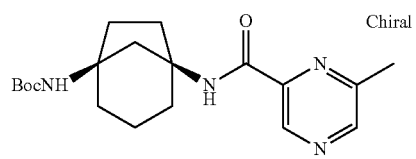

Intermediate 13

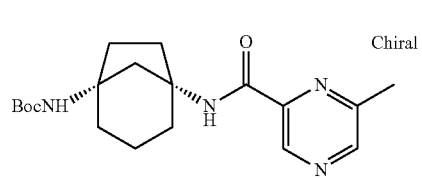

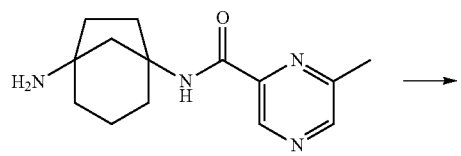

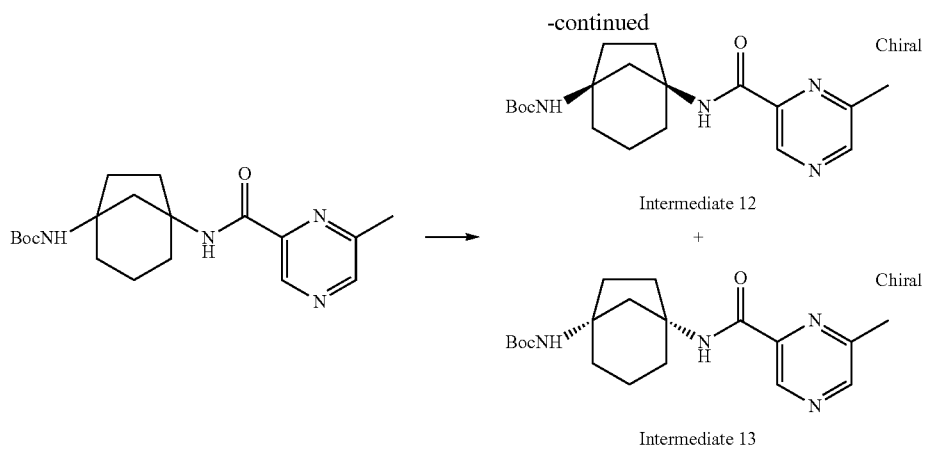

Intermediate 12

+

Intermediate 13

To a solution of 6-methyl-pyrazine-2-carboxylic acid (5-amino-bicyclo[3.2.1]oct-1-yl)-amide (intermediate 4, 1.15 g, 4.42 mmol) in DCM (20.0 mL) was added triethylamine (1.23 mL, 8.83 mmol), followed by di-tert-butyldicarbonate (1.01 g, 4.64 mmol). After stirring at rt overnight, the reaction mixture was concentrated under reduced pressure. The residue was purified on the CombiFlash® system (hexane/ethyl acetate: 100/0 to 40/60 in 8 mins, then hexane/ethyl acetate: 40/60) to afford 1.0 g (63%) of {5-[(6-methyl-pyrazine-2-carbonyl)-amino]-bicyclo[3.2.1]oct-1-yl}-carbamic acid tert-butyl ester (ESI-MS m/z: 361 (M+H)$^+$), which was then resolved on a Supercritical Fluid Chromatography (SFC) preparative separation system (Column: 30×150 mm OJ-H (Chiral Technologies Inc). Solvent: isopropyl alcohol/CO$_2$: 5/95. Detector: UV at 250 nm. Flow rate: 100 mL/min). The front peak was arbitrarily assigned as {(1S,5R)-5-[(Pyrazine-2-carbonyl)-amino]-bicyclo[3.2.1]oct-1-yl}-carbamic acid tert-butyl ester (intermediate 12, 0.32 g, ESI-MS m/z: 361 (M+H)$^+$) and the back peak was arbitrarily assigned as {(1R,5S)-5-[(pyrazine-2-carbonyl)-amino]-bicyclo[3.2.1]oct-1-yl}-carbamic acid tert-butyl ester (intermediate 13, 0.33 g, ESI-MS m/z: 361 (M+H)$^+$).

Intermediates 14 and 15

{(1S,5R)-5-[(Pyrazine-2-carbonyl)-amino]-bicyclo[3.2.1]oct-1-yl}-carbamic acid tert-butyl ester and {(1R,5S)-5-[(pyrazine-2-carbonyl)-amino]-bicyclo[3.2.1]oct-1-yl}-carbamic acid tert-butyl ester

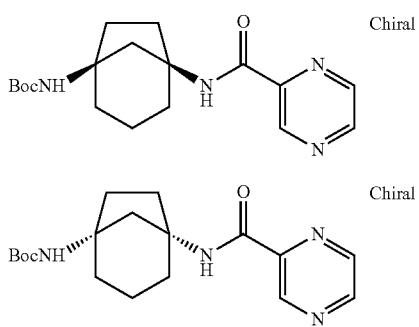

Intermediate 14

Intermediate 15

In an analogous manner to intermediates 12 and 13, intermediates 14 (ESI-MS m/z: 347 (M+H)$^+$) and 15 (ESI-MS m/z: 347 (M+H)$^+$) were made from 0.95 g of intermediate 9. The absolute stereochemistry of 14 and 15 were arbitrarily assigned.

Intermediates 16 and 17

{(1S,5R)-5-[(6-Methyl-pyridine-2-carbonyl)-amino]bicyclo[3.2.1]oct-1-yl}-carbamic acid tert-butyl ester and {(1R,5S)-5-[(6-methyl-pyridine-2-carbonyl)-amino]bicyclo[3.2.1]oct-1-yl}-carbamic acid tert-butyl ester

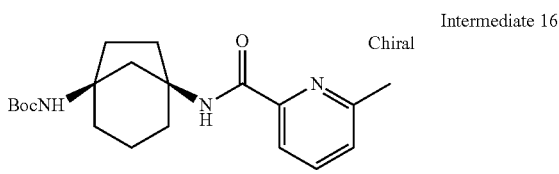

Intermediate 16

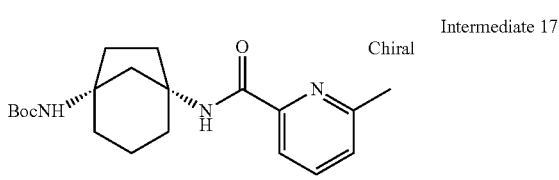

Intermediate 17

In an analogous manner to intermediates 12 and 13, intermediates 16 (2.2 g, ESI-MS m/z: 360 (M+H)$^+$) and 17 (2.2 g, ESI-MS m/z: 360 (M+H)+) were made from 5.2 g of intermediate 11. The absolute stereochemistry of 16 and 17 were arbitrarily assigned.

Intermediates 18 and 19

{(1S,5R)-5-[(Pyridine-2-carbonyl)amino]bicyclo[3.2.1]oct-1-yl}-carbamic acid tert-butyl ester and {(1R,5S)-5-[(pyridine-2-carbonyl)-amino]bicyclo[3.2.1]oct-1-yl}-carbamic acid tert-butyl ester

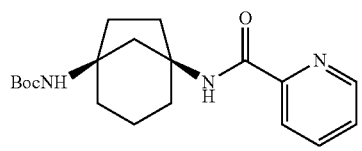

Intermediate 18

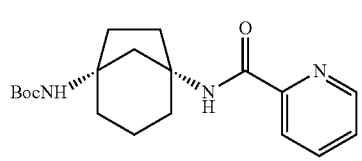

Intermediate 19

In an analogous manner to intermediates 12 and 13, intermediates 18 (1.2 g, ESI-MS m/z: 346 (M+H)+) and 19 (1.25 g, ESI-MS m/z: 346 (M+H)+) were made from 2.0 g of intermediate 10. The absolute stereochemistry of 16 and 1.7 were arbitrarily assigned.

Intermediate 20

Pyrazine-2-carboxylic acid (1S,5R)-5-amino-bicyclo[3.2.1]oct-1-yl)-amide HCl salt

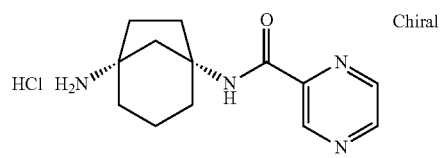 [SMILES: Cl ; N[C@]12CCC[C@](NC(=O)c3cnccn3)(CC1)C2]

To a solution of {(1R,5S)-5-[(pyrazine-2-carbonyl)-amino]-bicyclo[3.2.1]oct-1-yl}-carbamic acid tert-butyl ester (intermediate 15, 0.9 g, 2.6 mmol) in methylene chloride (5.0 mL) was added 4 M of hydrogen chloride in 1,4-dioxane (6.5 mL). After stirring at room temperature overnight, the reaction mixture was concentrated under reduced pressure to afford 0.7 g of pyrazine-2-carboxylic acid ((1S,5R)-5-amino-bicyclo[3.2.1]oct-1-yl)-amide HCl salt, which was used in the next step without further purification. ESI-MS m/z: 247 (M+H)+.

Intermediate 21

6-Methyl-pyridine-2-carboxylic acid ((1S,5R)-5-amino-bicyclo[3.2.1]oct-1-yl)-amide

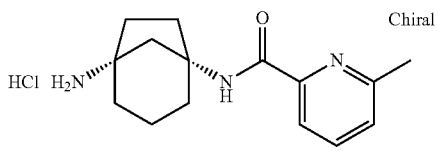 [SMILES: Cl ; Cc1cccc(C(=O)N[C@@]23CCC[C@@](N)(CC2)C3)n1]

In an analogous manner to intermediate 20, intermediate 21 (2.0 g, ESI-MS m/z: 260 (M+H)+) was prepared from intermediate 17 (2.5 g).

Intermediate 22

6-Methyl-pyridine-2-carboxylic acid ((1R,5S)-5-amino-bicyclo[3.2.1]oct-1-yl)-amide

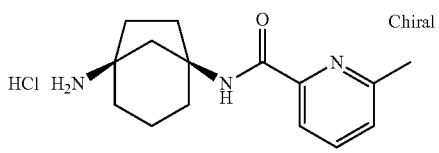 [SMILES: Cl ; Cc1cccc(C(=O)N[C@]23CCC[C@](N)(CC2)C3)n1]

In an analogous manner to intermediate 20, intermediate 22 (1.36 g, ESI-MS m/z: 260 (M+H)+) was prepared from intermediate 16 (2.2 g).

Intermediate 23

Pyridine-2-carboxylic acid ((1S,5R)-5-amino-bicyclo[3.2.1]oct-1-yl)-amide

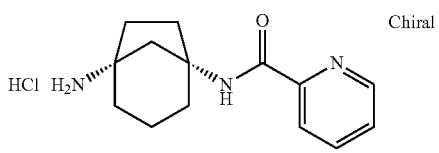 [SMILES: Cl ; N[C@]12CCC[C@](NC(=O)c3ccccn3)(CC1)C2]

In an analogous manner to intermediate 20, intermediate 23 (1.1 g, ESI-MS m/z: 246 (M+H)$^+$) was prepared from intermediate 19 (1.25 g).

Intermediate 24

Pyridine-2-carboxylic acid ((1R,5S)-5-amino-bicyclo[3.2.1]oct-1-yl)-amide

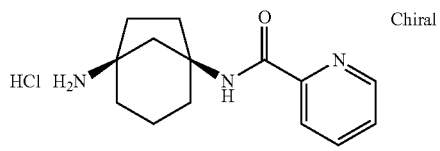 [SMILES: Cl ; N[C@@]12CCC[C@@](NC(=O)c3ccccn3)(CC1)C2]

In an analogous manner to intermediate 20, intermediate 24 (1.05 g, ESI-MS m/z: 246 (M+H)$^+$) was prepared from intermediate 18 (1.2 g).

Intermediate 25

6-Methyl-pyrazine-2-carboxylic acid ((1S,5R)-5-amino-bicyclo[3.2.1]oct-1-yl)-amide HCl salt

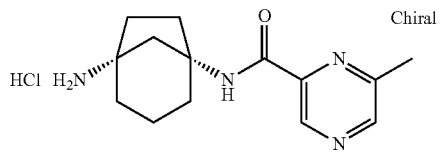 [SMILES: Cl ; Cc1cncc(C(=O)N[C@@]23CCC[C@@](N)(CC2)C3)n1]

In an analogous manner to intermediate 20, intermediate 25 (1.2 g, ESI-MS m/z: 261 (M+H)$^+$) was prepared from intermediate 13 (1.5 g).

Intermediate 26

5-(6-Methylpyrazine-2-carboxamido)bicyclo[3.2.1]octane-1-carboxylic acid

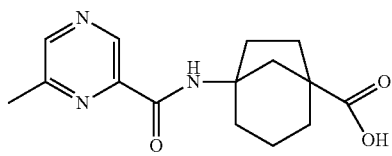 [SMILES: Cc1cncc(C(=O)NC23CCCC(C(=O)O)(CC2)C3)n1]

Intermediate 26 was prepared via the processes of Scheme 8, supra, as follows:

Step 1: Methyl 5-aminobicyclo[3.2.1]octane-1-carboxylate

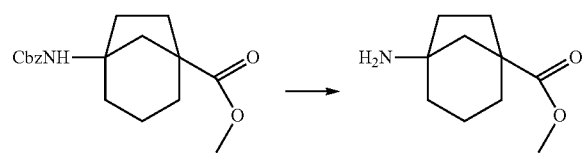

To a solution of methyl 5-(benzyloxycarbonylamino)bicyclo-[3.2.1]octane-1-carboxylate (10 g) in methanol (150 mL) was added 10% Pd/C (1 g) and the reaction mixture was stirred under H$_2$ (1 atm) at room temperature overnight. The reaction mixture was filtered through a Celite pad, and the filtrate was concentrated. The residue was treated with aqueous HCl (2N, 200 mL) at 0° C. and then extracted with ethyl acetate (3×100 mL) to remove organic impurities. The aqueous phase was adjusted to pH 9-10 with Sat. Na$_2$CO$_3$ and extracted with dichloromethane/methanol (10/1, 3×100 mL). The combined organic layer was washed with water (100 mL) and brine (100 mL), dried over sodium sulfate and concentrated under reduced pressure to afford 2.98 g of methyl 5-aminobicyclo[3.2.1]octane-1-carboxylate as a yellow oil. ESI-MS m/z: 184 (M+H)$^+$.

Step 2: methyl 5-(6-methylpyrazine-2-carboxamido)bicyclo[3.2.1]octane-1-carboxylate

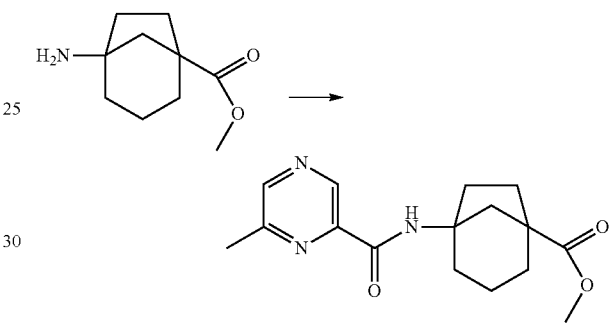

To a solution of methyl 5-aminobicyclo[3.2.1]octane-1-carboxylate (0.98 g, 5.36 mmol) and 6-methylpyrazine-2-carboxylic acid (0.89 g, 6.45 mmol) in DCM (30 mL) and TEA (2 mL) was added PyBOP (3.35 g, 6.44 mmol). After stirring at room temperature overnight, water (30 mL) was added and the mixture was extracted with DCM (3×50 mL). The combined organic layer was washed with Sat. NaHCO$_3$ (50 mL) and brine (50 mL), dried over Na$_2$SO$_4$ and concentrated under reduced pressure. The residue was purified by column chromatography (silica gel, petroleum ether/ethyl acetate: 1/1) to afford 1.28 g (79%) of methyl 5-(6-methylpyrazine-2-carboxamido)bicyclo[3.2.1]octane-1-carboxylate as an off-white solid. ESI-MS m/z: 304 (M+H)$^+$.

Step 3: 5-(6-methylpyrazine-2-carboxamido)bicyclo[3.2.1]octane-1-carboxylic acid

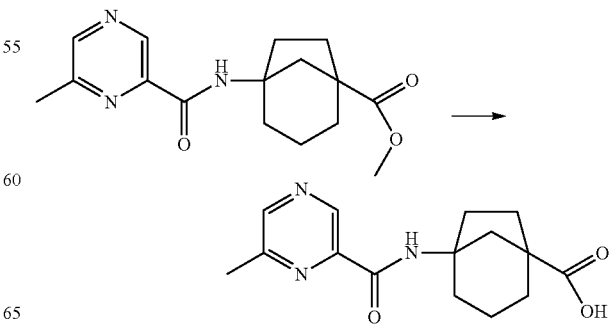

A solution of methyl 5-(6-methylpyrazine-2-carboxamido)bicyclo[3.2.1]octane-1-carboxylate (1.28 g, 4.21 mmol) and LiOH (0.15 g, 6.25 mmol) in methanol (30 mL) and H$_2$O (3 mL) was refluxed for two hours. After cooled to room temperature, methanol was removed under reduced pressure. The residue was partitioned between water (50 mL) and diethyl ether (50 mL) to remove organic impurities. The aqueous phase was adjusted to pH 1~2 with 2N aq. HCl and then extracted with dichloromethane (3×50 mL). The combined organic layer was washed with water (50 mL) and brine (50 mL), dried over Na$_2$SO$_4$ and concentrated under reduced pressure to afford 1.11 g (91%) of 5-(6-methylpyrazine-2-carboxamido)bicyclo[3.2.1]octane-1-carboxylic acid as a white solid. ESI-MS m/z: 290 (M+H)$^+$.

Intermediate 27

5-amino-N-(2-methylpyrimidin-4-yl)bicyclo[3.2.1]octane-1-carboxamide

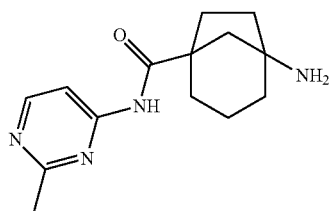 [SMILES: Cc1nccc(NC(=O)C23CCCC(N)(CC2)C3)n1]

Intermediate 27 was prepared via the processes of Scheme 9, supra, as follows:

Step 1: 5-(benzyloxycarbonylamino)bicyclo[3.2.1]octane-1-carboxylic acid

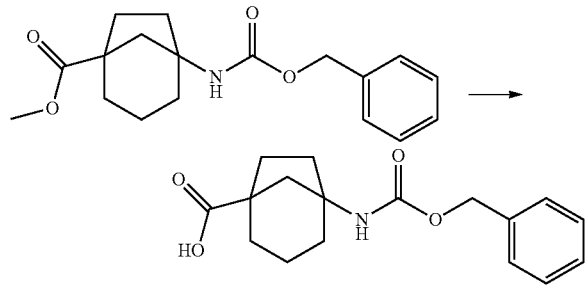

To a solution of 5-(benzyloxycarbonylamino)bicyclo-[3.2.1]octane-1-carboxylate (10 g, 31.5 mmol) in MeOH (150 mL) was added NaOH (2N, 50 mL) and the reaction solution was stirred at room temperature overnight. The organic solvent was removed under reduced pressure and the remaining aqueous solution was extracted with ethyl acetate (20 mL) to remove the organic impurities, and then adjusted to pH 3 with 2N aq. HCl. The acidic aqueous solution was extracted with ethyl acetate (3×20 mL) and the combined organic layer was washed with brine, dried over Na$_2$SO$_4$ and concentrated to give 9 g (95%) 5-(benzyloxycarbonylamino)bicyclo[3.2.1]octane-1-carboxylic acid as a colorless oil, which was solidified after standing at room temperature overnight. ESI-MS m/z: 304 (M+H)$^+$.

Step 2: Benzyl 5-carbamoylbicyclo[3.2.1]octan-1-ylcarbamate

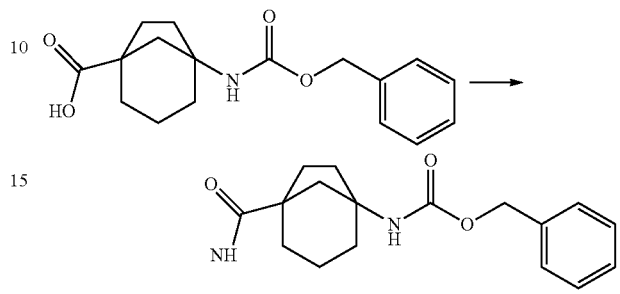

To a solution of 5-(benzyloxycarbonylamino)bicyclo[3.2.1]octane-1-carboxylic acid (1.0 g, 3.3 mmol) in DCM (30 mL) was added dropwise oxalyl chloride (5 mL), followed by two or three drops of DMF. After stirring at room temperature for an hour, the reaction mixture was concentrated under reduced pressure. The resulting residue was dissolved in THF (30 mL) and the solution was bubbled with NH$_3$ (gas). A white solid crashed out and the reaction mixture was continued to stir for half an hour. After quenched with brine (20 mL), the mixture was extracted with ethyl acetate (3×20 mL). The combined organic layer was washed with brine, dried over Na$_2$SO$_4$ and concentrated under reduced pressure to afford 1 g (100%) of benzyl 5-carbamoylbicyclo[3.2.1]octan-1-ylcarbamate as a colorless oil, which was used in the next step without purification. ESI-MS m/z: 303 (M+H)$^+$.

Step 3: Benzyl 5-(2-methylpyrimidin-4-ylcarbamoyl)bicyclo[3.2.1]octan-1-ylcarbamate

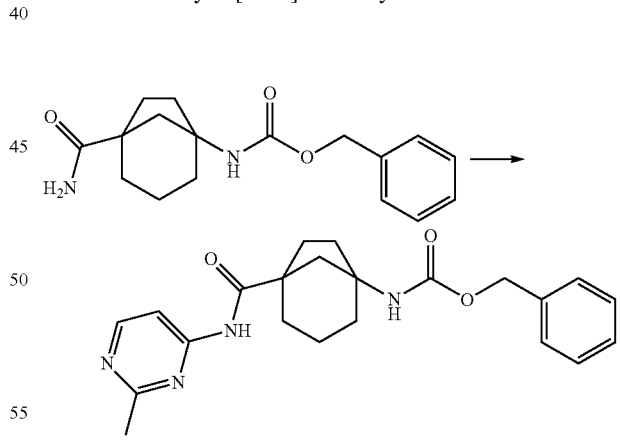

To a mixture of benzyl 5-carbamoylbicyclo[3.2.1]octan-1-ylcarbamate (1 g, 3.3 mmol) and Cs$_2$CO$_3$ (1.6 g, 4.9 mmol) and BINAP (200 mg, 0.3 mmol) in toluene (60 mL), was added 4-chloro-2-methylpyrimidine (430 mg, 3.3 mmol), followed by Pd$_2$(dba)$_3$ (300 mg, 0.32 mmol). The mixture was stirred at 100° C. under N$_2$ overnight. After cooled to room temperature, the reaction mixture was concentrated under reduced pressure and the resulting residue was purified by column chromatography (silica gel, petroleum ether/ethyl acetate: 4/1) to give 1 g (77%) of benzyl 5-(2-methylpyrimidin-4-ylcarbamoyl)bicyclo[3.2.1]octan-1-ylcarbamate as a light yellow oil. ESI-MS m/z: 395 (M+H)⁺.

Step 4: 5-amino-N-(2-methylpyrimidin-4-yl)bicyclo[3.2.1]octane-1-carboxamide

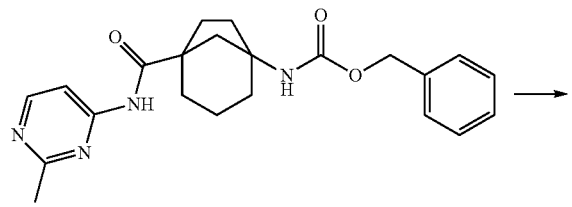

A solution of benzyl 5-(2-methylpyrimidin-4-ylcarbamoyl)bicyclo[3.2.1]octan-1-ylcarbamate (1 g, 2.5 mmol) in HBr/HOAc (33% solution, 8 mL) was stirred at room temperature for an hour and then concentrated under reduced pressure. The resulting residue was dissolved in aq. HCl (6N, 10 mL) and extracted with ethyl acetate (10 mL) to remove the organic impurities. The aqueous phase was basified with aq. NaOH (6N, 4 mL), and then extracted with DCM (4×20 mL). The combined organic layer was washed with brine, dried over Na₂SO₄ and concentrated under reduced pressure to afford 350 mg (66%) of 5-amino-N-(2-methylpyrimidin-4-yl)bicyclo[3.2.1]octane-1-carboxamide as a white solid ESI-MS m/z: 261 (M+H)⁺.

Intermediate 28

5-amino-N-(6-methylpyrazin-2-yl)bicyclo[3.2.1]octane-1-carboxamide

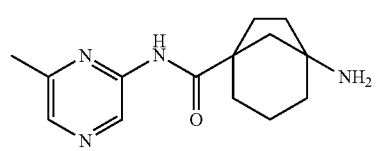 [SMILES: Cc1cncc(NC(=O)C23CCCC(N)(CC2)C3)n1]

In an analogous manner to intermediate 27, 520 mg of intermediate 28 was made. ESI-MS m/z: 261 (M+H)⁺.

Intermediate 29

5-amino-N-pyridin-3-ylbicyclo[3.2.1]octane-1-carboxamide

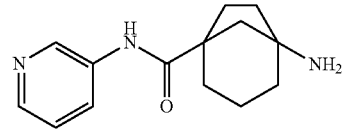 [SMILES: NC12CCCC(C(=O)Nc3cccnc3)(CC1)C2]

In an analogous manner to intermediate 27, 175 mg of intermediate 29 was made. ESI-MS m/z: 246 (M+H)⁺.

Intermediate 30

5-amino-N-pyrazin-2-ylbicyclo[3.2.1]octane-1-carboxamide

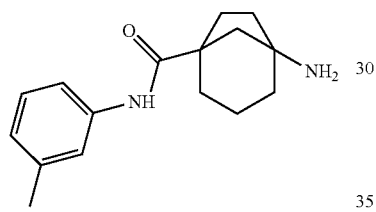

In an analogous manner to intermediate 27, 110 mg of intermediate 30 was made. ESI-MS m/z: 247 (M+H)⁺.

Intermediate 31

5-amino-N-(6-methylpyridin-2-yl)bicyclo[3.2.1]octane-1-carboxamide

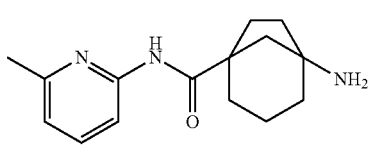 [SMILES: Cc1cccc(NC(=O)C23CCCC(N)(CC2)C3)n1]

In an analogous manner to intermediate 27, 530 mg of intermediate 31 was made. ESI-MS m/z: 260 (M+H)⁺.

3. Preparation of Compounds of the Invention

Unless specified otherwise, all starting materials and reagents were obtained from commercial suppliers, such as Sigma-Aldrich Corp. (St. Louis, Mo., USA) and its subsidiaries, and used without further purification.

Example 1

N,N'-(bicyclo[3.2.1]octane-1,5-diyl)dipicolinamide

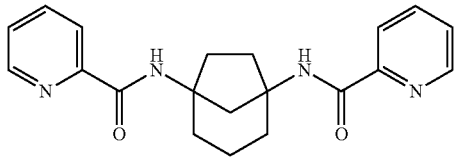 [SMILES: O=C(NC12CCCC(NC(=O)c3ccccn3)(CC1)C2)c1ccccn1]

Example 1 of Table 1 was prepared from intermediate 1 via the process of Scheme 1, supra, as follows:

A mixture of bicyclo[3.2.1]octane-1,5-diamine dihydrochloride (20 mg, 0.094 mmol) and picolinic acid (34.6 mg, 0.28 mmol) in methylene chloride (6 mL) was treated with triethylamine (0.13 mL, 0.94 mmol). The mixture was stirred at rt for a few minutes. N-(3-dimethylaminopropyl)-N'-ethylcarbodiimide hydrochloride (72.0 mg, 0.38 mmol) and 4-dimethylaminopyridine (2.3 mg, 0.02 mmol) were added. The reaction was stirred at rt overnight. The reaction was diluted with a small amount of dichloromethane and washed with water. The organic layer was collected, dried over anhydrous sodium sulfate, filtered, and concentrated under reduced pressure. The resulting residue was purified with chromatography to give 5.4 mg (16%) of the desired product. Analytical data were listed in Table 3.

Example 2 and 3

N-(5-(3-chlorobenzamido)bicyclo[3.2.1]octan-1-yl)-6-methylpicolinamide and N,N'-(bicyclo[3.2.1]octane-1,5-diyl)bis(6-methylpicolinamide)

Example 2

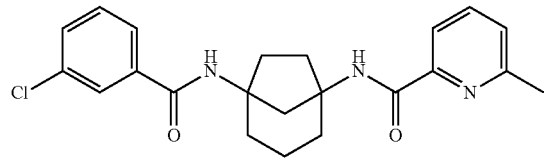

Example 3

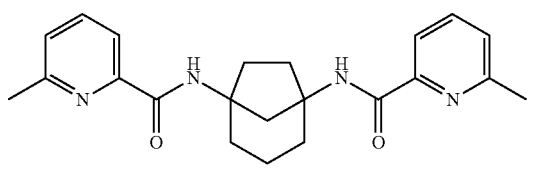

Example 2 and 3 of Table 1 were prepared from intermediate 1 via the process of Scheme 2, supra, as follows:

A mixture of bicyclo[3.2.1]octane-1,5-diamine dihydrochloride (100 mg, 0.469 mmol), 6-methylpicolinic acid (64.3 mg, 0.47 mmol) and 3-chloro-benzoic acid (73.4 mg, 0.47 mmol) in methylene chloride (10 mL, 200 mmol) was treated with triethylamine (0.66 mL, 4.69 mmol). The mixture was stirred for a few minutes. N-(3-Dimethylaminopropyl)-N'-ethylcarbodiimide hydrochloride (360 mg, 1.88 mmol) and 4-dimethylaminopyridine (11.5 mg, 0.0938 mmol) were added. The reaction mixture was stirred at rt overnight. The reaction was diluted with a small amount of dichloromethane and washed with water. The organic layer was dried over anhydrous sodium sulfate, filtered, and concentrated under reduced pressure. The crude material was purified on a reversed phase liquid chromatography/mass spectrometry (RP-HPLC/MS) purification system (Gradient: acetonitrile in water, 25-95% in 3.6 minutes with a cycle time of 5 min. A shallow gradient of 30-58% of acetonitrile was used between 0.75-3.6 min to separate close-eluting impurities. Flow rate: 100 mL/min. Mobile phase additive: 48 mM of ammonium formate. Column: Inertsil® C18, 30×50 mm, 5 um particle size) to afford 3.0 mg (2%) of 6-methyl-pyridine-2-carboxylic acid [5-(3-chloro-benzoylamino)-bicyclo[3.2.1]oct-1-yl]-amide (Example 2) and 7.0 mg (4%) of N,N'-(bicyclo[3.2.1]octane-1,5-diyl)bis(6-methylpicolinamide) (Example 3). Analytical data were listed in Table 3.

Example 4

6-Methyl-pyrazine-2-carboxylic acid {5-[(pyridine-2-carbonyl)-amino]-bicyclo[3.2.1]oct-1-yl}-amide

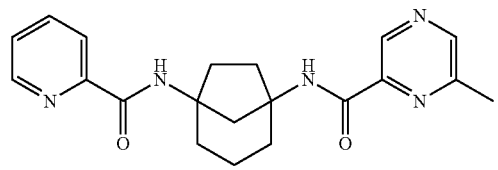 [SMILES: Cc1cncc(C(=O)NC23CCCC(NC(=O)c4ccccn4)(CC2)C3)n1]

Example 4 of Table 1 was prepared from intermediate 2 via the process of Scheme 3, supra, as follows:

A mixture of 6-methyl-pyrazine-2-carboxylic acid (5-amino-bicyclo[3.2.1]oct-1-yl)-amide.ClH (15 mg, 0.05 mmol), picolinic acid (6.2 mg, 0.05 mmol), benzotriazol-1-yloxytris(dimethylamino)phosphonium hexafluorophosphate (22.4 mg, 0.05 mmol) and triethylamine (0.02 mL, 0.15 mmol) in methylene chloride (2.0 mL) was stirred at rt for 2 hours. The mixture was concentrated under reduced pressure, and the resulting residue was purified on a reversed phase liquid chromatography/mass spectrometry (RP-HPLC/MS) purification system (Gradient: acetonitrile in water, 19-95% in 3.5 minutes with a cycle time of 5 min. A shallow gradient between 25-48% of acetonitrile was used between 0.65-3.2 min to separate close-eluting impurities. Flow rate: 100 mL/min. Mobile phase additive: 48 mM of ammonium formate. Column: Inertsil® C18, 30×50 mm, 5 min particle size (GL Sciences)) to afford 8 mg (40%) of the desired product. Analytical data were listed in Table 3.

In an analogous manner to Examples 4, Examples 5-8 of Table 1 were made from commercially available 6-methyl-pyrazine-2-carboxylic acid, 3-fluoro-benzoic acid, 4-fluorobenzoic acid and 2-methyl-pyrimidine-4-carboxylic acid at 0.05-2 mmol reaction scales. Analytical data were listed in Table 3.

Example 98

N-(5-(3-methylbenzamido)bicyclo[3.2.1]octan-1-yl)pyrazine-2-carboxamide

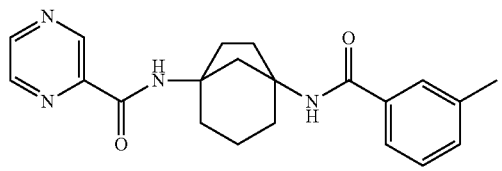 [SMILES: Cc1cccc(C(=O)NC23CCCC(NC(=O)c4cnccn4)(CC2)C3)c1]

Example 98 of Table 1 was prepared from intermediate 9 via the process of Scheme 3, supra, as follows:

To a solution of intermediate 9 (25 mg, 0.11 mmol) and 3-methylbenzoic acid (23 mg, 0.15 mmol) in DMF (5 mL) was added DIPEA (78 mg, 0.66 mmol) and HATU (54 mg, 0.15 mmol). After stirring at room temperature for one hour, water (20 mL) was added and the solution was extracted with ethyl acetate (3×20 mL). The combined organic layer was washed with brine, dried over $Na_2SO_4$, and concentrated under reduced pressure. The resulting residue was purified on a reversed phase liquid chromatography/mass spectrometry (RP-HPLC/MS) purification system (Mobile phase: A) 10 mM $NH_4HCO_3$ in water; B) acetonitrile. Gradient: 32-37% B in 17 min, 37-95% B in 0.2 min, then hold at 95% B for 4 min, back to 10% B in 0.2 min, stop at 24 min. Flow rate: 30 mL/min. Column: Shimadzu pre-ods 20×250 mm, 15 μm, two connected in series) to afford 10 mg (27%) of N-(5-(3-methylbenzamido)bicyclo[3.2.1]octan-1-yl)pyrazine-2-carboxamide as a white solid. Analytical data were listed in Table 3.

In an analogous manner to example 98, examples 9-19, 20-34, 35-48, 49-51, 52-64, 65-79, 80-93, 94-103 and 104-115 of Table 1 were made at 0.1-2 mmol reaction scales from commercially available carboxylic acids and amine intermediates 5, 3, 4, 6, 7, 8, 4, 11, 9 and 10 with yield ranging from 20-80%, respectively. Analytical data were listed in Table 3.

In an analogous manner to example 4, examples 116-121, 122-131, 141-150 and 151-155 of Table 1 were made at 0.1-1 mmol from commercially available carboxylic acids and chiral amine intermediates 22, 21, 23 and 25 with yield ranging from 40-70%, respectively. The absolute stereochemistry of these compounds was arbitrarily assigned. Analytical data were listed in Table 3.

Example 133

6-Methyl-pyrazine-2-carboxylic acid {(1S,5R)-5-[(4-methyl-thiazole-2-carbonyl)-amino]bicyclo[3.2.1]oct-1-yl}-amide

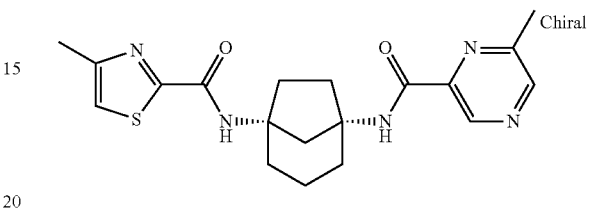

To a solution of {(1R,5S)-5-[(6-methyl-pyrazine-2-carbonyl)-amino]-bicyclo[3.2.1]oct-1-yl}-carbamic acid tert-butyl ester (intermediate 13, 0.050 g, 0.14 mmol) in 1 mL of methylene chloride, 4 M of hydrogen chloride in 1,4-dioxane (0.5 mL) was added. After stirring at rt overnight, the reaction mixture was concentrated under reduced pressure to dryness. The resulting residue was dissolved in methylene chloride (1.0 mL), 4-methyl-1,3-thiazole-2-carboxylic acid (19.8 mg, 0.14 mmol), triethylamine (7.73 μL, 0.56 mmol) and benzotriazol-1-yloxytris(dimethylamino)phosphonium hexafluorophosphate (61.4 mg, 0.14 mmol) were added. After stirring at rt for 1 hour, the reaction mixture was concentrated under reduced pressure. The resulting residue was purified on the CombiFlash® system (hexane/ethyl acetate: 100/0 to 10/90 in 10 mins, then hexane/ethyl acetate: 10/90) to afford 31 mg (58%) of 6-methyl-pyrazine-2-carboxylic acid {(1S,5R)-5-[(4-methyl-thiazole-2-carbonyl)-amino]-bicyclo[3.2.1]oct-1-yl}-amide. Analytical data are listed in Table 3.

In an analogous manner to example 133, examples 132, 134 and 135 of Table 1 were made at ~0.15 mmol reaction scale from intermediate 13 and commercially available carboxylic acids with yield ~60%; examples 136-140 of Table 1 were made at ~0.15 mmol reaction scale from intermediate 12 and commercially available carboxylic acids with yield ~60%. Analytical data were listed in Table 3.

Examples 158 and 159

6-Methyl-pyrazine-2-carboxylic acid {(1R,5S)-5-[(pyridine-2-carbonyl)-amino]-bicyclo[3.2.1]oct-1-yl}-amide and 6-methyl-pyrazine-2-carboxylic acid {(1S,5R)-5-[(pyridine-2-carbonyl)-amino]-bicyclo[3.2.1]oct-1-yl}-amide

158

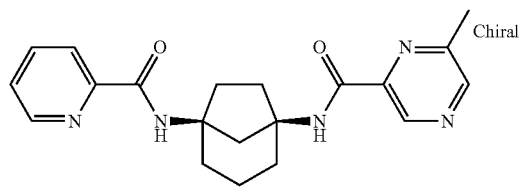

47
-continued

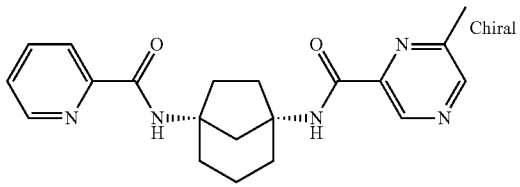

159

Example 8 (0.37 g, 1.0 mmol) was resolved on a chiral HPLC system (column: 30×150 mm OJ (Chiral Technologies Inc). Solvent: EtOH/hexane: 10/90. Detector: UV at 290 nm. Flow rate: 14 mL/min. The front peak was arbitrarily assigned as 6-methyl-pyrazine-2-carboxylic acid {(1R,5S)-5-[(pyridine-2-carbonyl)-amino]-bicyclo[3.2.1]oct-1-yl}-amide (example 158, 56 mg) and the back peak was arbitrarily assigned as 6-methyl-pyrazine-2-carboxylic acid {(1S,5R)-5-[(pyridine-2-carbonyl)-amino]-bicyclo[3.2.1]oct-1-yl}-amide (example 159, 81 mg).

Similarly, examples 156 (31 mg) and 157 (33 mg) of Table 1 were obtained by resolution of example 8, examples 160 (90 mg) and 161 (90 mg) of Table 1 were obtained by resolution of example 6, and examples 162 (50 mg) and 163 (66 mg) of Table 1 were obtained by resolution of example 99, respectively. Analytical data were listed in Table 3.

48

Example 164

6-methyl-N-{5-[(pyridin-2-ylamino)carbonyl]bicyclo[3.2.1]oct-1-yl}pyrazine-2-carboxamide

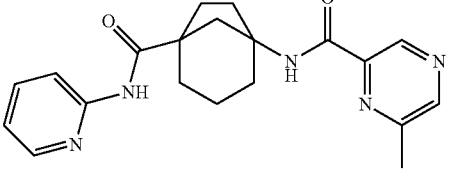

Example 164 of Table 2 was prepared from intermediate 26 via the process of Scheme 4, supra, as follows:

To a solution of 5-(6-methylpyrazine-2-carboxamido)bicyclo[3.2.1]octane-1-carboxylic acid (intermediate 26, 100 mg, 0.35 mmol) and pyridin-2-amine (39 mg, 0.41 mmol) in DMF (5 mL) was added HATU (158 mg, 0.41 mmol) and DIPEA (0.5 mL). After stirring at room temperature for one hour, water (20 mL) was added, and the solution was extracted with ethyl acetate (3×20 mL). The combined organic layer was washed with brine, dried over $Na_2SO_4$, and concentrated under reduced pressure. The resulting residue was purified by column chromatography (silica gel, petroleum ether/ethyl acetate: 2/1) to yield 35 mg (27%) of 6-methyl-N-{5-[(pyridin-2-ylamino)carbonyl]bicyclo[3.2.1]oct-1-yl}pyrazine-2-carboxamide as a white solid. Analytical data were listed in Table 3.

In an analogous manner to example 164, 165-168 of Table 2 was made from intermediate 26 and commercially available heteroaryl amines at ~0.3-0.6 mmol reaction scales. Analytical data were listed in Table 3.

Using the procedure described in the preparation of example 98, examples 169-177, 178-182, 183-185, 186 and 187 of Table 2 were synthesized from commercially available carboxylic acids and amine intermediates 31, 27, 28, 29 and 30, respectively. Analytical data were listed in Table 3.

TABLE 1

Compounds of formula (I-A)

| Example No. | Structure | Chemical Name |
|---|---|---|
| 1 | 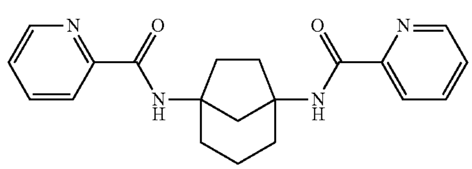 [SMILES: O=C(NC12CCCC(NC(=O)c3ccccn3)(CC1)C2)c1ccccn1] | N,N-bicyclo[3.2.1]octane-1,5-diyl)dipicolinamide |
| 2 | 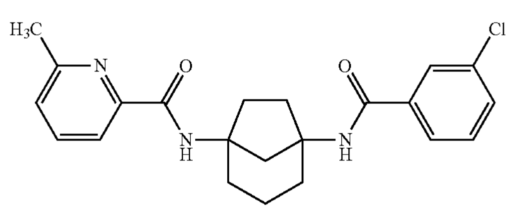 [SMILES: Cc1cccc(C(=O)NC23CCCC(NC(=O)c4cccc(Cl)c4)(CC2)C3)n1] | 6-Methyl-pyridine-2-carboxylic acid [5-(3-chloro-benzoylamino)-bicyclo[3.2.1]oct-1-yl]-amide |

TABLE 1-continued

Compounds of formula (I-A)

| Example No. | Structure | Chemical Name |
|---|---|---|
| 3 | 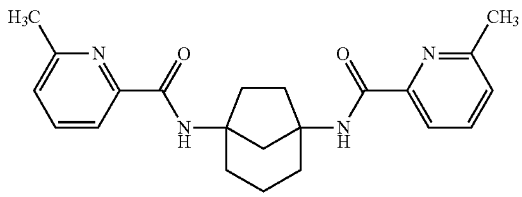 [SMILES: Cc1cccc(C(=O)NC23CCCC(NC(=O)c4cccc(C)n4)(CC2)C3)n1] | N,N-bicyclo[3.2.1]octane-1,5-diyl)bis(6-methylpicolinamide) |
| 4 | 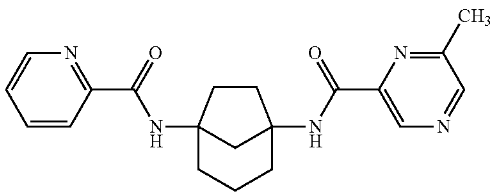 [SMILES: Cc1cncc(C(=O)NC23CCCC(NC(=O)c4ccccn4)(CC2)C3)n1] | 6-Methyl-pyrazine-2-carboxylic acid {5-[(pyridine-2-carbonyl)-amino]-bicyclo[3.2.1]oct-1-yl}-amide |
| 5 | 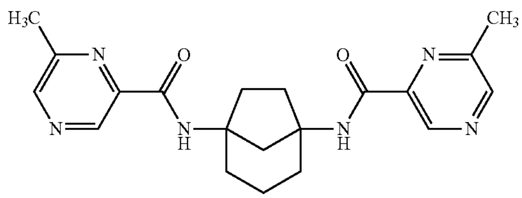 [SMILES: Cc1cncc(C(=O)NC23CCCC(NC(=O)c4cncc(C)n4)(CC2)C3)n1] | N,N-(bicyclo[3.2.1]octane-1,5-diyl)bis(6-methylpyrazine-2-carboxamide) |
| 6 | 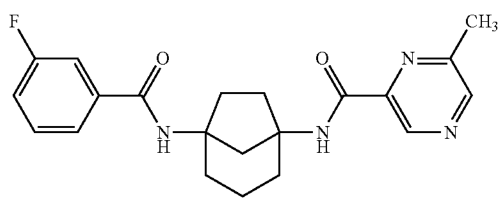 [SMILES: Cc1cncc(C(=O)NC23CCCC(NC(=O)c4cccc(F)c4)(CC2)C3)n1] | 6-Methyl-pyrazine-2-carboxylic acid [5-(3-fluoro-benzoylamino)-bicyclo[3.2.1]oct-1-yl]-amide |
| 7 | 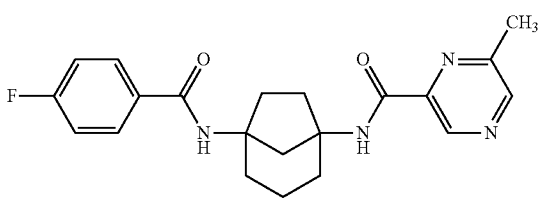 [SMILES: Cc1cncc(C(=O)NC23CCCC(NC(=O)c4ccc(F)cc4)(CC2)C3)n1] | 6-Methyl-pyrazine-2-carboxylic acid [5-(4-fluoro-benzoylamino)-bicyclo[3.2.1]oct-1-yl]-amide |
| 8 | 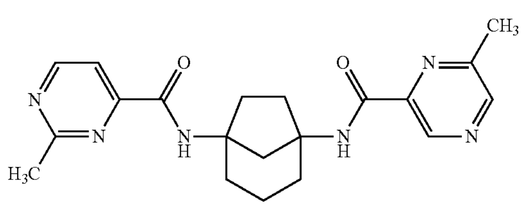 [SMILES: Cc1cncc(C(=O)NC23CCCC(NC(=O)c4ccnc(C)n4)(CC2)C3)n1] | 2-Methyl-pyrimidine-4-carboxylic acid {5-[(6-methyl-pyrazine-2-carbonyl)-amino]-bicyclo[3.2.1]oct-1-yl}-amide |
| 9 | 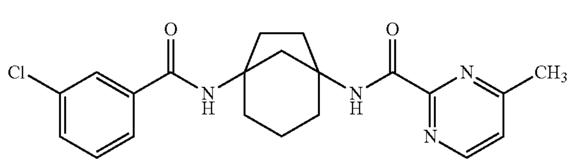 [SMILES: Cc1ccnc(C(=O)NC23CCCC(NC(=O)c4cccc(Cl)c4)(CC2)C3)n1] | N-(5-(3-chlorobenzamido)bicyclo[3.2.1]octan-1-yl)-4-methylpyrimidine-2-carboxamide |
| 10 | 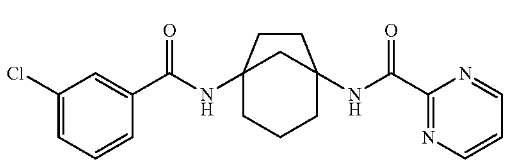 [SMILES: O=C(NC12CCCC(NC(=O)c3ncccn3)(CC1)C2)c1cccc(Cl)c1] | N-(5-(3-chlorobenzamido)bicyclo[3.2.1]octan-1-yl)pyrimidine-2-carboxamide |

TABLE 1-continued

Compounds of formula (I-A)

| Example No. | Structure | Chemical Name |
|---|---|---|
| 11 | 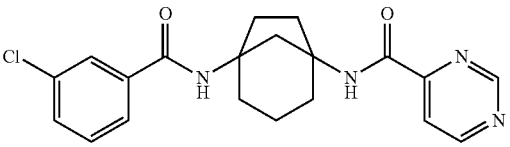 [SMILES: O=C(NC12CCCC(NC(=O)c3ccncn3)(CC1)C2)c1cccc(Cl)c1] | N-(5-(3-chlorobenzamido)bicyclo[3.2.1]octan-1-yl)pyrimidine-4-carboxamide |
| 12 | 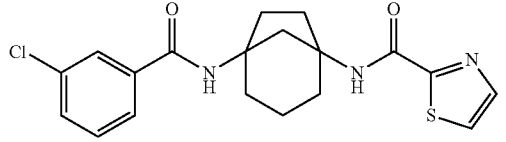 [SMILES: O=C(NC12CCCC(NC(=O)c3nccs3)(CC1)C2)c1cccc(Cl)c1] | N-(5-(3-chlorobenzamido)bicyclo[3.2.1]octan-1-yl)thiazole-2-carboxamide |
| 13 | 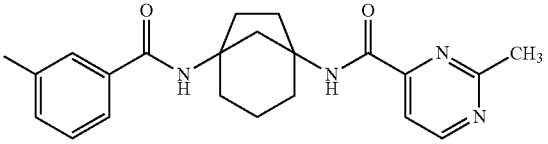 | N-(5-(3-chlorobenzamido)bicyclo[3.2.1]octan-1-yl)-2-methylpyrimidine-4-carboxamide |
| 14 | 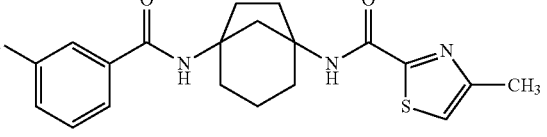 | N-(5-(3-chlorobenzamido)bicyclo[3.2.1]octan-1-yl)-4-methylthiazole-2-carboxamide |
| 15 | 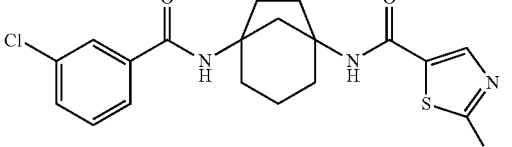 | N-(5-(3-chlorobenzamido)bicyclo[3.2.1]octan-1-yl)-2-methylthiazole-5-carboxamide |
| 16 | 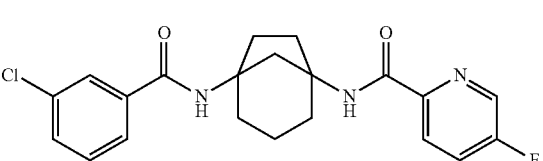 | N-(5-(3-chlorobenzamido)bicyclo[3.2.1]octan-1-yl)-5-fluoropicolinamide |
| 17 | 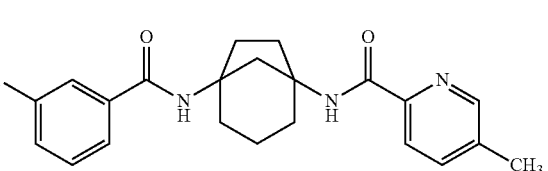 | N-(5-(3-chlorobenzamido)bicyclo[3.2.1]octan-1-yl)-5-methylpicolinamide |
| 18 | 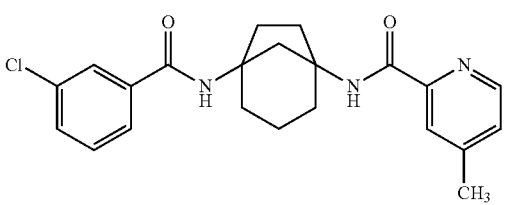 [SMILES: Cc1ccnc(C(=O)NC23CCCC(NC(=O)c4cccc(Cl)c4)(CC2)C3)c1] | N-(5-(3-chlorobenzamido)bicyclo[3.2.1]octan-1-yl)-4-methylpicolinamide |

TABLE 1-continued

Compounds of formula (I-A)

| Example No. | Structure | Chemical Name |
|---|---|---|
| 19 | 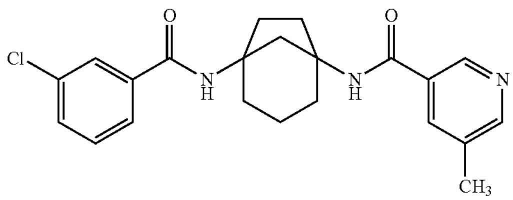 [SMILES: Cc1cncc(C(=O)NC23CCCC(NC(=O)c4cccc(Cl)c4)(CC2)C3)c1] | N-(5-(3-chlorobenzamido)bicyclo[3.2.1]octan-1-yl)-5-methylnicotinamide |
| 20 | 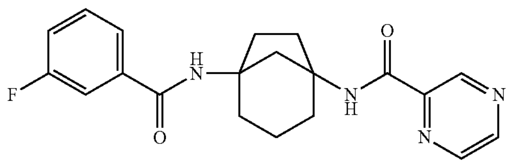 [SMILES: O=C(NC12CCCC(NC(=O)c3cnccn3)(CC1)C2)c1cccc(F)c1] | N-(5-(3-fluorobenzamido)bicyclo[3.2.1]octan-1-yl)pyrazine-2-carboxamide |
| 21 | 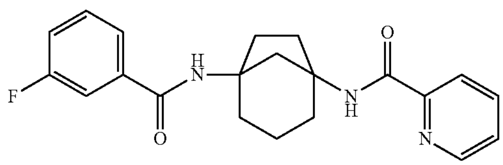 [SMILES: O=C(NC12CCCC(NC(=O)c3ccccn3)(CC1)C2)c1cccc(F)c1] | N-(5-(3-fluorobenzamido)bicyclo[3.2.1]octan-1-yl)picolinamide |
| 22 | 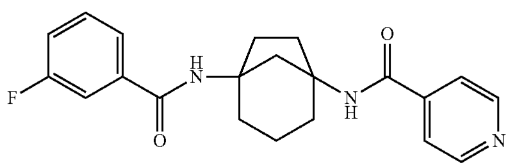 [SMILES: O=C(NC12CCCC(NC(=O)c3cccc(F)c3)(CC1)C2)c1ccncc1] | N-(5-(3-fluorobenzamido)bicyclo[3.2.1]octan-1-yl)isonicotinamide |
| 23 | 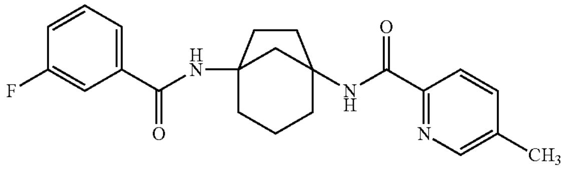 [SMILES: Cc1ccc(C(=O)NC23CCCC(NC(=O)c4cccc(F)c4)(CC2)C3)nc1] | N-(5-(3-fluorobenzamido)bicyclo[3.2.1]octan-1-yl)-5-methylpicolinamide |
| 24 | 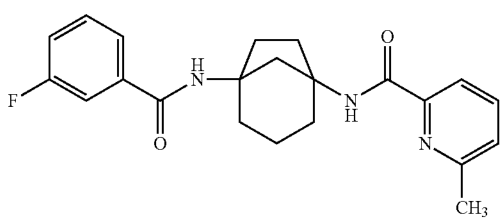 [SMILES: Cc1cccc(C(=O)NC23CCCC(NC(=O)c4cccc(F)c4)(CC2)C3)n1] | N-(5-(3-fluorobenzamido)bicyclo[3.2.1]octan-1-yl)-6-methylpicolinamide |
| 25 | 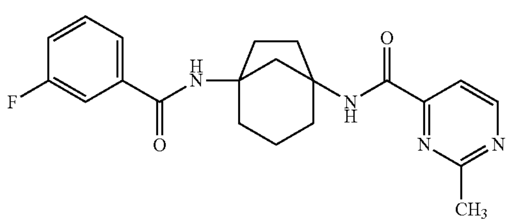 [SMILES: Cc1nccc(C(=O)NC23CCCC(NC(=O)c4cccc(F)c4)(CC2)C3)n1] | N-(5-(3-fluorobenzamido)bicyclo[3.2.1]octan-1-yl)-2-methylpyrimidine-4-carboxamide |
| 26 | 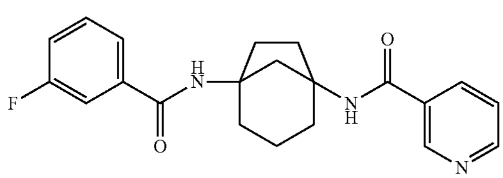 [SMILES: O=C(NC12CCCC(NC(=O)c3cccc(F)c3)(CC1)C2)c1cccnc1] | N-(5-(3-fluorobenzamido)bicyclo[3.2.1]octan-1-yl)nicotinamide |

TABLE 1-continued

Compounds of formula (I-A)

| Example No. | Structure | Chemical Name |
|---|---|---|
| 27 | 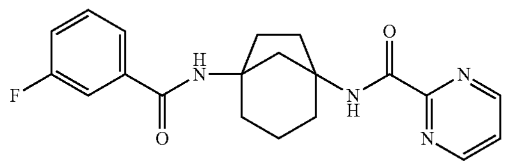 [SMILES: O=C(NC12CCCC(NC(=O)c3ncccn3)(CC1)C2)c1cccc(F)c1] | N-{5-[(3-fluorobenzoyl)amino]bicyclo[3.2.1]oct-1-yl}pyrimidine-2-carboxamide |
| 28 | 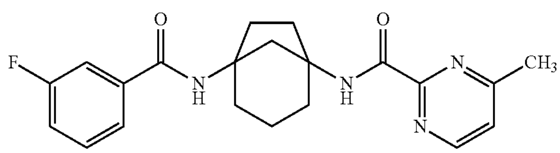 [SMILES: Cc1ccnc(C(=O)NC23CCCC(NC(=O)c4cccc(F)c4)(CC2)C3)n1] | N-(5-(3-fluorobenzamido)bicyclo[3.2.1]octan-1-yl)-4-methylpyrimidine-2-carboxamide |
| 29 | 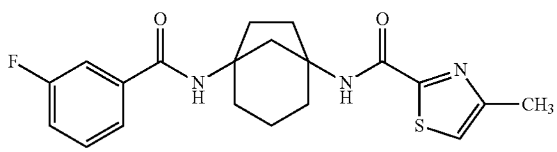 [SMILES: Cc1csc(C(=O)NC23CCCC(NC(=O)c4cccc(F)c4)(CC2)C3)n1] | N-(5-(3-fluorobenzamido)bicyclo[3.2.1]octan-1-yl)-4-methylthiazole-2-carboxamide |
| 30 | 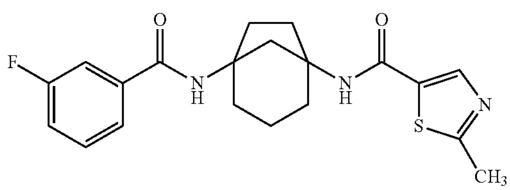 [SMILES: Cc1ncc(C(=O)NC23CCCC(NC(=O)c4cccc(F)c4)(CC2)C3)s1] | N-(5-(3-fluorobenzamido)bicyclo[3.2.1]octan-1-yl)-2-methylthiazole-5-carboxamide |
| 31 | 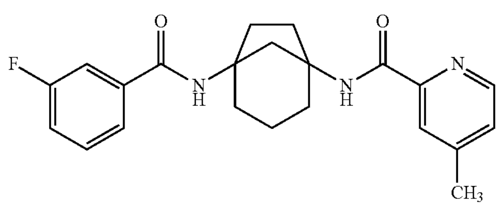 [SMILES: Cc1ccnc(C(=O)NC23CCCC(NC(=O)c4cccc(F)c4)(CC2)C3)c1] | N-(5-(3-fluorobenzamido)bicyclo[3.2.1]octan-1-yl)-4-methylpicolinamide |
| 32 | 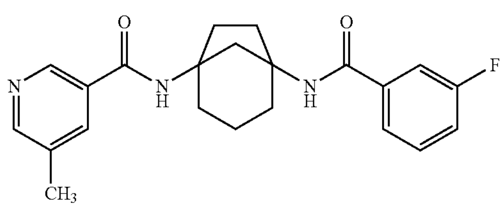 [SMILES: Cc1cncc(C(=O)NC23CCCC(NC(=O)c4cccc(F)c4)(CC2)C3)c1] | N-(5-(3-fluorobenzamido)bicyclo[3.2.1]octan-1-yl)-5-methylnicotinamide |
| 33 | 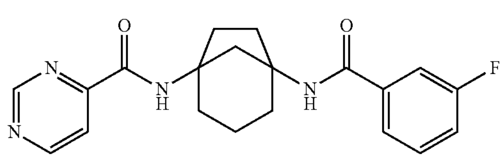 [SMILES: O=C(NC12CCCC(NC(=O)c3ccncn3)(CC1)C2)c1cccc(F)c1] | N-(5-(3-fluorobenzamido)bicyclo[3.2.1]octan-1-yl)pyrimidine-4-carboxamide |
| 34 | 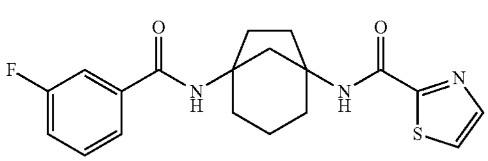 [SMILES: O=C(NC12CCCC(NC(=O)c3nccs3)(CC1)C2)c1cccc(F)c1] | N-(5-(3-fluorobenzamido)bicyclo[3.2.1]octan-1-yl)thiazole-2-carboxamide |

TABLE 1-continued

Compounds of formula (I-A)

| Example No. | Structure | Chemical Name |
|---|---|---|
| 35 | 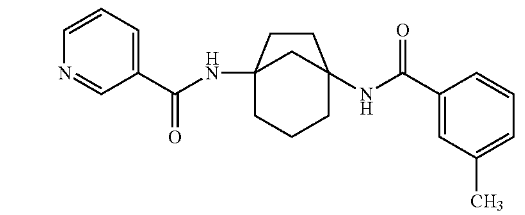 [SMILES: Cc1cccc(C(=O)NC23CCCC(NC(=O)c4cccnc4)(CC2)C3)c1] | N-(5-(3-methylbenzamido)bicyclo[3.2.1]octan-1-yl)nicotinamide |
| 36 | 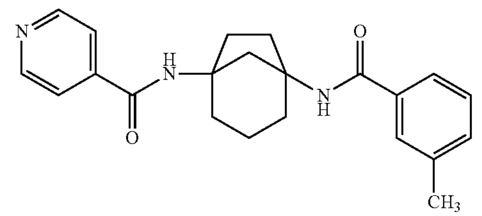 [SMILES: Cc1cccc(C(=O)NC23CCCC(NC(=O)c4ccncc4)(CC2)C3)c1] | N-(5-(3-methylbenzamido)bicyclo[3.2.1]octan-1-yl)isonicotinamide |
| 37 | 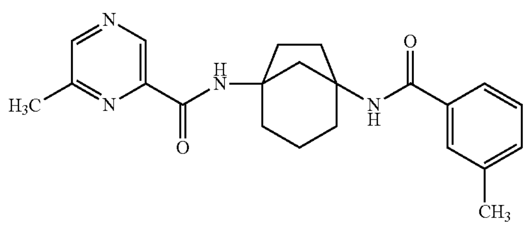 [SMILES: Cc1cccc(C(=O)NC23CCCC(NC(=O)c4cncc(C)n4)(CC2)C3)c1] | 6-methyl-N-(5-(3-methylbenzamido)bicyclo[3.2.1]octan-1-yl)pyrazine-2-carboxamide |
| 38 | 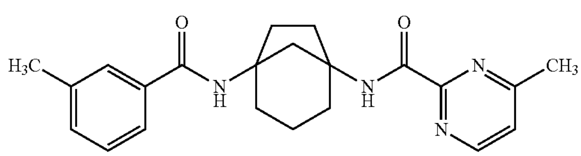 | 4-methyl-N-(5-(3-methylbenzamido)bicyclo[3.2.1]octan-1-yl)pyrazine-2-carboxamide |
| 39 | 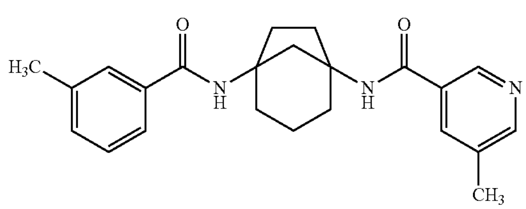 [SMILES: Cc1cccc(C(=O)NC23CCCC(NC(=O)c4cncc(C)c4)(CC2)C3)c1] | 5-methyl-N-(5-(3-methylbenzamido)bicyclo[3.2.1]octan-1-yl)nicotinamide |
| 40 | 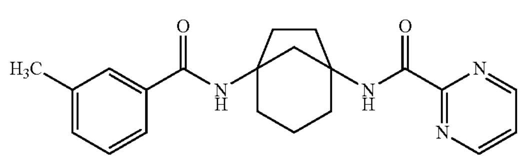 [SMILES: Cc1cccc(C(=O)NC23CCCC(NC(=O)c4ncccn4)(CC2)C3)c1] | N-(5-(3-methylbenzamido)bicyclo[3.2.1]octan-1-yl)pyrimidine-2-carboxamide |
| 41 | 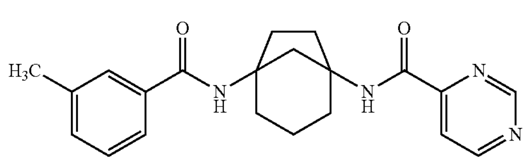 [SMILES: Cc1cccc(C(=O)NC23CCCC(NC(=O)c4ccncn4)(CC2)C3)c1] | N-(5-(3-methylbenzamido)bicyclo[3.2.1]octan-1-yl)pyrimidine-4-carboxamide |
| 42 | 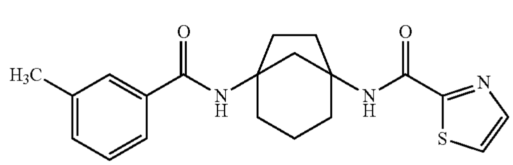 [SMILES: Cc1cccc(C(=O)NC23CCCC(NC(=O)c4nccs4)(CC2)C3)c1] | N-(5-(3-methylbenzamido)bicyclo[3.2.1]octan-1-yl)thiazole-4-carboxamide |

TABLE 1-continued

Compounds of formula (I-A)

| Example No. | Structure | Chemical Name |
|---|---|---|
| 43 | 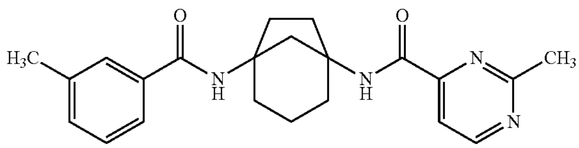 | 2-methyl-N-(5-(3-methylbenzamido)bicyclo[3.2.1]octan-1-yl)pyrimidine-4-carboxamide |
| 44 | 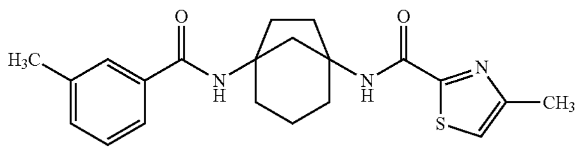 | 4-methyl-N-(5-(3-methylbenzamido)bicyclo[3.2.1]octan-1-yl)thiazole-2-carboxamide |
| 45 | 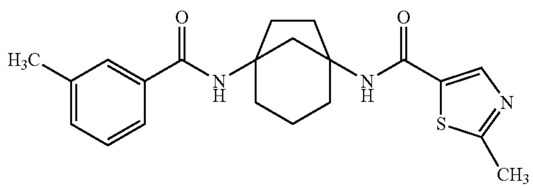 [SMILES: Cc1cccc(C(=O)NC23CCCC(NC(=O)c4cnc(C)s4)(CC2)C3)c1] | 2-methyl-N-(5-(3-methylbenzamido)bicyclo[3.2.1]octan-1-yl)thiazole-5-carboxamide |
| 46 | 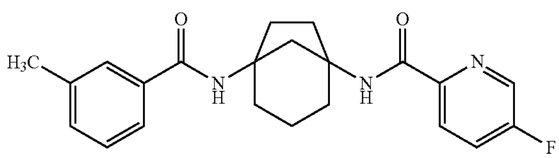 [SMILES: Cc1cccc(C(=O)NC23CCCC(NC(=O)c4ccc(F)cn4)(CC2)C3)c1] | 5-fluoro-N-(5-(3-methylbenzamido)bicyclo[3.2.1]octan-1-yl)picolinamide |
| 47 | 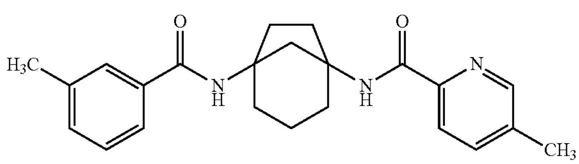 | 5-methyl-N-(5-(3-methylbenzamido)bicyclo[3.2.1]octan-1-yl)picolinamide |
| 48 | 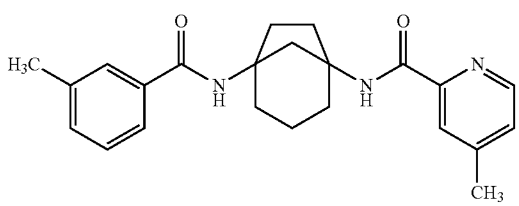 [SMILES: Cc1cccc(C(=O)NC23CCCC(NC(=O)c4cc(C)ccn4)(CC2)C3)c1] | 4-methyl-N-(5-(3-methylbenzamido)bicyclo[3.2.1]octan-1-yl)picolinamide |
| 49 | 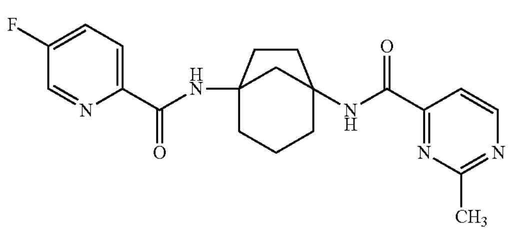 [SMILES: Cc1nccc(C(=O)NC23CCCC(NC(=O)c4ccc(F)cn4)(CC2)C3)n1] | N-(5-(5-fluoropicolinamido)bicyclo[3.2.1]octan-1-yl)-2-methylpyrimidine-4-carboxamide |
| 50 | 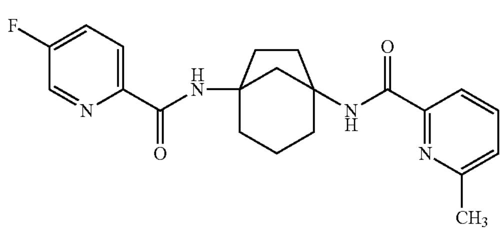 [SMILES: Cc1cccc(C(=O)NC23CCCC(NC(=O)c4ccc(F)cn4)(CC2)C3)n1] | 5-fluoro-N-(5-(6-methylpicolinamido)bicyclo[3.2.1]octan-1-yl)picolinamide |

TABLE 1-continued

Compounds of formula (I-A)

| Example No. | Structure | Chemical Name |
|---|---|---|
| 51 | 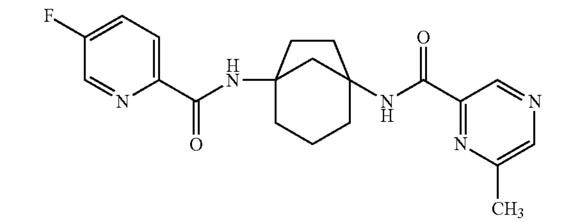 [SMILES: Cc1cncc(C(=O)NC23CCCC(NC(=O)c4ccc(F)cn4)(CC2)C3)n1] | N-(5-(5-fluoropicolinamido)bicyclo[3.2.1]octan-1-yl)-6-methylpyrazine-2-carboxamide |
| 52 | 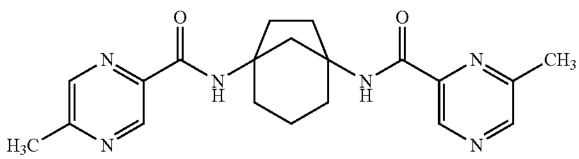 | 5-methyl-N-(5-(6-methylpyrazine-2-carboxamido)bicyclo[3.2.1]octan-1-yl)pyrazine-2-carboxamide |
| 53 | 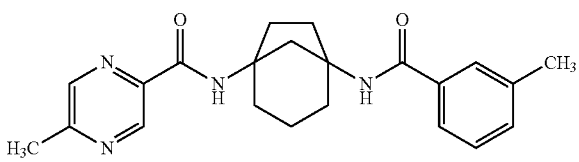 | 5-methyl-N-(5-(3-methylbenzamido)bicyclo[3.2.1]octan-1-yl)pyrazine-2-carboxamide |
| 54 | 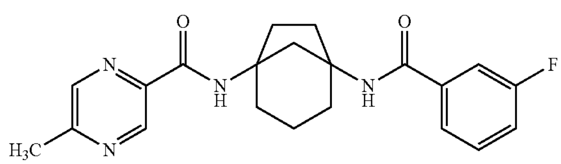 [SMILES: Cc1cnc(C(=O)NC23CCCC(NC(=O)c4cccc(F)c4)(CC2)C3)cn1] | N-(5-(3-fluorobenzamido)bicyclo[3.2.1]octan-1-yl)-5-methylpyrazine-2-carboxamide |
| 55 | 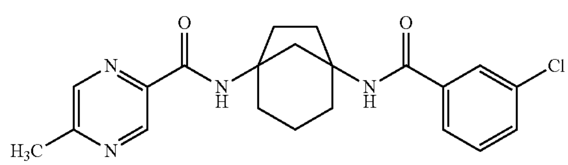 [SMILES: Cc1cnc(C(=O)NC23CCCC(NC(=O)c4cccc(Cl)c4)(CC2)C3)cn1] | N-(5-(3-chlorobenzamido)bicyclo[3.2.1]octan-1-yl)-5-methylpyrazine-2-carboxamide |
| 56 | 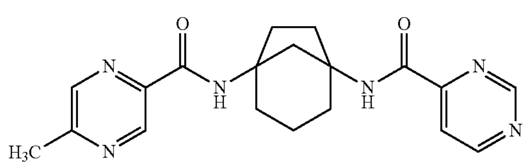 [SMILES: Cc1cnc(C(=O)NC23CCCC(NC(=O)c4ccncn4)(CC2)C3)cn1] | N-(5-{[(5-methylpyrazin-2-yl)carbonyl]amino}bicyclo[3.2.1]oct-1-yl)pyrimidine-4-carboxamide |
| 57 | 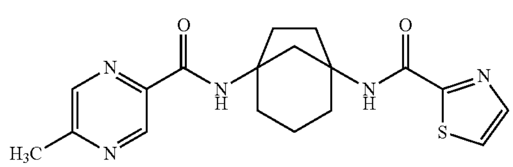 [SMILES: Cc1cnc(C(=O)NC23CCCC(NC(=O)c4nccs4)(CC2)C3)cn1] | N-(5-(5-methylpyrazine-2-carboxamido)bicyclo[3.2.1]octan-1-yl)thiazole-2-carboxamide |
| 58 | 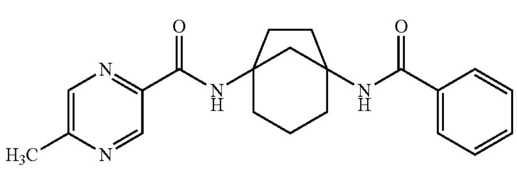 [SMILES: Cc1cnc(C(=O)NC23CCCC(NC(=O)c4ccccc4)(CC2)C3)cn1] | N-(5-benzamidobicyclo[3.2.1]octan-1-yl)-5-methylpyrazine-2-carboxamide |
| 59 | 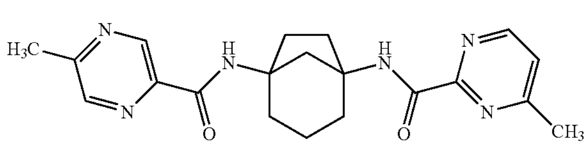 | 4-methyl-N-(5-(5-methylpyrazine-2-carboxamido)bicyclo[3.2.1]octan-1-yl)pyrimidine-2-carboxamide |

TABLE 1-continued

Compounds of formula (I-A)

| Example No. | Structure | Chemical Name |
|---|---|---|
| 60 | 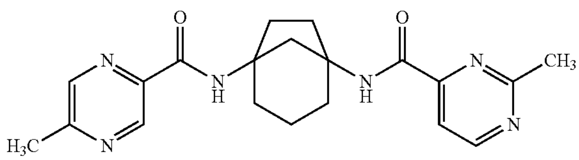 | 2-methyl-N-(5-(5-methylpyrazine-2-carboxamido)bicyclo[3.2.1]octan-1-yl)pyrimidine-4-carboxamide |
| 61 | 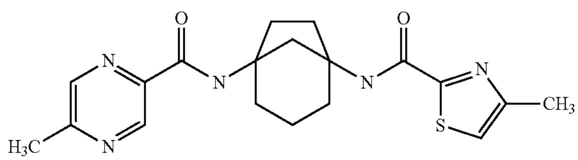 | 5-methyl-N-(5-{[(4-methyl-1,3-thiazol-2-yl)carbonyl]amino}bicyclo[3.2.1]oct-1-yl)pyrazine-2-carboxamide |
| 62 | 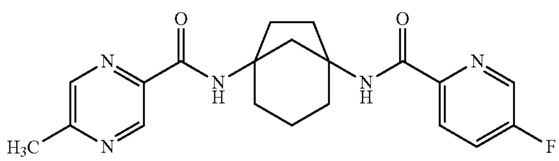 [SMILES: Cc1cnc(C(=O)NC23CCCC(NC(=O)c4ccc(F)cn4)(CC2)C3)cn1] | N-(5-{[(5-fluoropyridin-2-yl)carbonyl]amino}bicyclo[3.2.1]oct-1-yl)-5-methylpyrazine-2-carboxamide |
| 63 | 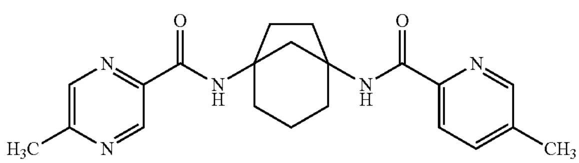 | 5-methyl-N-(5-(5-methylpicolinamido)bicyclo[3.2.1]octan-1-yl)pyrazine-2-carboxamide |
| 64 | 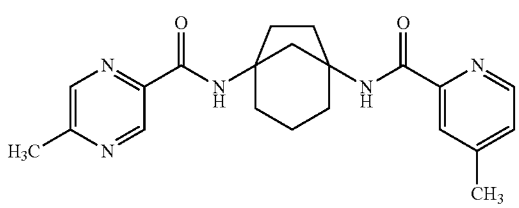 [SMILES: Cc1ccnc(C(=O)NC23CCCC(NC(=O)c4cnc(C)cn4)(CC2)C3)c1] | 5-methyl-N-(5-(4-methylpicolinamido)bicyclo[3.2.1]octan-1-yl)pyrazine-2-carboxamide |
| 65 | 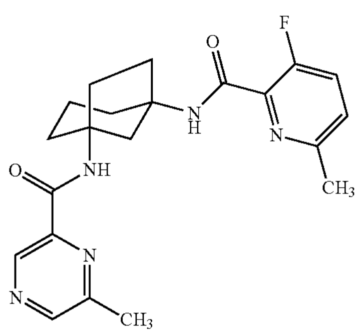 [SMILES: Cc1cncc(C(=O)NC23CCCC(NC(=O)c4nc(C)ccc4F)(CC2)C3)n1] | N-(5-(3-fluoro-6-methylpicolinamido)bicyclo[3.2.1]octan-1-yl)-6-methylpyrazine-2-carboxamide |
| 66 | 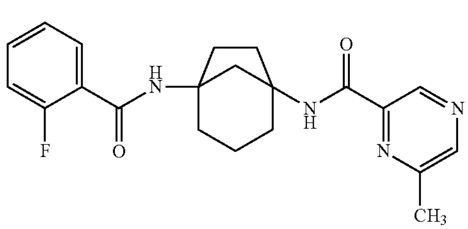 [SMILES: Cc1cncc(C(=O)NC23CCCC(NC(=O)c4ccccc4F)(CC2)C3)n1] | N-(5-(2-fluorobenzamido)bicyclo[3.2.1]octan-1-yl)-6-methylpyrazine-2-carboxamide |

TABLE 1-continued

Compounds of formula (I-A)

| Example No. | Chemical Name |
|---|---|
| 67 | N-(5-(3,5-difluorobenzamido)bicyclo[3.2.1]octan-1-yl)-6-methylpyrazine-2-carboxamide |
| 68 | 6-methyl-N-(5-(nicotinamido)bicyclo[3.2.1]octan-1-yl)pyrazine-2-carboxamide |
| 69 | N-(5-(3-chlorobenzamido)bicyclo[3.2.1]octan-1-yl)-6-methylpyrazine-2-carboxamide |
| 70 | 4-methyl-N-(5-(6-methylpyrazine-2-carboxamido)bicyclo[3.2.1]octan-1-yl)pyrimidine-2-carboxamide |
| 71 | N-(5-(6-methylpyrazine-2-carboxamido)bicyclo[3.2.1]octan-1-yl)pyrimidine-4-carboxamide |
| 72 | N-(5-(6-methylpyrazine-2-carboxamido)bicyclo[3.2.1]octan-1-yl)thiazole-2-carboxamide |
| 73 | N-(5-benzamidobicyclo[3.2.1]octan-1-yl)-6-methylpyrazine-2-carboxamide |
| 74 | 4-methyl-N-(5-(6-methylpyrazine-2-carboxamido)bicyclo[3.2.1]octan-1-yl)thiazole-2-carboxamide |

TABLE 1-continued

Compounds of formula (I-A)

| Example No. | Structure | Chemical Name |
|---|---|---|
| 75 | 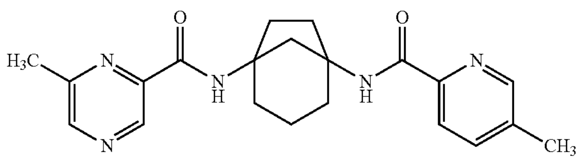 | 6-methyl-N-(5-(5-methylpicolinamido)bicyclo[3.2.1]octan-1-yl)pyrazine-2-carboxamide |
| 76 | 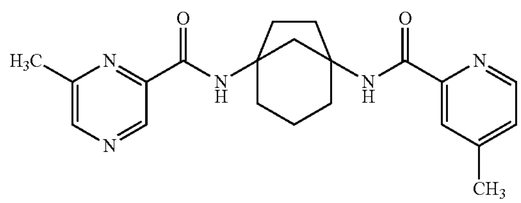 [SMILES: Cc1ccnc(C(=O)NC23CCCC(NC(=O)c4cncc(C)n4)(CC2)C3)c1] | 6-methyl-N-(5-(4-methylpicolinamido)bicyclo[3.2.1]octan-1-yl)pyrazine-2-carboxamide |
| 77 | 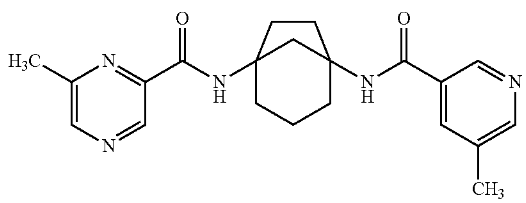 [SMILES: Cc1cncc(C(=O)NC23CCCC(NC(=O)c4cncc(C)n4)(CC2)C3)c1] | 6-methyl-N-(5-(5-methylnicotinamido)bicyclo[3.2.1]octan-1-yl)pyrazine-2-carboxamide |
| 78 | 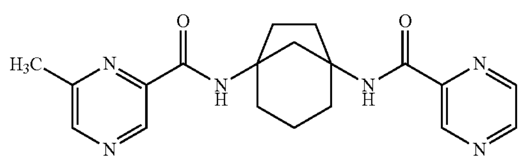 [SMILES: Cc1cncc(C(=O)NC23CCCC(NC(=O)c4cnccn4)(CC2)C3)n1] | 6-methyl-N-(5-(pyrazine-2-carboxamido)bicyclo[3.2.1]octan-1-yl)pyrazine-2-carboxamide |
| 79 | 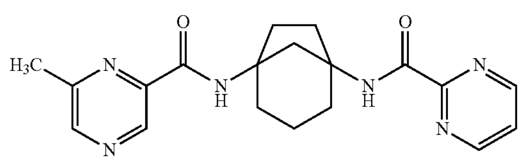 [SMILES: Cc1cncc(C(=O)NC23CCCC(NC(=O)c4ncccn4)(CC2)C3)n1] | N-(5-(6-methylpyrazine-2-carboxamido)bicyclo[3.2.1]octan-1-yl)pyrimidine-2-carboxamide |
| 80 | 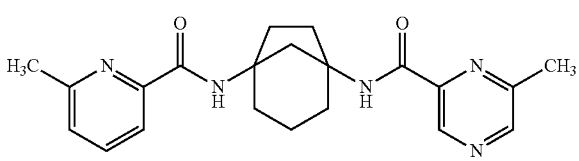 | 6-methyl-N-(5-(6-methylpicolinamido)bicyclo[3.2.1]octan-1-yl)pyrazine-2-carboxamide |
| 81 | 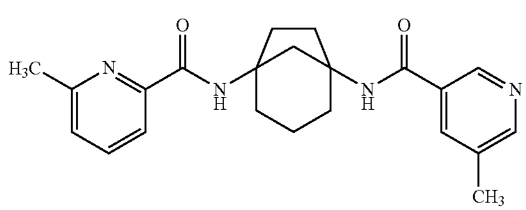 [SMILES: Cc1cncc(C(=O)NC23CCCC(NC(=O)c4cccc(C)n4)(CC2)C3)c1] | 6-methyl-N-(5-(5-methylnicotinamido)bicyclo[3.2.1]octan-1-yl)picolinamide |
| 82 | 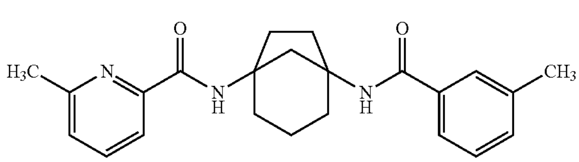 | 6-methyl-N-(5-(3-methylbenzamido)bicyclo[3.2.1]octan-1-yl)picolinamide |

TABLE 1-continued

Compounds of formula (I-A)

| Example No. | Structure | Chemical Name |
|---|---|---|
| 83 | 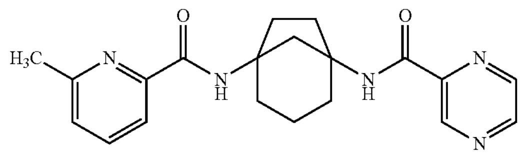 [SMILES: Cc1cccc(C(=O)NC23CCCC(NC(=O)c4cnccn4)(CC2)C3)n1] | N-(5-(6-methylpicolinamido)bicyclo[3.2.1]octan-1-yl)pyrazine-2-carboxamide |
| 84 | 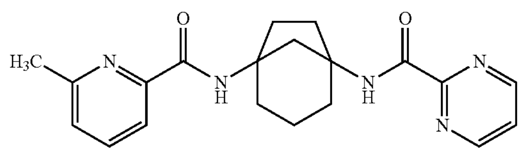 [SMILES: Cc1cccc(C(=O)NC23CCCC(NC(=O)c4ncccn4)(CC2)C3)n1] | N-(5-(6-methylpicolinamido)bicyclo[3.2.1]octan-1-yl)pyrimidine-2-carboxamide |
| 85 | 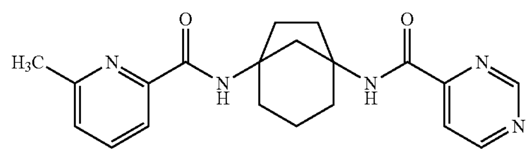 [SMILES: Cc1cccc(C(=O)NC23CCCC(NC(=O)c4ccncn4)(CC2)C3)n1] | N-(5-(6-methylpicolinamido)bicyclo[3.2.1]octan-1-yl)pyrimidine-4-carboxamide |
| 86 | 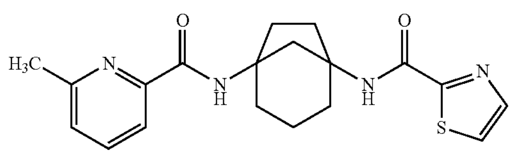 [SMILES: Cc1cccc(C(=O)NC23CCCC(NC(=O)c4nccs4)(CC2)C3)n1] | N-(5-(6-methylpicolinamido)bicyclo[3.2.1]octan-1-yl)thiazole-2-carboxamide |
| 87 | 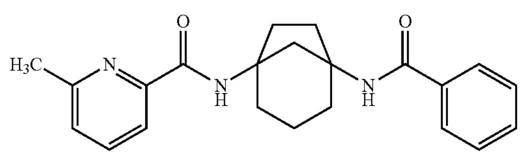 [SMILES: Cc1cccc(C(=O)NC23CCCC(NC(=O)c4ccccc4)(CC2)C3)n1] | N-(5-benzamidobicyclo[3.2.1]octan-1-yl)-6-methylpicolinamide |
| 88 | 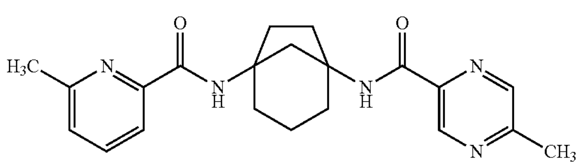 | 5-methyl-N-(5-(6-methylpicolinamido)bicyclo[3.2.1]octan-1-yl)pyrazine-2-carboxamide |
| 89 | 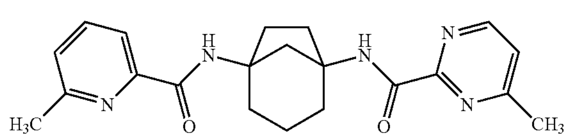 | 4-methyl-N-(5-(6-methylpicolinamido)bicyclo[3.2.1]octan-1-yl)pyrimidine-2-carboxamide |
| 90 | 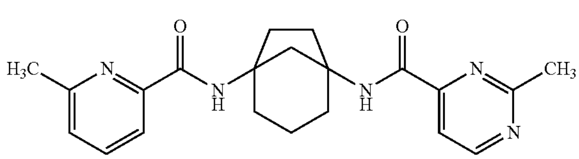 | 2-methyl-N-(5-(6-methylpicolinamido)bicyclo[3.2.1]octan-1-yl)pyrimidine-4-carboxamide |
| 91 | 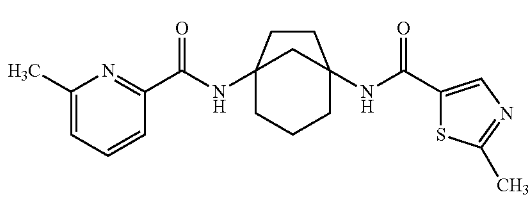 [SMILES: Cc1cccc(C(=O)NC23CCCC(NC(=O)c4cnc(C)s4)(CC2)C3)n1] | 2-methyl-N-(5-(6-methylpicolinamido)bicyclo[3.2.1]octan-1-yl)thiazole-5-carboxamide |

TABLE 1-continued

Compounds of formula (I-A)

| Example No. | Structure | Chemical Name |
|---|---|---|
| 92 | 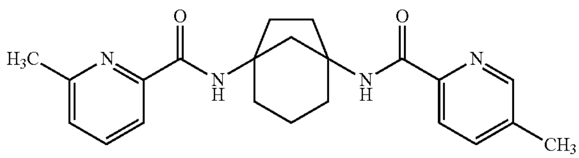 | 6-methyl-N-(5-(5-methylpicolinamido)bicyclo[3.2.1]octan-1-yl)picolinamide |
| 93 | 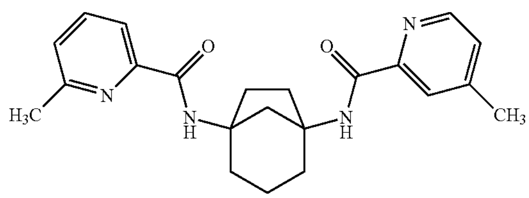 | 6-methyl-N-(5-(4-methylpicolinamido)bicyclo[3.2.1]octan-1-yl)picolinamide |
| 94 | 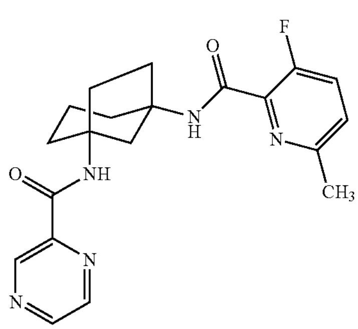 [SMILES: Cc1ccc(F)c(C(=O)NC23CCCC(NC(=O)c4cnccn4)(CC2)C3)n1] | N-(5-(3-fluoro-6-methylpicolinamido)bicyclo[3.2.1]octan-1-yl)pyrazine-2-carboxamide |
| 95 | 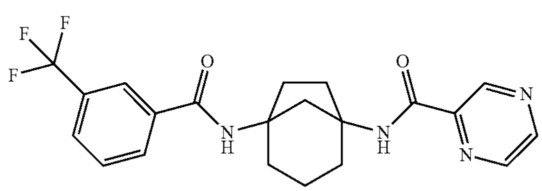 [SMILES: O=C(NC12CCCC(NC(=O)c3cnccn3)(CC1)C2)c1cccc(C(F)(F)F)c1] | Pyrazine-2-carboxylic acid [5-(3-trifluoromethyl-benzoylamino)-bicyclo[3.2.1]oct-1-yl]-amide |
| 96 | 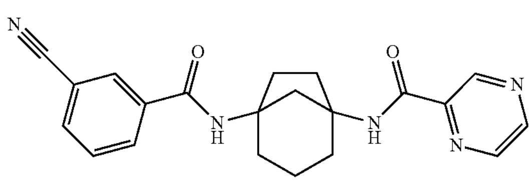 [SMILES: N#Cc1cccc(C(=O)NC23CCCC(NC(=O)c4cnccn4)(CC2)C3)c1] | Pyrazine-2-carboxylic acid [5-(3-cyano-benzoylamino)-bicyclo[3.2.1]oct-1-yl]-amide |
| 97 | 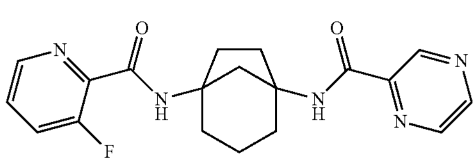 [SMILES: O=C(NC12CCCC(NC(=O)c3ncccc3F)(CC1)C2)c1cnccn1] | Pyrazine-2-carboxylic acid {5-[(3-fluoro-pyridine-2-carbonyl)-amino]-bicyclo[3.2.1]oct-1-yl}-amide |
| 98 | 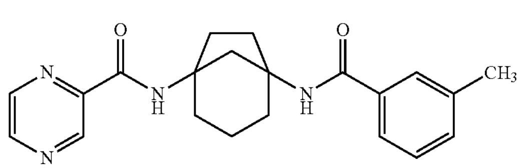 [SMILES: Cc1cccc(C(=O)NC23CCCC(NC(=O)c4cnccn4)(CC2)C3)c1] | N-(5-(3-methylbenzamido)bicyclo[3.2.1]octan-1-yl)pyrazine-2-carboxamide |

TABLE 1-continued

Compounds of formula (I-A)

| Example No. | Structure | Chemical Name |
|---|---|---|
| 99 | 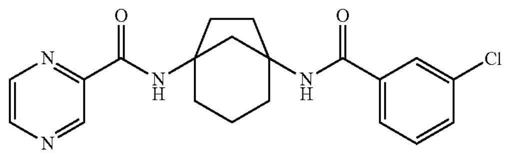 [SMILES: O=C(NC12CCCC(NC(=O)c3cnccn3)(CC1)C2)c1cccc(Cl)c1] | N-(5-(3-chlorobenzamido)bicyclo[3.2.1]octan-1-yl)pyrazine-2-carboxamide |
| 100 | 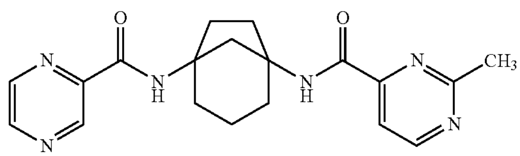 [SMILES: Cc1nccc(C(=O)NC23CCCC(NC(=O)c4cnccn4)(CC2)C3)n1] | 2-methyl-N-(5-(pyrazine-2-carboxamido)bicyclo[3.2.1]octan-1-yl)pyrimidine-4-carboxamide |
| 101 | 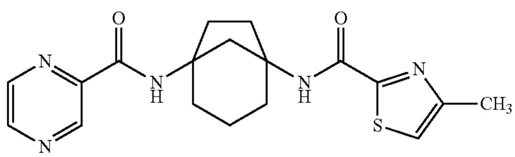 [SMILES: Cc1csc(C(=O)NC23CCCC(NC(=O)c4cnccn4)(CC2)C3)n1] | 4-methyl-N-(5-(pyrazine-2-carboxamido)bicyclo[3.2.1]octan-1-yl)thiazole-2-carboxamide |
| 102 | 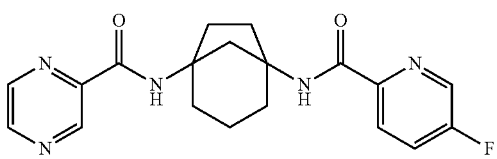 [SMILES: O=C(NC12CCCC(NC(=O)c3cnccn3)(CC1)C2)c1ccc(F)cn1] | N-(5-(5-fluoropicolinamido)bicyclo[3.2.1]octan-1-yl)pyrazine-2-carboxamide |
| 103 | 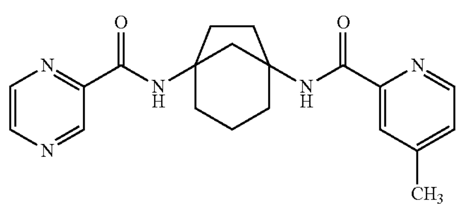 [SMILES: Cc1ccnc(C(=O)NC23CCCC(NC(=O)c4cnccn4)(CC2)C3)c1] | N-(5-(4-methylpicolinamido)bicyclo[3.2.1]octan-1-yl)pyrazine-2-carboxamide |
| 104 | 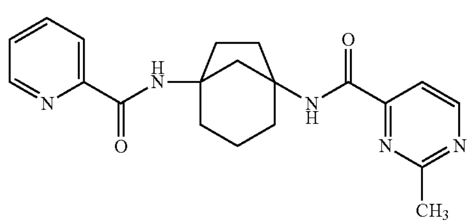 | 2-methyl-N-(5-(picolinamido)bicyclo[3.2.1]octan-1-yl)pyrimidine-4-carboxamide |
| 105 | 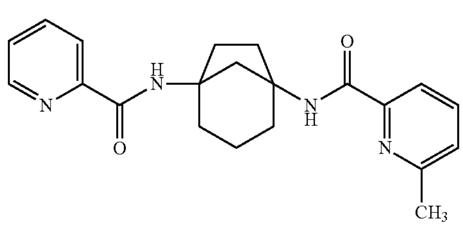 [SMILES: Cc1cccc(C(=O)NC23CCCC(NC(=O)c4ccccn4)(CC2)C3)n1] | 6-methyl-N-(5-(picolinamido)bicyclo[3.2.1]octan-1-yl)picolinamide |
| 106 | 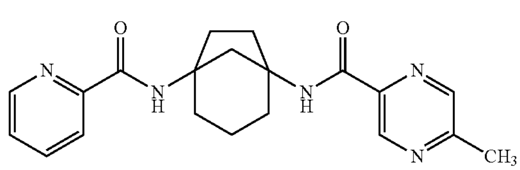 [SMILES: Cc1cnc(C(=O)NC23CCCC(NC(=O)c4ccccn4)(CC2)C3)cn1] | 5-methyl-N-(5-(picolinamido)bicyclo[3.2.1]octan-1-yl)pyrazine-2-carboxamide |

TABLE 1-continued

Compounds of formula (I-A)

| Example No. | Structure | Chemical Name |
|---|---|---|
| 107 | 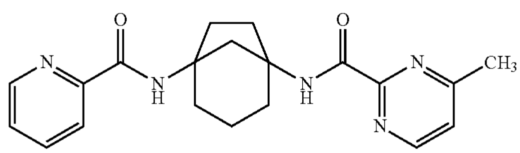 [SMILES: Cc1ccnc(C(=O)NC23CCCC(NC(=O)c4ccccn4)(CC2)C3)n1] | 4-methyl-N-(5-(picolinamido)bicyclo[3.2.1]octan-1-yl)pyrimidine-2-carboxamide |
| 108 | 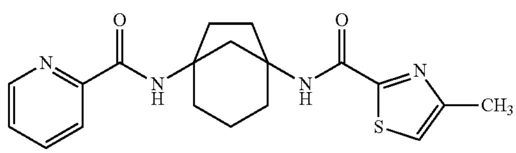 [SMILES: Cc1csc(C(=O)NC23CCCC(NC(=O)c4ccccn4)(CC2)C3)n1] | 4-methyl-N-(5-(picolinamido)bicyclo[3.2.1]octan-1-yl)thiazole-2-carboxamide |
| 109 | 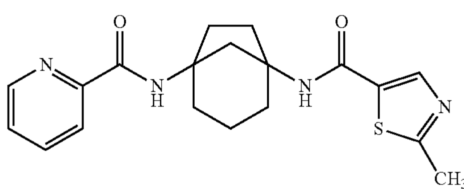 [SMILES: Cc1ncc(C(=O)NC23CCCC(NC(=O)c4ccccn4)(CC2)C3)s1] | 2-methyl-N-(5-(picolinamido)bicyclo[3.2.1]octan-1-yl)thiazole-5-carboxamide |
| 110 | 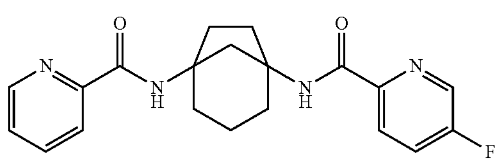 [SMILES: O=C(NC12CCCC(NC(=O)c3ccc(F)cn3)(CC1)C2)c1ccccn1] | 5-fluoro-N-(5-(picolinamido)bicyclo[3.2.1]octan-1-yl)picolinamide |
| 111 | 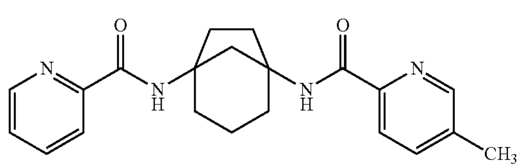 [SMILES: Cc1ccc(C(=O)NC23CCCC(NC(=O)c4ccccn4)(CC2)C3)nc1] | 5-methyl-N-(5-(picolinamido)bicyclo[3.2.1]octan-1-yl)picolinamide |
| 112 | 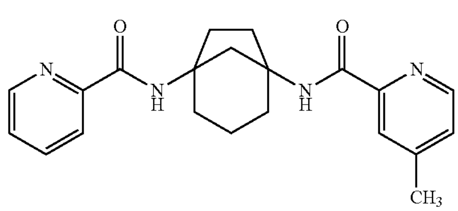 [SMILES: Cc1ccnc(C(=O)NC23CCCC(NC(=O)c4ccccn4)(CC2)C3)c1] | 4-methyl-N-(5-(picolinamido)bicyclo[3.2.1]octan-1-yl)picolinamide |
| 113 | 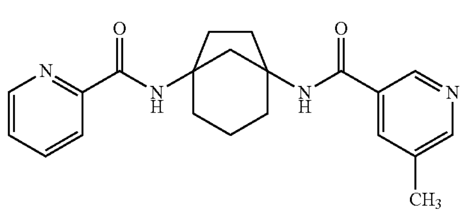 [SMILES: Cc1cncc(C(=O)NC23CCCC(NC(=O)c4ccccn4)(CC2)C3)c1] | N-(5-(5-methylnicotinamido)bicyclo[3.2.1]octan-1-yl)picolinamide |
| 114 | 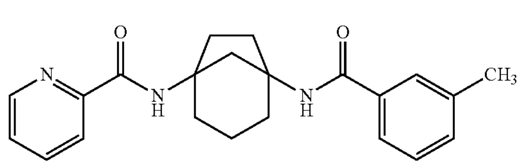 [SMILES: Cc1cccc(C(=O)NC23CCCC(NC(=O)c4ccccn4)(CC2)C3)c1] | N-(5-(3-methylbenzamido)bicyclo[3.2.1]octan-1-yl)picolinamide |

TABLE 1-continued

Compounds of formula (I-A)

| Example No. | Structure | Chemical Name |
|---|---|---|
| 115 | 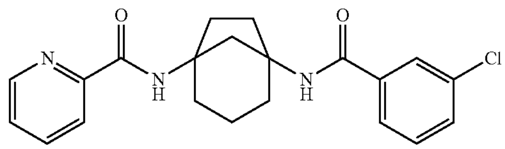 [SMILES: O=C(NC12CCCC(NC(=O)c3ccccn3)(CC1)C2)c1cccc(Cl)c1] | N-(5-(3-chlorobenzamido)bicyclo[3.2.1]octan-1-yl)picolinamide |
| 116 | Chiral | 3-Fluoro-6-methyl-pyridine-2-carboxylic acid {(1S,5R)-5-[(6-methyl-pyridine-2-carbonyl)-amino]-bicyclo[3.2.1]oct-1-yl}-amide |
| 117 | Chiral | 6-Methyl-pyridine-2-carboxylic acid [(1R,5S)-5-(3-fluoro-benzoylamino)-bicyclo[3.2.1]oct-1-yl]-amide |
| 118 | Chiral | 6-Methyl-pyridine-2-carboxylic acid [(1R,5S)-5-(3-methyl-benzoylamino)-bicyclo[3.2.1]oct-1-yl]-amide |
| 119 | Chiral | 6-Methyl-pyridine-2-carboxylic acid {(1R,5S)-5-[(pyridine-2-carbonyl)-amino]-bicyclo[3.2.1]oct-1-yl}-amide |
| 120 | Chiral | 2-Methyl-pyrimidine-4-carboxylic acid {(1S,5R)-5-[(6-methyl-pyridine-2-carbonyl)-amino]-bicyclo[3.2.1]oct-1-yl}-amide |
| 121 | Chiral | Pyrimidine-4-carboxylic acid {(1S,5R)-5-[(6-methyl-pyridine-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 122 | 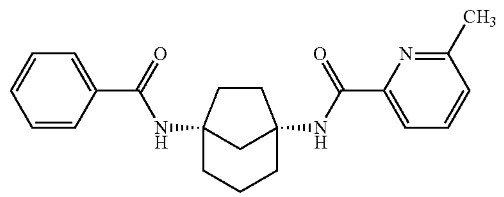 | 6-Methyl-pyridine-2-carboxylic acid ((1S,5R)-5-benzoylamino-bicyclo[3.2.1]oct-1-yl)-amide |
| 123 | 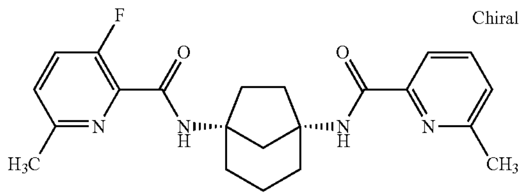 [SMILES: Cc1cccc(C(=O)N[C@@]23CCC[C@@](NC(=O)c4nc(C)ccc4F)(CC2)C3)n1] | 3-Fluoro-6-methyl-pyridine-2-carboxylic acid {(1R,5S)-5-[(6-methyl-pyridine-2-carbonyl)-amino]-bicyclo[3.2.1]oct-1-yl}-amide |
| 124 | 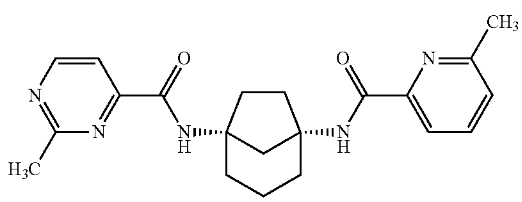 | 2-Methyl-pyrimidine-4-carboxylic acid {(1R,5S)-5-[(6-methyl-pyridine-2-carbonyl)-amino]-bicyclo[3.2.1]oct-1-yl}-amide |
| 125 | 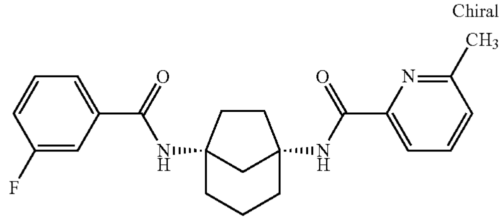 [SMILES: Cc1cccc(C(=O)N[C@@]23CCC[C@@](NC(=O)c4cccc(F)c4)(CC2)C3)n1] | 6-Methyl-pyridine-2-carboxylic acid [(1S,5R)-5-(3-fluoro-benzoylamino)-bicyclo[3.2.1]oct-1-yl]-amide |
| 126 | 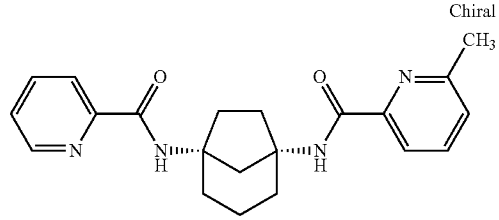 [SMILES: Cc1cccc(C(=O)N[C@@]23CCC[C@@](NC(=O)c4ccccn4)(CC2)C3)n1] | 6-Methyl-pyridine-2-carboxylic acid {(1S,5R)-5-[(pyridine-2-carbonyl)-amino]-bicyclo[3.2.1]oct-1-yl}-amide |
| 127 | 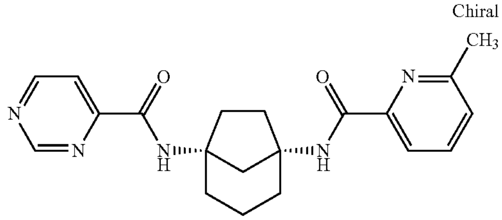 [SMILES: Cc1cccc(C(=O)N[C@@]23CCC[C@@](NC(=O)c4ccncn4)(CC2)C3)n1] | Pyrimidine-4-carboxylic acid {(1R,5S)-5-[(6-methyl-pyridine-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 128 | 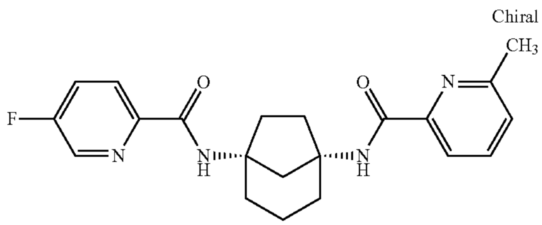 [SMILES: Cc1cccc(C(=O)N[C@@]23CCC[C@@](NC(=O)c4ccc(F)cn4)(CC2)C3)n1] | 5-fluoro-N-((1R,5S)-5-(6-methylpicolinamido)bicyclo[3.2.1]octan-1-yl)picolinamide |
| 129 | 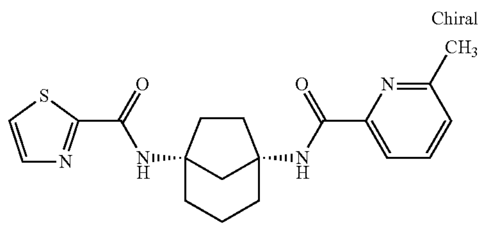 [SMILES: Cc1cccc(C(=O)N[C@@]23CCC[C@@](NC(=O)c4nccs4)(CC2)C3)n1] | 6-Methyl-pyridine-2-carboxylic acid {(1S,5R)-5-[(thiazole-2-carbonyl)-amino]-bicyclo[3.2.1]oct-1-yl}-amide |
| 130 | 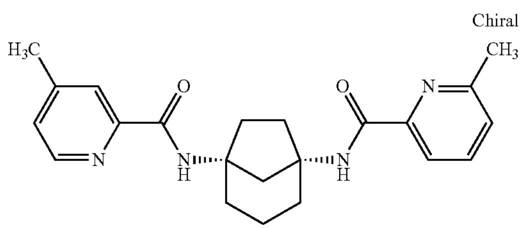 [SMILES: Cc1ccnc(C(=O)N[C@]23CCC[C@](NC(=O)c4cccc(C)n4)(CC2)C3)c1] | 6-methyl-N-((1R,5S)-5-(4-methylpicolinamido)bicyclo[3.2.1]octan-1-yl)picolinamide |
| 131 | 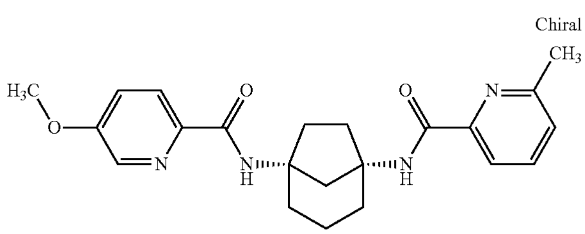 | 5-methoxy-N-((1R,5S)-5-(6-methylpicolinamido)bicyclo[3.2.1]octan-1-yl)picolinamide |
| 132 | 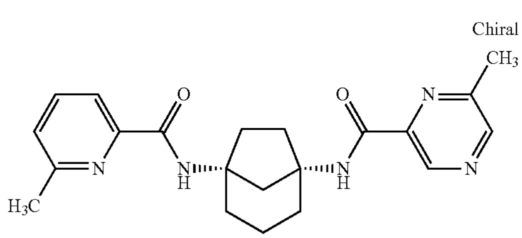 [SMILES: Cc1cncc(C(=O)N[C@@]23CCC[C@@](NC(=O)c4cccc(C)n4)(CC2)C3)n1] | 6-Methyl-pyrazine-2-carboxylic acid {(1S,5R)-5-[(6-methyl-pyridine-2-carbonyl)-amino]-bicyclo[3.2.1]oct-1-yl}-amide |
| 133 | 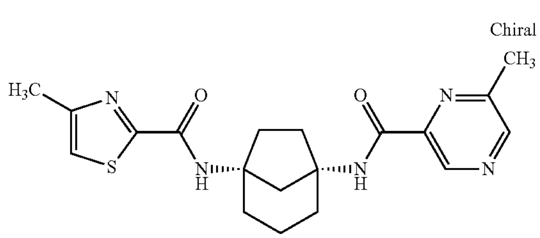 | 6-Methyl-pyrazine-2-carboxylic acid {(1S,5R)-5-[(4-methyl-thiazole-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 134 | 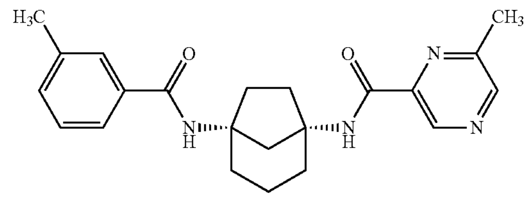 | 6-Methyl-pyrazine-2-carboxylic acid [(1S,5R)-5-(3-methyl-benzoylamino)-bicyclo[3.2.1]oct-1-yl]-amide |
| 135 | 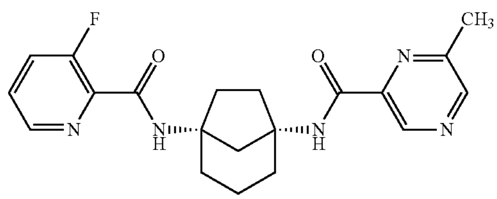 | 6-Methyl-pyrazine-2-carboxylic acid {(1S,5R)-5-[(3-fluoro-pyridine-2-carbonyl)-amino]-bicyclo[3.2.1]oct-1-yl}-amide |
| 136 | 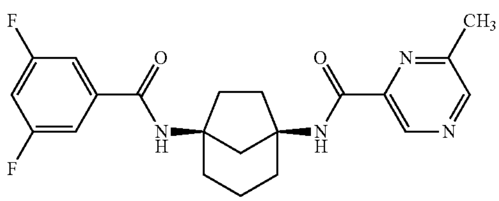 | 6-Methyl-pyrazine-2-carboxylic acid [(1R,5S)-5-(3,5-difluoro-benzoylamino)-bicyclo[3.2.1]oct-1-yl]-amide |
| 137 | 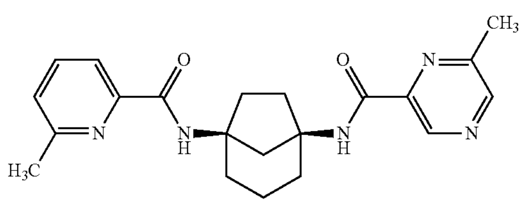 | 6-Methyl-pyrazine-2-carboxylic acid {(1R,5S)-5-[(6-methyl-pyridine-2-carbonyl)-amino]-bicyclo[3.2.1]oct-1-yl}-amide |
| 138 | 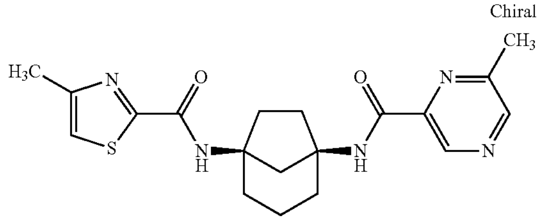 | 6-Methyl-pyrazine-2-carboxylic acid {(1R,5S)-5-[(4-methyl-thiazole-2-carbonyl)-amino]-bicyclo[3.2.1]oct-1-yl}-amide |
| 139 | 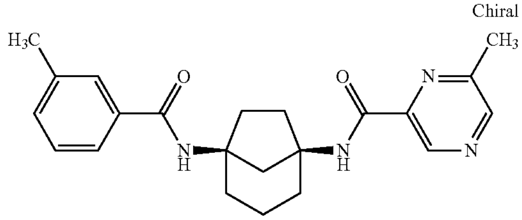 [SMILES: Cc1cccc(C(=O)N[C@@]23CCC[C@@](NC(=O)c4cncc(C)n4)(CC2)C3)c1] | 6-Methyl-pyrazine-2-carboxylic acid [(1R,5S)-5-(3-methyl-benzoylamino)-bicyclo[3.2.1]oct-1-yl]-amide |

TABLE 1-continued

Compounds of formula (I-A)

| Example No. | Structure | Chemical Name |
|---|---|---|
| 140 | 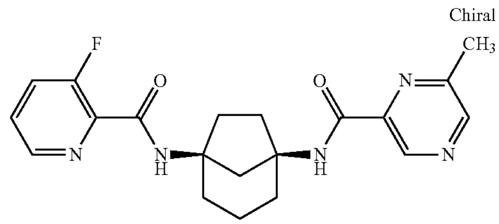 [SMILES: Cc1cncc(C(=O)N[C@]23CCC[C@](NC(=O)c4ncccc4F)(CC2)C3)n1] | 6-Methyl-pyrazine-2-carboxylic acid {(1R,5S)-5-[(3-fluoro-pyridine-2-carbonyl)-amino]-bicyclo[3.2.1]oct-1-yl}-amide |
| 141 | 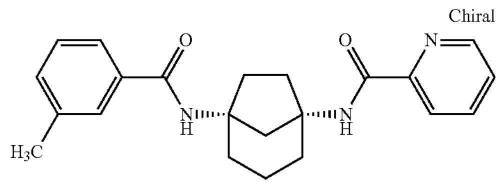 [SMILES: Cc1cccc(C(=O)N[C@]23CCC[C@](NC(=O)c4ccccn4)(CC2)C3)c1] | Pyridine-2-carboxylic acid [(1S,5R)-5-(3-methyl-benzoylamino)-bicyclo[3.2.1]oct-1-yl]-amide |
| 142 | 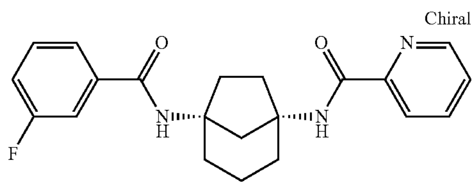 [SMILES: O=C(N[C@]12CCC[C@](NC(=O)c3ccccn3)(CC1)C2)c1cccc(F)c1] | Pyridine-2-carboxylic acid [(1S,5R)-5-(3-fluoro-benzoylamino)-bicyclo[3.2.1]oct-1-yl]-amide |
| 143 | 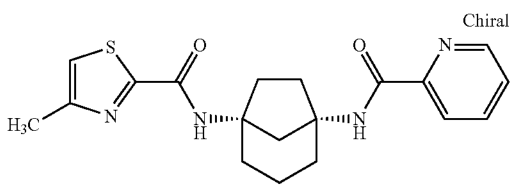 [SMILES: Cc1csc(C(=O)N[C@]23CCC[C@](NC(=O)c4ccccn4)(CC2)C3)n1] | Pyridine-2-carboxylic acid {(1S,5R)-5-[(4-methyl-thiazole-2-carbonyl)-amino]-bicyclo[3.2.1]oct-1-yl}-amide |
| 144 | 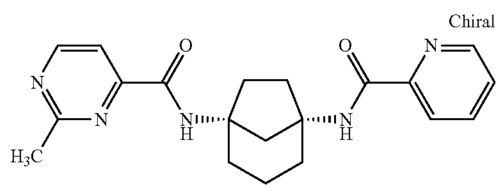 [SMILES: Cc1nccc(C(=O)N[C@]23CCC[C@](NC(=O)c4ccccn4)(CC2)C3)n1] | 2-Methyl-pyrimidine-4-carboxylic acid {(1R,5S)-5-[(pyridine-2-carbonyl)-amino]-bicyclo[3.2.1]oct-1-yl}-amide |
| 145 | 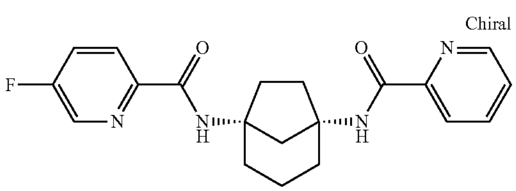 [SMILES: O=C(N[C@@]12CCC[C@@](NC(=O)c3ccc(F)cn3)(CC1)C2)c1ccccn1] | 5-Fluoro-pyridine-2-carboxylic acid {(1R,5S)-5-[(pyridine-2-carbonyl)-amino]-bicyclo[3.2.1]oct-1-yl}-amide |
| 146 | 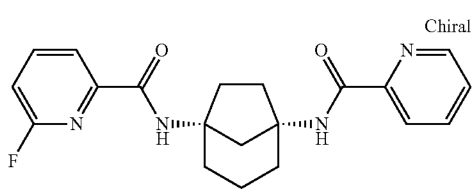 [SMILES: O=C(N[C@@]12CCC[C@@](NC(=O)c3cccc(F)n3)(CC1)C2)c1ccccn1] | 6-Fluoro-pyridine-2-carboxylic acid {(1R,5S)-5-[(pyridine-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 147 | 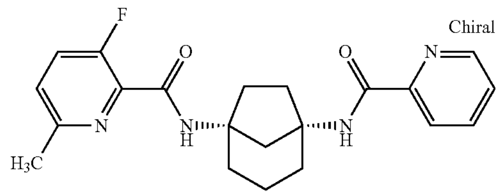 [SMILES: Cc1ccc(F)c(C(=O)N[C@]23CCC[C@](NC(=O)c4ccccn4)(CC2)C3)n1] | 3-Fluoro-6-methyl-pyridine-2-carboxylic acid {(1R,5S)-5-[(pyridine-2-carbonyl)-amino]-bicyclo[3.2.1]oct-1-yl}-amide |
| 148 | 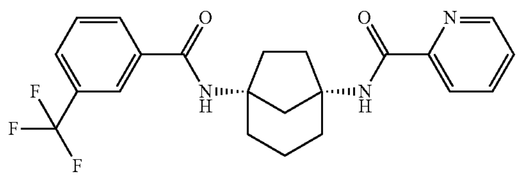 | Pyridine-2-carboxylic acid [(1S,5R)-5-(3-trifluoromethyl-benzoylamino)-bicyclo[3.2.1]oct-1-yl]-amide |
| 149 | 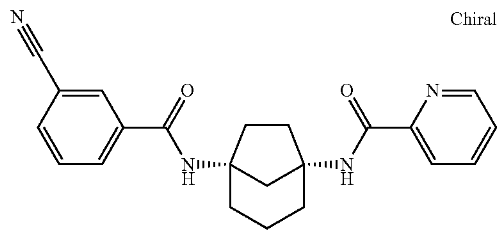 [SMILES: N#Cc1cccc(C(=O)N[C@]23CCC[C@](NC(=O)c4ccccn4)(CC2)C3)c1] | Pyridine-2-carboxylic acid [(1S,5R)-5-(3-cyano-benzoylamino)-bicyclo[3.2.1]oct-1-yl]-amide |
| 150 | 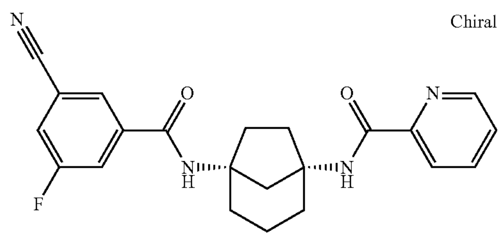 [SMILES: N#Cc1cc(F)cc(C(=O)N[C@]23CCC[C@](NC(=O)c4ccccn4)(CC2)C3)c1] | Pyridine-2-carboxylic acid [(1S,5R)-5-(3-cyano-5-fluoro-benzoylamino)-bicyclo[3.2.1]oct-1-yl]-amide |
| 151 | 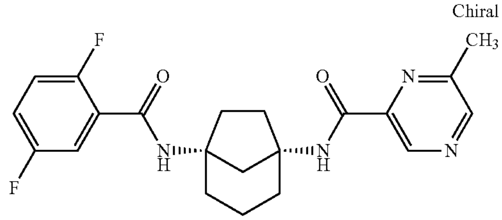 [SMILES: Cc1cncc(C(=O)N[C@@]23CCC[C@@](NC(=O)c4cc(F)ccc4F)(CC2)C3)n1] | 6-Methyl-pyrazine-2-carboxylic acid [(1S,5R)-5-(2,5-difluoro-benzoylamino)-bicyclo[3.2.1]oct-1-yl]-amide |
| 152 | 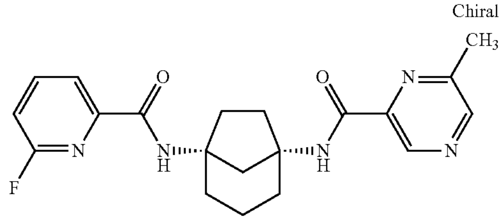 [SMILES: Cc1cncc(C(=O)N[C@@]23CCC[C@@](NC(=O)c4cccc(F)n4)(CC2)C3)n1] | 6-Methyl-pyrazine-2-carboxylic acid {(1S,5R)-5-[(6-fluoro-pyridine-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 153 | 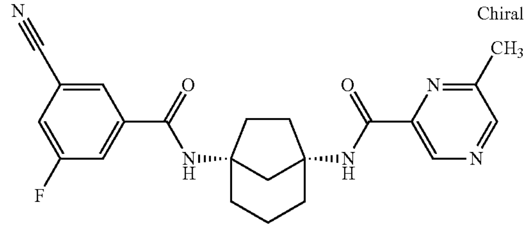 [SMILES: Cc1cncc(C(=O)N[C@@]23CCC[C@@](NC(=O)c4cc(F)cc(C#N)c4)(CC2)C3)n1] | 6-Methyl-pyrazine-2-carboxylic acid [(1S,5R)-5-(3-cyano-5-fluoro-benzoylamino]-bicyclo[3.2.1]oct-1-yl]-amide |
| 154 | 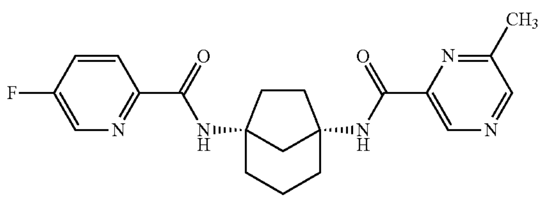 | 6-Methyl-pyrazine-2-carboxylic acid {(1S,5R)-5-[(5-fluoro-pyridine-2-carbonyl)-amino]-bicyclo[3.2.1]oct-1-yl}-amide |
| 155 | 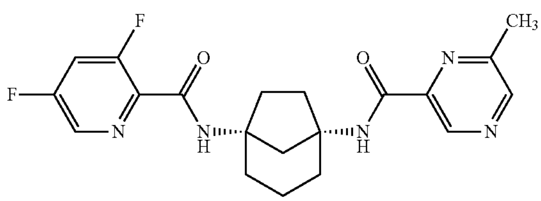 | 6-Methyl-pyrazine-2-carboxylic acid {(1S,5R)-5-[(3,5-difluoro-pyridine-2-carbonyl)-amino]-bicyclo[3.2.1]oct-1-yl}-amide |
| 156 | 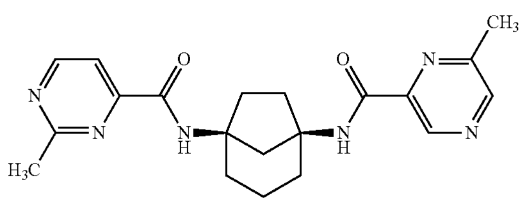 | 2-Methyl-pyrimidine-4-carboxylic acid {(1S,5R)-5-[(6-methyl-pyrazine-2-carbonyl)-amino]-bicyclo[3.2.1]oct-1-yl}-amide |
| 157 | 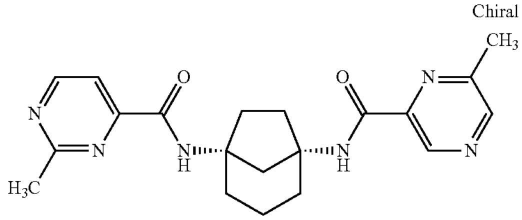 [SMILES: Cc1cncc(C(=O)N[C@@]23CCC[C@@](NC(=O)c4ccnc(C)n4)(CC2)C3)n1] | 2-Methyl-pyrimidine-4-carboxylic acid {(1R,5S)-5-[(6-methyl-pyrazine-2-carbonyl)-amino]-bicyclo[3.2.1]oct-1-yl}-amide |
| 158 | 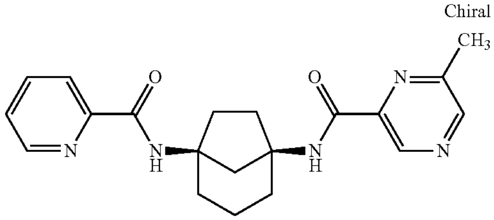 [SMILES: Cc1cncc(C(=O)N[C@]23CCC[C@](NC(=O)c4ccccn4)(CC2)C3)n1] | 6-Methyl-pyrazine-2-carboxylic acid {(1R,5S)-5-[(pyridine-2-carbonyl)-amino]-bicyclo[3.2.1]oct-1-yl}-amide |

TABLE 1-continued

Compounds of formula (I-A)

| Example No. | Structure | Chemical Name |
|---|---|---|
| 159 | 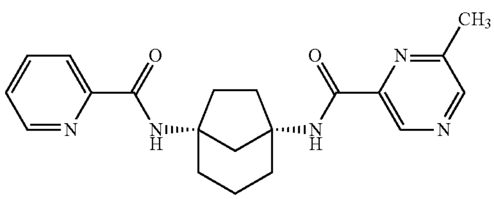 | 6-Methyl-pyrazine-2-carboxylic acid {(1S,5R)-5-[(pyridine-2-carbonyl)-amino]-bicyclo[3.2.1]oct-1-yl}-amide |
| 160 | 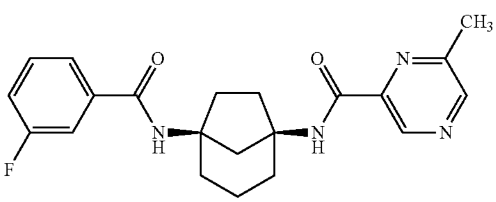 | 6-Methyl-pyrazine-2-carboxylic acid [(1R,5S)-5-(3-fluoro-benzoylamino)-bicyclo[3.2.1]oct-1-yl]-amide |
| 161 | 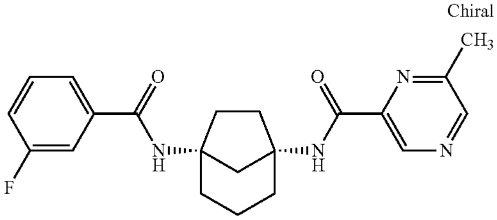 [SMILES: Cc1cncc(C(=O)N[C@@]23CCC[C@@](NC(=O)c4cccc(F)c4)(CC2)C3)n1] | 6-Methyl-pyrazine-2-carboxylic acid [(1S,5R)-5-(3-fluoro-benzoylamino)-bicyclo[3.2.1]oct-1-yl]-amide |
| 162 | 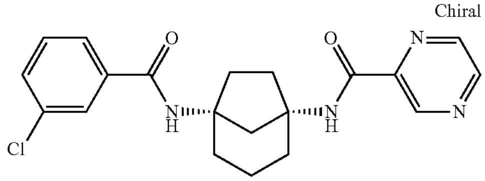 [SMILES: O=C(N[C@]12CCC[C@](NC(=O)c3cnccn3)(CC1)C2)c1cccc(Cl)c1] | Pyrazine-2-carboxylic acid [(1S,5R)-5-(3-chloro-benzoylamino)-bicyclo[3.2.1]oct-1-yl]-amide |
| 163 | 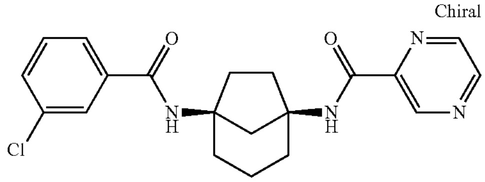 [SMILES: O=C(N[C@@]12CCC[C@@](NC(=O)c3cnccn3)(CC1)C2)c1cccc(Cl)c1] | Pyrazine-2-carboxylic acid [(1R,5S)-5-(3-chloro-benzoylamino)-bicyclo[3.2.1]oct-1-yl]-amide |

TABLE 2

Compounds of formula (I-B)

| Example No. | Structure | Chemical Name |
|---|---|---|
| 164 | 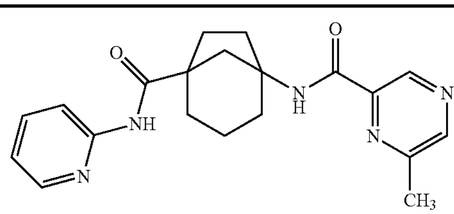 | 6-methyl-N-(5-(pyridin-2-ylcarbamoyl)bicyclo[3.2.1]octan-1-yl)pyrazine-2-carboxamide |

TABLE 2-continued

Compounds of formula (I-B)

| Example No. | Structure | Chemical Name |
|---|---|---|
| 165 | 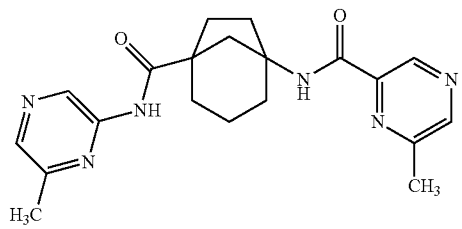 [SMILES: Cc1cncc(NC(=O)C23CCCC(NC(=O)c4cncc(C)n4)(CC2)C3)n1] | 6-methyl-N-(5-(6-methylpyridin-2-ylcarbamoyl)bicyclo[3.2.1]octan-1-yl)pyrazine-2-carboxamide |
| 166 | 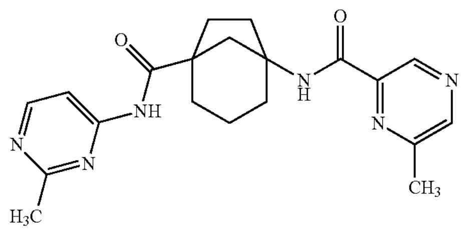 [SMILES: Cc1cncc(C(=O)NC23CCCC(C(=O)Nc4ccnc(C)n4)(CC2)C3)n1] | 6-methyl-N-(5-(2-methylpyrimidin-4-ylcarbamoyl)bicyclo[3.2.1]octan-1-yl)pyrazine-2-carboxamide |
| 167 | 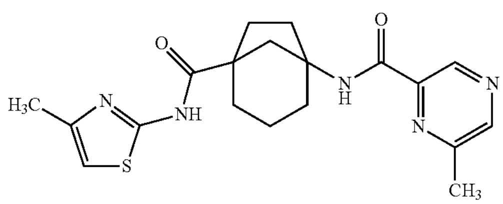 [SMILES: Cc1cncc(C(=O)NC23CCCC(C(=O)Nc4nc(C)cs4)(CC2)C3)n1] | 6-methyl-N-(5-(4-methylthiazole-2-ylcarbamoyl)bicyclo[3.2.1]octan-1-yl)pyrazine-2-carboxamide |
| 168 | 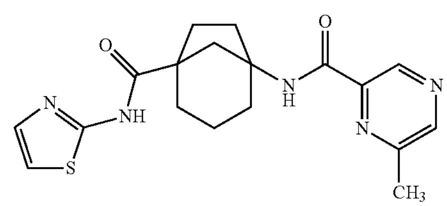 [SMILES: Cc1cncc(C(=O)NC23CCCC(C(=O)Nc4nccs4)(CC2)C3)n1] | 6-methyl-N-(5-(thiazol-2-ylcarbamoyl)bicyclo[3.2.1]octan-1-yl)pyrazine-2-carboxamide |
| 169 | 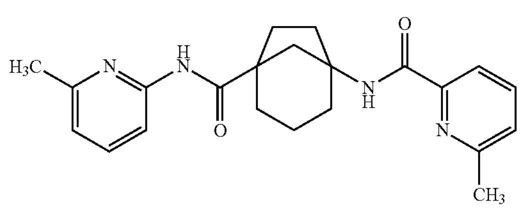 [SMILES: Cc1cccc(NC(=O)C23CCCC(NC(=O)c4cccc(C)n4)(CC2)C3)n1] | 6-methyl-N-(5-(6-methylpyridin-2-ylcarbamoyl)bicyclo[3.2.1]octan-1-yl)picolinamide |
| 170 | 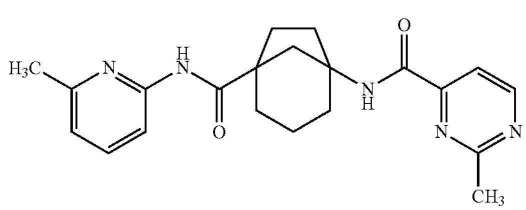 [SMILES: Cc1cccc(NC(=O)C23CCCC(NC(=O)c4ccnc(C)n4)(CC2)C3)n1] | 2-methyl-N-(5-(6-methylpyridin-2-ylcarbamoyl)bicyclo[3.2.1]octan-1-yl)pyrimidine-4-carboxamide |
| 171 | 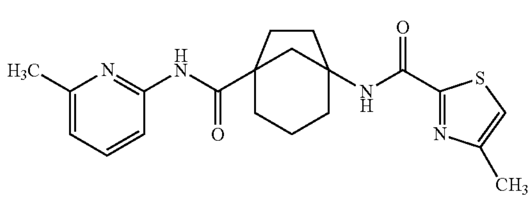 [SMILES: Cc1cccc(NC(=O)C23CCCC(NC(=O)c4nc(C)cs4)(CC2)C3)n1] | 4-methyl-N-(5-(6-methylpyridin-2-ylcarbamoyl)bicyclo[3.2.1]octan-1-yl)thiazole-2-carboxamide |

TABLE 2-continued

Compounds of formula (I-B)

| Example No. | Structure | Chemical Name |
|---|---|---|
| 172 | 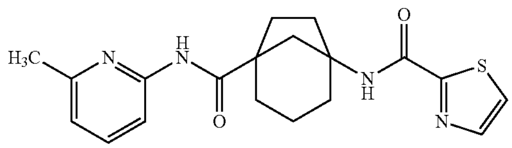 [SMILES: Cc1cccc(NC(=O)C23CCCC(NC(=O)c4nccs4)(CC2)C3)n1] | N-(5-(6-methylpyridin-2-ylcarbamoyl)bicyclo[3.2.1]octan-1-yl)thiazole-2-carboxamide |
| 173 | 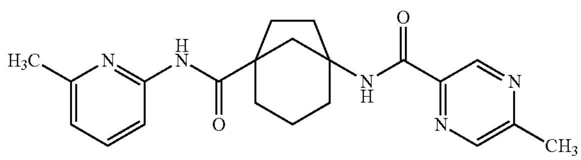 | 5-methyl-N-(5-(6-methylpyridin-2-ylcarbamoyl)bicyclo[3.2.1]octan-1-yl)pyrazine-2-carboxamide |
| 174 | 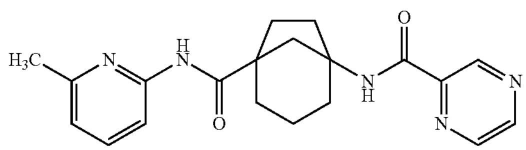 [SMILES: Cc1cccc(NC(=O)C23CCCC(NC(=O)c4cnccn4)(CC2)C3)n1] | N-(5-(6-methylpyridin-2-ylcarbamoyl)bicyclo[3.2.1]octan-1-yl)pyrazine-2-carboxamide |
| 175 | 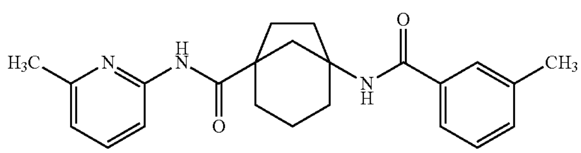 | 5-(3-methylbenzamido)-N-(6-methylpyridin-2-yl)bicyclo[3.2.1]octane-1-carboxamide |
| 176 | 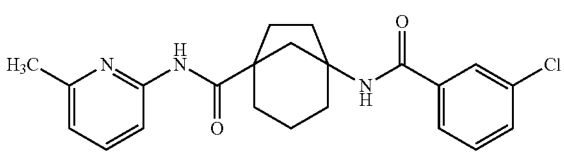 | 5-(3-chlorobenzamido)-N-(6-methylpyridin-2-yl)bicyclo[3.2.1]octane-1-carboxamide |
| 177 | 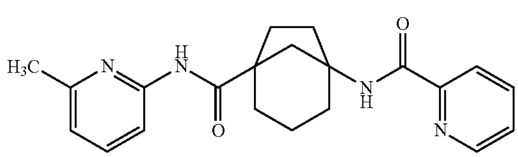 [SMILES: Cc1cccc(NC(=O)C23CCCC(NC(=O)c4ccccn4)(CC2)C3)n1] | N-(5-(6-methylpyridin-2-ylcarbamoyl)bicyclo[3.2.1]octan-1-yl)picolinamide |
| 178 | 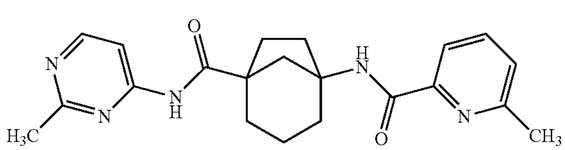 | 6-methyl-N-(5-(2-methylpyrimidin-4-ylcarbamoyl)bicyclo[3.2.1]octan-1-yl)picolinamide |
| 179 | 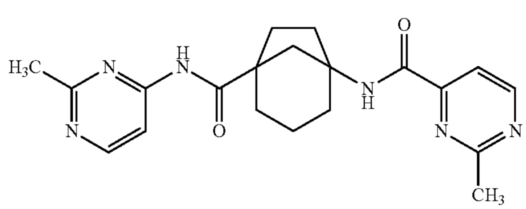 | 2-methyl-N-(5-(2-methylpyrimidin-4-ylcarbamoyl)bicyclo[3.2.1]octan-1-yl)pyrimidine-4-carboxamide |
| 180 | 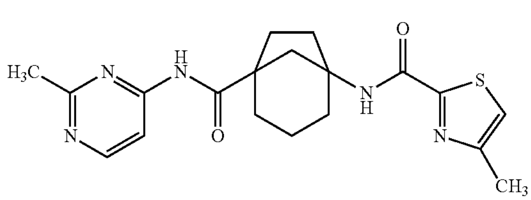 | 4-methyl-N-(5-(2-methylpyrimidin-4-ylcarbamoyl)bicyclo[3.2.1]octan-1-yl)thiazole-2-carboxamide |

TABLE 2-continued

Compounds of formula (I-B)

| Example No. | Structure | Chemical Name |
|---|---|---|
| 181 | 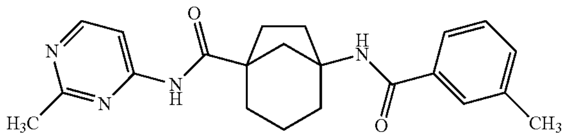 | 5-(3-methylbenzamido)-N-(2-methylpyrimidin-4-yl)bicyclo[3.2.1]octane-1-carboxamide |
| 182 | 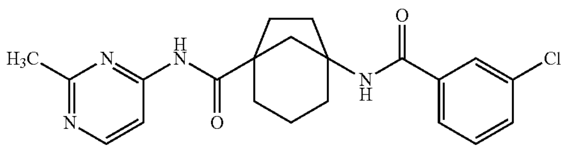 [SMILES: Cc1nccc(NC(=O)C23CCCC(NC(=O)c4cccc(Cl)c4)(CC2)C3)n1] | 5-(3-chlorobenzamido)-N-(2-methylpyrimidin-4-yl)bicyclo[3.2.1]octane-1-carboxamide |
| 183 | 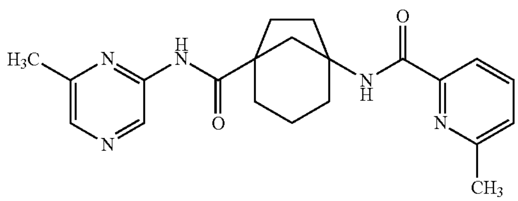 | 6-methyl-N-(5-(6-methylpyrazin-2-ylcarbamoyl)bicyclo[3.2.1]octan-1-yl)picolinamide |
| 184 | 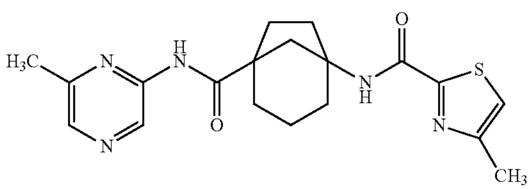 | 4-methyl-N-(5-(6-methylpyrazin-2-ylcarbamoyl)bicyclo[3.2.1]octan-1-yl)thiazole-2-carboxamide |
| 185 | 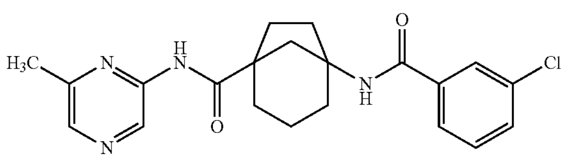 [SMILES: Cc1cncc(NC(=O)C23CCCC(NC(=O)c4cccc(Cl)c4)(CC2)C3)n1] | 5-(3-chlorobenzamido)-N-(6-methylpyrazin-2-yl)bicyclo[3.2.1]octane-1-carboxamide |
| 186 | 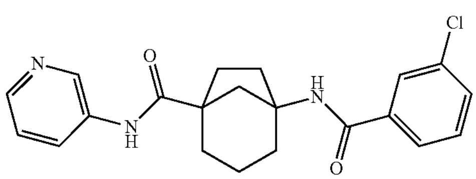 [SMILES: O=C(NC12CCCC(C(=O)Nc3cccnc3)(CC1)C2)c1cccc(Cl)c1] | 5-(3-chlorobenzamido)-N-(pyridin-3-yl)bicyclo[3.2.1]octane-1-carboxamide |
| 187 | 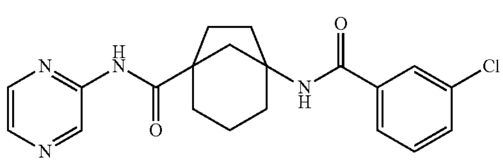 [SMILES: O=C(NC12CCCC(C(=O)Nc3cnccn3)(CC1)C2)c1cccc(Cl)c1] | 5-(3-chlorobenzamido)-N-(pyrazin-2-yl)bicyclo[3.2.1]octane-1-carboxamide |

TABLE 3

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 1 | 8.23 (s, 2H), 8.15-8.19 (m, 2H), 7.81-7.86 (m, 2H), 7.38-7.43 (m, 4H), 2.75-2.80 (m, 1H), 2.05-2.30 (m, 7H), 1.77-1.92 (m, 4H) | 351 |
| 2 | 8.29 (s, 1H), 7.96 (d, J = 8.0 Hz, 2H), 7.69-7.74 (m, 2H), 7.57-7.61 (m, 1H), 7.44-7.48 (m, 1H), 7.36 (t, J = 7.8 Hz, 2H), 7.24-7.28 (m, 1H), 6.17 (s, 1H), 2.72-2.77 (m, 1H), 2.57 (s, 6H), 2.02-2.30 (m, 7H), 1.77-1.90 (m, 4H) | 398 |

TABLE 3-continued

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 3 | 8.31 (s, 2H), 7.97 (d, J = 7.4 Hz, 2H), 7.71 (t, J = 7.7 Hz, 2H), 7.25 (d, J = 7.9 Hz, 2H), 2.75-2.80 (m, 1H), 2.56 (s, 6H), 2.17-2.27 (m, 5H), 2.09-2.15 (m, 2H), 1.77-1.91 (m, 4H) | 379 |
| 4 | 9.17 (s, 1H), 8.57 (s, 1H), 8.51-8.54 (m, 1H), 8.23 (s, 1H), 8.15-8.19 (m, 1H), 8.01 (s, 1H), 7.82-7.87 (m, 1H), 7.39-7.44 (m, 1H), 2.77-2.82 (m, 1H), 2.60 (s, 3H), 2.01-2.35 (m, 7H), 1.76-1.95 (m, 4H) | 366 |
| 5 | 9.18 (s, 2H), 8.60 (s, 2H), 8.00 (s, 2H), 2.77-2.83 (m, 1H), 2.60 (s, 6H), 2.16-2.30 (m, 5H), 2.06-2.12 (m, 2H), 1.77-1.93 (m, 4H) | 381 |
| 6 | 9.17 (s, 1H), 8.60 (s, 1H), 7.99 (s, 1H), 7.36-7.49 (m, 3H), 7.15-7.22 (m, 1H), 6.18 (s, 1H), 2.73-2.78 (m, 1H), 2.60 (s, 3H), 2.01-2.30 (m, 7H), 1.75-1.92 (m, 4H) | 383 |
| 7 | 9.16 (s, 1H), 8.60 (s, 1H), 7.98 (s, 1H), 7.71-7.76 (m, 2H), 7.06-7.13 (m, 2H), 6.18 (s, 1H), 2.73-2.78 (m, 1H), 2.60 (s, 3H), 2.11-2.29 (m, 5H), 2.01-2.09 (m, 2H), 1.75-1.92 (m, 4H) | 383 |
| 8 | 9.18 (s, 1H), 8.85 (d, J = 5.1 Hz, 1H), 8.60 (s, 1H), 8.19 (s, 1H), 8.00 (s, 1H), 7.88 (d, J = 5.0 Hz, 1H), 2.77-2.83 (m, 1H), 2.77 (s, 3H), 2.60 (s, 3H), 2.05-2.29 (m, 7H), 1.75-1.92 (m, 4H) | 381 |
| 9 | 8.67 (d, J = 5.0 Hz, 1H), 8.19 (s, 1H), 7.72 (s, 1H), 7.61 (d, J = 7.0 Hz, 1H), 7.45 (d, J = 8.0 Hz, 1H), 7.35 (t, J = 8.0 Hz, 1H), 7.26-7.25 (m, 1H), 6.26 (s, 1H), 2.72 (m, 1H), 2.61 (s, 3H), 2.21-1.80 (m, 11H) | 399 |
| 10 | 8.86 (d, J = 6.0 Hz, 2H), 8.16 (s, 1H), 7.73 (t, J = 2.0 Hz, 1H), 7.62-7.60 (m, 1H), 7.44-7.41 (m, 2H), 7.35-7.31 (m, 1H), 6.41 (s, 1H), 2.72 (m, 1H), 2.23-1.79 (m, 11H) | 385 |
| 11 | 9.21 (s, 1H), 8.96 (d, J = 5.0 Hz, 1H), 8.13 (s, 1H), 8.08 (dd, J = 5.0 Hz, 1.5 Hz, 1H), 7.70 (s, 1H), 7.59 (d, J = 7.5 Hz, 1H), 7.47-7.45 (m, 1H), 7.36 (t, J = 8.0 Hz, 1H), 6.15 (s, 1H), 2.75 (d, J = 12.5 Hz, 1H), 2.27-1.81 (m, 11H) | 385 |
| 12 | 7.82 (s, 1H), 7.71 (s, 1H), 7.59 (dd, J = 7.5 Hz, 1.5 Hz, 1H), 7.55 (d, J = 3.0 Hz, 1H), 7.44-7.32 (m, 3H), 6.34 (s, 1H), 2.71 (m, 1H), 2.19-2.17 (m, 11H) | 390 |
| 13 | 8.84 (d, J = 6.0 Hz, 1H), 8.17 (s, 1H), 7.87 (d, J = 6.5 Hz, 1H), 7.70 (t, J = 2.0 Hz, 1H), 7.60-7.58 (m, 1H), 7.45-7.27 (m, 2H), 6.27 (s, 1H), 2.77-2.73 (m, 4H), 2.24-1.81 (m, 11H) | 399 |
| 14 | 7.71 (d, J = 2.0 Hz, 1H), 7.60 (d, J = 8.0 Hz, 1H), 7.44 (d, J = 9.0 Hz, 1H), 7.35-7.32 (m, 2H), 7.09 (s, 1H), 6.38 (s, 1H), 2.70 (d, J = 10.5 Hz, 1H), 2.45 (s, 3H), 2.24-1.78 (m, 11H) | 404 |
| 15 | 7.92 (s, 1H), 7.69 (s, 1H), 7.58-7.33 (m, 3H), 6.26 (s, 1H), 6.16 (s, 1H), 2.71-2.66 (m, 4H), 2.19-1.74 (m, 11H) | 404 |
| 16 | 8.36 (d, J = 2.5 Hz, 1H), 8.35-8.17 (m, 1H), 8.03 (s, 1H), 7.70 (s, 1H), 7.59 (d, J = 8.0 Hz, 1H), 7.54-7.50 (m, 1H), 7.44 (d, J = 8.0 Hz, 1H), 7.36-7.33 (m, 1H), 6.28 (s, 1H), 2.73 (d, J = 10.0 Hz, 1H), 2.26-1.75 (m, 11H) | 402 |
| 17 | 8.33 (s, 1H), 8.14 (s, 1H), 8.04 (d J = 8.0 Hz, 1H), 7.71 (t, J = 2.0 Hz, 1H), 7.63-7.58 (m, 2H), 7.45-7.43 (m, 1H), 7.36-7.33 (m, 1H), 6.25 (s, 1H), 2.73 (d, J = 10.0 Hz, 1H), 2.39 (s, 3H), 2.19-1.77 (m, 11H) | 398 |
| 18 | 8.37 (d, J = 6.0 Hz, 1H), 8.20 (s, 1H), 7.96 (s, 1H), 7.71 (d, J = 2.5 Hz, 1H), 7.60-7.58 (m, 1H), 7.47-7.20 (m, 3H), 6.33 (s, 1H), 2.73-2.69 (m, 1H), 2.40 (s, 3H), 2.28-1.80 (m, 11H) | 398 |
| 19 | 8.71 (s, 1H), 8.49 (s, 1H), 7.84 (s, 1H), 7.60 (t, J = 2.0 Hz, 1H), 7.58 (t, J = 2.0 Hz, 1H), 7.44-7.30 (m, 2H), 6.49 (s, 1H), 6.39 (s, 1H), 2.70 (m, 1H), 2.35 (s, 3H), 2.21-1.80 (m, 11H) | 398 |
| 20 | 9.38 (s, 1H), 8.74 (d, J = 2.5 Hz, 1H), 8.50 (t, J = 2.0 Hz, 1H), 7.94 (s, 1H), 7.47-7.37 (m, 3H), 7.20-7.18 (m, 1H), 6.17 (s, 1H), 2.76-2.73 (m, 1H), 2.25-2.13 (m, 5H), 2.06-2.01 (m, 2H), 1.89-1.81 (m, 4H) | 369 |
| 21 | 8.53 (d, J = 4.5 Hz, 1H), 8.21 (s, 1H), 8.16 (d, J = 8.0 Hz, 1H), 7.84 (t, J = 8.0 Hz, 1H), 7.47-7.37 (m, 4H), 7.18 (t, J = 1.5 Hz, 1H), 6.19 (s, 1H), 2.76-2.74 (m, 1H), 2.30-1.80 (m, 11H) | 368 |
| 22 | 8.75 (s, 2H), 7.61 (s, 2H), 7.47-7.38 (m, 3H), 7.21-7.19 (m, 1H), 6.26 (s, 1H), 6.13 (s, 1H), 2.75-2.73 (m, 1H), 2.25-1.83 (m, 11H) | 368 |
| 23 | 8.34 (s, 1H), 8.16 (s, 1H), 8.05 (d, J = 8.0 Hz, 1H), 7.63-7.45 (m, 2H), 7.41-7.38 (m, 1H), 7.18 (m, 1H), 6.25 (s, 1H), 2.74 (m, 1H), 2.40 (s, 3H), 2.34-2.25 (m, 1H), 2.21-1.78 (m, 10H) | 382 |
| 24 | 8.36 (s, 1H), 7.98 (d, J = 8.0 Hz, 1H), 7.72 (t, J = 7.5 Hz, 1 H), 7.48-7.39 (m, 3H), 7.28-7.26 (m, 1H), 7.19 (t, J = 1.0 Hz, 1H), 6.19 (s, 1H), 2.76-2.74 (m, 1H), 2.58 (s, 3H), 2.32-2.18 (m, 5H), 2.09-2.06 (m, 2H), 1.86-1.82 (m, 4H) | 382 |
| 25 | 8.77 (d, J = 5.0 Hz, 1H), 8.10 (s, 1H), 7.80 (d, J = 5.0 Hz, 1H), 7.40-7.29 (m, 3H), 7.12-7.09 (m, 1H), 6.15 (s, 1H), 2.70-2.66 (m, 4H), 2.17-1.72 (m, 11H) | 383 |
| 26 | 8.94 (s, 1H), 8.72 (d, J = 3.5 Hz, 1H), 8.08-8.06 (m, 1H), 7.47-7.37 (m, 4H), 7.20-7.18 (m, 1H), 6.23 (s, 1H), 6.16 (s, 1H), 2.74-2.71 (m, 1H), 2.24-2.13 (m, 5H), 2.05-2.00 (m, 2H), 1.87-1.79 (m, 4H) | 368 |
| 27 | 8.87 (d, J = 4.5 Hz, 2H), 8.18 (s, 1H), 7.50-7.38 (m, 4H), 7.21-7.18 (m, 1H), 6.24 (s, 1H), 2.74-2.71 (m, 1H), 2.27-2.15 (m, 5H), 2.09-2.04 (m, 2H), 1.92-1.67 (m, 4H) | 369 |
| 28 | 8.67 (d, J = 8.0 Hz, 1H), 8.19 (s, 1H), 7.50-7.47 (m, 2H), 7.39-7.35 (m, 1H), 7.27-7.25 (m, 1H), 7.18-7.14 (m, 1H), 6.38 (s, 1H), 2.71 (d, J = 10.0 Hz, 1H), 2.61 (s, 3H), 2.25-1.79 (m, 11H) | 383 |

TABLE 3-continued

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 29 | 7.47-7.37 (m, 2H), 7.41-7.36 (m, 1H), 7.34 (s, 1H), 7.18 (t, J = 8.5 Hz, 1H), 7.09 (s, 1H), 6.18 (s, 1H), 2.71 (d, J = 10.0 Hz, 1H), 2.40 (s, 3H), 2.25-1.80 (m, 11H) | 388 |
| 30 | 7.91 (s, 1H), 7.46-7.42 (m, 2H), 7.38 (d, J = 5.0 Hz, 1H), 7.17 (t, J = 8.0 Hz, 1H), 6.19 (s, 1H), 6.06 (s, 1H), 2.71-2.67 (m, 4H), 2.20-1.79 (m, 11H) | 388 |
| 31 | 8.37 (d, J = 5.0 Hz, 1H), 8.20 (s, 1H), 7.97 (s, 1H), 7.47-7.44 (m, 2H), 7.40-7.36 (m, 1H), 7.22-7.17 (m, 2H), 6.23 (s, 1H), 2.73-2.70 (m, 1H), 2.41 (s, 3H), 2.28-1.78 (m, 11H) | 382 |
| 32 | 8.74 (s, 1H), 8.54 (s, 1H), 7.89 (s, 1H), 7.47-7.39 (m, 3H), 7.18 (s, 1H), 6.25 (s, 1H), 6.17 (s, 1H), 2.72 (m, 1H), 2.40 (s, 3H), 2.23-1.81 (m, 11H) | 382 |
| 33 | 9.21 (s, 1H), 8.97 (d, J = 5.5 Hz, 1H), 8.14 (s, 1H), 8.09 (s, 1H), 7.47-7.37 (m, 3H), 7.20-7.17 (m, 1H), 6.16 (s, 1H), 2.75 (d, J = 10.0 Hz, 1H), 2.27-1.79 (m, 11H) | 369 |
| 34 | 7.83 (d, J = 3.5 Hz, 1H), 7.55 (d, J = 3.0 Hz, 1H), 7.47-7.44 (m, 2H), 7.39-7.38 (m, 2H), 7.18 (s, 1H), 6.18 (s, 1H), 2.72 (d, J = 10.0 Hz, 1H), 2.26-1.78 (m, 11H) | 374 |
| 35 | 8.94 (s, 1H), 8.72 (s, 1H), 8.07 (d, J = 7.5 Hz, 1H), 7.54 (s, 1H), 7.49 (d, J = 4.5 Hz, 1H), 7.38 (s, 1H), 7.30-7.26 (m, 2H), 6.29 (s, 1H), 6.19 (s, 1H), 2.73-2.71 (m, 1H), 2.39 (s, 3H), 2.26-1.67 (m, 11H) | 364 |
| 36 | 8.74 (d, J = 5.5 Hz, 2H), 7.60-7.49 (m, 4H), 7.31-7.30 (m, 2H), 6.30 (s, 1H), 6.15 (s, 1H), 2.74-2.72 (m, 1H), 2.39 (s, 3H), 2.28-1.78 (m, 11H) | 364 |
| 37 | 9.16 (s, 1H), 8.59 (s, 1H), 8.00 (s, 1H), 7.54 (s, 1H), 7.51-7.49 (m, 1H), 7.29-7.27 (m, 2H), 6.27 (s, 1H), 2.75-2.73 (m, 1H), 2.59 (s, 3H), 2.38 (s, 3H), 2.24-1.78 (m, 11H) | 379 |
| 38 | 8.67 (d, J = 6.5 Hz, 1H), 8.20 (s, 1H), 7.55 (s, 1H), 7.51-7.49 (m, 1H), 7.31-7.25 (m, 3H), 6.19 (s, 1H), 2.71-2.69 (m, 1H), 2.62 (s, 3H), 2.39 (s, 3H), 2.23-1.80 (m, 11H) | 379 |
| 39 | 8.73 (s, 1H), 8.56 (s, 1H), 7.88 (s, 1H), 7.55 (s, 1H), 7.51 (d, J = 6.0 Hz, 1H), 7.32 (d, J = 6.0 Hz, 2H), 6.20 (s, 1H), 6.18 (s, 1H), 2.71 (m, 1H), 2.41 (s, 6H), 2.26-1.84 (m, 11H) | 378 |
| 40 | 8.86 (d, J = 5.0 Hz, 2H), 8.18 (s, 1H), 7.55 (s, 1H), 7.51 (d, J = 6.0 Hz, 1H), 7.43 (m, 1H), 7.32-7.30 (m, 2H), 6.22 (s, 1H), 2.71 (m, 1H), 2.41 (s, 3H), 2.27-1.83 (m, 11H) | 365 |
| 41 | 9.21 (s, 1H), 8.97 (d, J = 5.0 Hz, 1H), 8.15 (s, 1H), 8.10 (d, J = 5.0 Hz, 1H), 7.54 (s, 1H), 7.50 (d, J = 5.5 Hz, 1H), 7.32-7.26 (m, 2H), 6.17 (s, 1H), 2.74 (m, 1H), 2.39 (s, 3H), 2.28-1.80 (m, 11H) | 365 |
| 42 | 7.82 (s, 1H), 7.54-7.49 (m, 3H), 7.41 (s, 1H), 7.30-7.27 (m, 2H), 6.31 (s, 1H), 2.70-2.68 (m, 1H), 2.37 (s, 3H), 2.25-1.79 (m, 11H) | 370 |
| 43 | 8.85 (d, J = 5.0 Hz, 1H), 8.19 (s, 1H), 7.88 (d, J = 5.0 Hz, 1H), 7.54 (s, 1H), 7.50 (d, J = 6.0 Hz, 1H), 7.32-7.26 (m, 2H), 6.19 (s, 1H), 2.77-2.73 (m, 4H), 2.39 (s, 3H), 2.24-1.80 (m, 11H) | 379 |
| 44 | 7.54 (s, 1H), 7.50-7.48 (m, 1H), 7.41 (s, 1H), 7.32-7.26 (m, 2H), 7.10 (s, 1H), 6.17 (s, 1H), 2.71-2.69 (m, 1H), 2.47 (s, 3H), 2.39 (s, 3H), 2.26-1.77 (m, 11H) | 384 |
| 45 | 7.91 (s, 1H), 7.53 (s, 1H), 7.49 (m, 1H), 7.30-7.26 (m, 2H), 6.14 (s, 1H), 5.96 (s, 1H), 2.72-2.67 (m, 4H), 2.39 (s, 3H), 2.23-1.78 (m, 11H) | 384 |
| 46 | 8.36 (d, J = 2.5 Hz, 1H), 8.21-8.18 (m, 1H), 8.03 (s, 1H), 7.54-7.48 (m, 3H), 7.30-7.26 (m, 2H), 6.18 (s, 1H), 2.73-2.70 (m, 1H), 2.39 (s, 3H), 2.26-1.81 (m, 11H) | 382 |
| 47 | 8.33 (s, 1H), 8.18 (s, 1H), 8.06 (d, J = 8.0 Hz, 1H), 7.64 (d, J = 7.0 Hz, 1H), 7.54 (s, 1H), 7.50 (d, J = 6.0 Hz, 1H), 7.30-7.26 (m, 2H), 6.20 (s, 1H), 2.72-2.70 (m, 1H), 2.40 (s, 6H), 2.30-1.79 (m, 11H) | 378 |
| 48 | 8.37 (d, J = 5.0 Hz, 1H), 8.22 (s, 1H), 7.98 (s, 1H), 7.54 (s, 1H), 7.50 (d, J = 6.5 Hz, 1H), 7.32-7.22 (m, 3H), 6.20 (s, 1H), 2.72-2.70 (m, 1H), 2.42 (s, 3H), 2.39 (s, 3H), 2.27-1.80 (m, 11H) | 378 |
| 49 | 8.86 (d, J = 4.5 Hz, 1H), 8.37 (d, J = 3.0 Hz, 1H), 8.22-8.20 (m, 2H), 8.05 (s, 1H), 7.89 (d, J = 4.5 Hz, 1H), 7.56-7.52 (m, 1H), 2.80-2.78 (m, 4H), 2.28-1.60 (m, 11H) | 384 |
| 50 | 8.37 (d, J = 3.0 Hz, 1H), 8.31 (s, 1H), 8.22-8.20 (m, 2H), 8.06 (s, 1H), 7.98 (d, J = 7.5 Hz, 1H), 7.72 (t, J = 8.0 Hz, 1H), 7.55-7.51 (m, 1H), 7.27-7.26 (m, 1H), 2.79-2.76 (m, 1H), 2.57 (s, 3H), 2.26-2.05 (m, 7H), 1.88-1.84 (m, 4H) | 383 |
| 51 | 9.17 (s, 1H), 8.59 (s, 1H), 8.36 (d, J = 3.0 Hz, 1H), 8.21-8.18 (m, 1H), 8.04 (s, 1H), 8.00 (s, 1H), 7.54-7.50 (m, 1H), 2.79-2.76 (m, 1H), 2.59 (s, 3H), 2.28-1.80 (m, 11H) | 384 |
| 52 | 9.25 (s, 1H), 9.18 (s, 1H), 8.61 (s, 1H), 8.36 (s, 1H), 8.01 (s, 1H), 7.91 (s, 1H), 2.80 (m, 1H), 2.66 (s, 3H), 2.58 (s, 3H), 2.27-1.84 (m, 11H) | 381 |
| 53 | 9.25 (s, 1H), 8.36(s, 1H), 7.90 (s, 1H), 7.55-7.50 (m, 2H), 7.32-7.30 (m, 2H), 6.19 (s, 1H), 2.74 (d, J = 9.5 Hz, 1H), 2.66 (s, 3H), 2.40 (s, 3H), 2.28-1.83 (m, 11H) | 379 |
| 54 | 9.25 (s, 1H), 8.36 (s, 1H), 7.90 (s, 1H), 7.48-7.40 (m, 3H), 7.27-7.19 (m, 1H), 6.17 (s, 1H), 2.75 (m, 1H), 2.66 (s, 3H), 2.28-1.83 (m, 11H) | 383 |
| 55 | 9.25 (s, 1H), 8.96 (s, 1H), 7.90 (s, 1H), 7.71 (s, 1H), 7.66-7.36 (m, 3H), 6.17 (s, 1H), 2.76-2.74 (m, 1H), 2.66 (s, 3H), 2.25-1.82 (m, 11H) | 399 |

TABLE 3-continued

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 56 | 9.25-9.22 (m, 2H), 8.98 (d, J = 5.0 Hz, 1H), 8.36 (s, 1H), 8.11-8.09 (m, 2H), 7.90 (s, 1H), 2.79 (d, J = 10.0 Hz, 1H), 2.66 (s, 3H), 2.28-1.86 (m, 11H) | 367 |
| 57 | 9.25 (s, 1H), 8.36 (d, J = 4.5 Hz, 1H), 7.90-7.84 (m, 2H), 7.56 (d, J = 3.0 Hz, 1H), 7.40 (s, 1H), 2.76 (d, J = 10.0 Hz, 1H), 2.65 (s, 3H), 2.27-1.81 (m, 11H) | 372 |
| 58 | 9.25 (s, 1H), 8.36 (s, 1H), 7.91 (s, 1H), 7.74-7.72 (m, 2H), 7.50-7.42 (m, 3H), 6.22 (s, 1H), 2.75 (m, 1H), 2.65 (s, 3H), 2.26-1.82 (m, 11H) | 365 |
| 59 | 9.25 (s, 1H), 8.69 (d, J = 5.0 Hz, 1H); 8.36 (s, 2H), 7.90 (s, 1H), 7.27 (s, 1H), 2.76-2.74 (m, 1H), 2.65 (s, 3H), 2.63 (s, 3H), 2.27-1.82 (m, 11H) | 381 |
| 60 | 9.25 (s, 1H), 8.86 (d, J = 5.0 Hz, 1H), 8.36 (s, 1H), 8.20 (s, 1H), 7.91-7.88 (m, 2H), 2.80-2.78 (m, 4H), 2.66 (s, 3H), 2.28-1.85 (m, 11H) | 381 |
| 61 | 9.24 (s, 1H), 8.35 (s, 1H), 7.90 (s, 1H), 7.37 (s, 1H), 7.10 (s, 1H), 2.75 (m, 1H), 2.65 (s, 3H), 2.47 (s, 3H), 2.26-1.82 (m, 11H) | 386 |
| 62 | 9.25 (s, 1H), 8.37-8.19 (m, 3H), 8.05 (s, 1H), 7.91 (s, 1H), 7.55-7.51 (m, 1H), 2.77 (m, 1H), 2.65 (s, 3H), 2.27-1.84 (m, 11H) | 384 |
| 63 | 9.25 (s, 1H), 8.35-8.34 (m, 2H), 8.17 (s, 1H), 8.05 (d, J = 10.5 Hz, 1H), 7.91 (s, 1H), 7.64-7.62 (m, 1H), 2.77 (m, 1H), 2.65 (s, 3H), 2.40 (s, 3H), 2.29-1.83 (m, 11H) | 380 |
| 64 | 9.25 (s, 1H), 8.38-8.35 (m, 2H), 8.22 (s, 1H), 7.99 (s, 1H), 7.91 (s, 1H), 7.23-7.22 (m, 1H), 2.76 (m, 1H), 2.65 (s, 3H), 2.43 (s, 3H), 2.29-1.81 (m, 11H) | 380 |
| 65 | | 398 |
| 66 | 9.17 (s, 1H), 8.59 (s, 1H), 8.06-8.00 (m, 2H), 7.47-7.43 (m, 1H), 7.26-7.24 (m, 1H), 7.12-7.08 (m, 1H), 6.87-6.85 (m, 1H), 2.74-2.72 (m, 1H), 2.60 (s, 3H), 2.24-1.79 (m, 11H) | 383 |
| 67 | 9.17 (s, 1H), 8.60 (s, 1H), 7.98 (s, 1H), 7.26-7.23 (m, 2H), 6.93 (t, J = 3.5 Hz, 1H), 6.12 (s, 1H), 2.76-2.74 (m, 1H), 2.60 (s, 3H), 2.26-2.14 (m, 5H), 2.07-2.01 (m, 2H), 1.87-1.80 (m, 4H) | 401 |
| 68 | 9.10 (s, 1H), 8.86 (s, 1H), 8.65 (d, J = 3.5 Hz, 1H), 8.53 (s, 1H), 8.01-7.99 (m, 1H), 7.92 (s, 1H), 7.32-7.30 (m, 1H), 6.16 (s, 1H), 2.72-2.71 (m, 1H), 2.53 (s, 3H), 2.20-1.74 (m, 11H) | 366 |
| 69 | 9.09 (s, 1H), 8.52 (s, 1H), 7.91 (s, 1H), 7.63 (s, 1H), 7.52 (d, J = 8.0 Hz, 1H), 7.38 (d, J = 8.0 Hz, 1H), 7.29 (t, J = 8.0 Hz, 1H), 6.12 (s, 1H), 2.69-2.67 (m, 1H), 2.53 (s, 3H), 2.21-1.75 (m, 11H) | 399 |
| 70 | 9.19 (s, 1H), 8.69 (d, J = 5.5 Hz, 1H), 8.61 (s, 1H), 8.22 (s, 1H), 8.01 (s, 1H), 7.27 (s, 1H), 2.78 (m, 1H), 2.63 (s, 3H), 2.61 (s, 3H), 2.28-1.62 (m, 11H) | 381 |
| 71 | 9.23 (s, 1H), 9.19 (s, 1H), 8.98 (d, J = 5.0 Hz, 1H), 8.61 (s, 1H), 8.16 (s, 1H), 8.11 (m, 1H), 8.01 (s, 1H), 2.82 (m, 1H), 2.61 (s, 3H), 2.29-1.86 (m, 11H) | 367 |
| 72 | 9.19 (s, 1H), 8.61 (s, 1H), 8.00 (s, 1H), 7.85 (d, J = 3.0 Hz, 1H), 7.57 (d, J = 3.0 Hz, 1H), 7.41(s, 1H), 2.79 (m, 1H), 2.61 (s, 3H), 2.27-1.83 (m, 11H) | 372 |
| 73 | 9.17 (s, 1H), 8.60 (s, 1H), 7.99 (s, 1H), 7.73 (d, J = 8.0 Hz, 2H), 7.50-7.41 (m, 3H), 7.18 (s, 1H), 2.77 (m, 1H), 2.60 (s, 3H), 2.25-1.83 (m, 11H) | 365 |
| 74 | 9.19 (s, 1H), 8.61 (s, 1H), 8.03 (s, 1H), 7.36 (s, 1H), 7.11 (s, 1H), 2.79 (m, 1H), 2.61 (s, 3H), 2.48 (s, 3H), 2.26-1.82 (m, 11H) | 386 |
| 75 | 9.17 (s, 1H), 8.59 (s, 1H), 8.33 (s, 1H), 8.16 (s, 1H), 8.06 (d, J = 8.0 Hz, 1H), 8.00 (s, 1H), 7.63 (d, J = 7.5 Hz, 1H), 2.79 (m, 1H), 2.59 (s, 3H), 2.40 (s, 3H), 2.30-1.83 (m, 11H) | 380 |
| 76 | 9.18 (s, 1H), 8.60 (s, 1H), 8.39 (d, J = 5.0 Hz, 1H), 8.23 (s, 1H), 8.02 (d, J = 10.0 Hz, 2H), 7.24 (d, J = 5.0 Hz, 1H), 2.80 (m, 1H), 2.61 (s, 3H), 2.43 (s, 3H), 2.25-1.83 (m, 11H) | 380 |
| 77 | 9.17 (s, 1H), 8.72 (s, 1H), 8.60 (s, 1H), 8.54 (s, 1H), 7.98 (s, 1H), 7.87 (s, 1H), 6.18 (s, 1H), 2.77 (d, J = 10.0 Hz, 1H), 2.60 (s, 3H), 2.39 (s, 3H), 2.27-1.84 (m, 11H) | 380 |
| 78 | 9.40 (s, 1H), 9.19 (s, 1H), 8.76 (d, J = 3.0 Hz, 1H), 8.61 (s, 1H), 8.52 (t, J = 2.0 Hz, 1H), 8.01 (s, 1H), 7.96 (s, 1H), 2.82 (d, J = 10.0 Hz, 1H), 2.61 (s, 3H), 2.29-1.86 (m, 11H) | 367 |
| 79 | 9.18 (s, 1H), 8.88 (d, J = 2.0 Hz, 2H), 8.61 (s, 1H), 8.20 (t, J = 2.0 Hz, 1H), 8.01 (s, 1H), 7.44 (s, 1H), 2.79 (d, J = 10.0 Hz, 1H), 2.62 (s, 3H), 2.29-1.82 (m, 11H) | 367 |
| 80 | 9.19 (s, 1H), 8.61 (s, 1H), 8.35 (s, 1H), 8.03-7.98 (m, 2H), 7.75-7.72 (t, J = 8.0 Hz, 1H), 7.29 (s, 1H), 2.81-2.79 (m, 1H), 2.61 (s, 3H), 2.59 (s, 3H), 2.25-1.85 (m, 11H) | 380 |
| 81 | 8.74 (s, 1H), 8.55 (s, 1H), 8.30 (s, 1H), 8.24 (s, 1H), 7.98 (d, J = 8.0 Hz, 1H), 7.90 (s, 1H), 7.73 (t, J = 8.0 Hz, 1H), 7.27 (s, 1H), 6.24 (s, 1H), 2.77-2.75 (m 1H), 2.57 (s, 3H), 2.40 (s, 3H), 2.26-1.82 (m, 11H) | 379 |
| 82 | 8.30 (s, 1H), 7.98 (d, J = 7.5 Hz, 1H), 7.73 (t, J = 8.0 Hz, 1H), 7.56-7.50 (m, 2H), 7.32-7.27 (m, 3H), 6.21 (s, 1H), 2.74 (m, 1H), 2.57 (s, 3H), 2.51 (s, 3H), 2.21-1.81 (m, 11H) | 378 |
| 83 | 9.40 (s, 1H), 8.75 (d, J = 3.0 Hz, 1H), 8.52 (d, J = 4.0 Hz, 1H), 8.31 (s, 1H), 7.98-7.97 (m, 1H), 7.73 (t, J = 8.0 Hz, 1H), 7.27 (s, 1H), 2.79 (m, 1H), 2.57 (s, 3H), 2.28-1.82 (m, 11H) | 366 |
| 84 | 8.87-8.86 (m, 2H), 8.32 (s, 1H), 8.20 (s, 1H), 7.98 (d, J = 7.0 Hz, 1H), 7.73 (t, J = 8.0 Hz, 1H), 7.43 (t, J = 5.0 Hz, 1H), 7.28 (s, 1H), 2.78-2.76 (m, 1H), 2.58 (s, 3H), 2.28-1.82 (m, 11H) | 366 |

TABLE 3-continued

Analytical data of compounds of formula I

| Example No. | $^1$H NMR (400 or 500 MHz, CDCl$_3$), δ (PPM) | ESI-MS m/z $(M + H)^+$ |
|---|---|---|
| 85 | 9.23 (d, J = 2.0 Hz, 1H), 8.98 (d, J = 5.0 Hz, 1H), 8.31 (s, 1H), 8.17-8.10 (m, 2H), 7.98 (d, J = 8.0 Hz, 1H), 7.73 (t, J = 8.0 Hz, 1H), 7.28 (s, 1H), 2.79 (m, 1H), 2.57 (s, 3H), 2.28-1.82 (m, 11H) | 366 |
| 86 | 8.30 (s 1H), 7.97 (d, J = 8.0 Hz, 1H), 7.85 (d, J = 3.5 Hz, 1H), 7.72 (t, J = 7.5 Hz, 1H), 7.56 (d, J = 3.0 Hz, 1H), 7.41 (s, 1H), 7.27 (s, 1H), 2.76 (m, 1H), 2.57 (s, 3H), 2.28-1.82 (m, 11H) | 371 |
| 87 | 8.31 (s 1H), 7.98 (d, J = 7.5 Hz, 1H), 7.74-7.71 (m, 3H), 7.50-7.42 (m, 3H), 7.27 (s, 1H), 6.22 (s, 1H), 2.75 (m, 1H), 2.57 (s, 3H), 2.28-1.82 (m, 11H) | 364 |
| 88 | 9.26 (d, J = 1.0 Hz, 1H), 8.36-8.32 (m, 2H), 7.99-7.92 (m, 2H), 7.73 (t, J = 8.0 Hz, 1H), 7.27 (s, 1H), 2.78 (m, 1H), 2.66 (s, 3H), 2.57 (s, 3H), 2.27-1.84 (m, 11H) | 380 |
| 89 | 8.68 (d, J = 5.0 Hz, 1H), 8.30 (s, 1H), 8.22 (s, 1H), 7.98 (d, J = 7.5 Hz, 1H), 7.71 (t, J = 8.0 Hz, 1H), 7.27-7.25 (m, 2H), 2.77 (m, 1H), 2.62 (s, 3H), 2.57 (s, 3H), 2.27-1.82 (m, 11H) | 380 |
| 90 | 8.86 (d, J = 5.0 Hz, 1H), 8.31 (s, 1H), 8.21 (s, 1H), 7.98 (d, J = 8.0 Hz, 1H), 7.90 (d, J = 5.5 Hz, 1H), 7.73 (t, J = 8.0 Hz, 1H), 7.28 (s, 1H), 2.81-2.78 (m, 4H), 2.57 (s, 3H), 2.30-1.84 (m, 11H) | 380 |
| 91 | 8.28 (s, 1H), 7.97 (d, J = 7.5 Hz, 1H), 7.92 (s, 1H), 7.73 (t, J = 8.0 Hz, 1H), 7.27 (s, 1H), 5.99 (s, 1H), 2.74-2.72 (m, 4H), 2.57 (s, 3H), 2.26-1.82 (m, 11H) | 385 |
| 92 | 8.34 (m, 2H), 8.20 (s, 1H), 8.07 (d, J = 8.0 Hz, 1H), 7.98 (d, J = 8.0 Hz, 1H), 7.73 (t, J = 8.0 Hz, 1H), 7.64 (d, J = 7.5 Hz, 1H), 7.27 (s, 1H), 2.77 (m, 1H), 2.57 (s, 3H), 2.41 (s, 3H), 2.26-1.82 (m, 11H) | 379 |
| 93 | 8.38 (d, J = 5.5 Hz, 1H), 8.32 (s, 1H), 8.24 (s, 1H), 8.00-7.97 (m, 2H), 7.72 (t, J = 8.0 Hz, 1H), 7.27-7.22 (m, 2H), 2.78-2.76 (m, 1H), 2.57 (s, 3H), 2.43 (s, 3H), 2.26-1.82 (m, 11H) | 379 |
| 94 |  | 384 |
| 95 | 9.38 (s, 1H), 8.75 (s, 1H), 8.51 (s, 1H), 7.99 (s, 1H), 7.89-7.97 (m, 2H), 7.74 (m, 1H), 7.58 (m, 1H), 6.21 (s, 1H), 2.79 (m, 1H), 1.78-2.35 (m, 11H) | 419 |
| 96 | 9.38 (s, 1H), 8.75 (m, 1H), 8.51 (m, 1H), 8.02 (s, 1H), 7.89-7.99 (m, 2H), 7.78 (m, 1H), 7.57 (m, 1H), 6.20 (s, 1H), 2.78 (m, 1H), 1.78-2.32 (m, 11H) | 376 |
| 97 | 9.40 (s, 1H), 8.73 (m, 1H), 8.50 (m, 1H), 8.07 (m, 1H), 7.90-7.99 (m, 2H), 7.85 (m, 1H), 7.07 (m, 1H), 2.78 (m, 1H), 1.78-2.32 (m, 11H) | 370 |
| 98 | 9.38 (d, J = 2.5 Hz, 1H), 8.74 (d, J = 2.5 Hz, 1H), 8.51-8.50 (m, 1H), 7.95 (s, 1H), 7.54 (s, 1H), 7.50-7.49 (d, J = 6.0 Hz, 1H), 7.31-7.30 (d, J = 5.5 Hz, 2H), 6.18 (s, 1H), 2.75-2.73 (m, 1H), 2.39 (s, 3H), 2.25-1.82 (m, 11H) | 365 |
| 99 | 9.39 (d, J = 2.0 Hz, 1H), 8.75 (d, J = 2.5 Hz, 1H), 8.52-8.51 (t, J = 2.0 Hz, 1H), 7.95 (s, 1H), 7.72 (t, J = 2.0 Hz, 1H), 7.61-7.60 (d, J = 7.0 Hz, 1H), 7.48-7.46 (m, 1H), 7.39-7.36 (m, 1H), 6.18 (s, 1H), 2.77-2.75 (m, 1H), 2.27-1.82 (m, 11H) | 385 |
| 100 | 9.39 (d, J = 1.0 Hz, 1H), 8.85 (d, J = 5.0 Hz, 1H), 8.75 (d, J = 2.0 Hz, 1H), 8.50 (s, 1H), 8.19 (s, 1H), 7.95 (s, 1H), 7.88 (d, J = 5.0 Hz, 1H), 2.81 (m, 1H), 2.77 (s, 3H), 2.28-1.84 (m, 11H) | 367 |
| 101 | 9.39 (d, J = 1.0 Hz, 1H), 8.75 (d, J = 2.0 Hz, 1H), 8.52 (t, J = 2.0 Hz, 1H), 7.96 (s, 1H), 7.37 (s, 1H), 7.11 (s, 1H), 2.78 (m, 1H), 2.47 (s, 3H), 2.27-1.84 (m, 11H) | 372 |
| 102 | 9.38 (d, J = 1.0 Hz, 1H), 8.74 (d, J = 2.5 Hz, 1H), 8.50 (d, J = 2.0 Hz, 1H), 8.36 (d, J = 2.0 Hz, 1H), 8.21 (m, 1H), 8.04 (s, 1H), 7.95 (s, 1H), 7.54-7.51 (m, 1H), 2.79 (m, 1H), 2.27-1.84 (m, 11H) | 370 |
| 103 | 9.40 (d, J = 1.5 Hz, 1H), 8.75 (d, J = 2.5 Hz, 1H), 8.52 (t, J = 2.0 Hz, 1H), 8.39 ((d, J = 4.5 Hz, 1H), 8.23 (s, 1H), 8.00 (s, 1H), 7.97 (s, 1H), 7.24 (d, J = 5.0 Hz, 1H), 2.77-2.75 (m, 1H), 2.43 (s, 3H), 2.22-1.84 (m, 11H) | 366 |
| 104 | 8.85 (d, J = 5.0 Hz, 1H), 8.54-8.53 (m, 1H), 8.23-8.17 (m, 3H), 7.89-7.84 (m, 2H), 7.44-7.41 (m, 1H), 2.80-2.78 (m, 4H), 2.23-1.82 (m, 11H) | 366 |
| 105 | 8.54 (d, J = 5.0 Hz, 1H), 8.32 (s, 1H), 8.25 (s, 1H), 8.18 (d, J = 8.0 Hz, 1H), 7.98 (d, J = 7.5 Hz, 1H), 7.87-7.83 (m, 1H), 7.73-7.70 (m, 1H), 7.43-7.41 (m, 1H), 7.27-7.26 (m, 1H), 2.79-2.77 (m, 1H), 2.57 (s, 3H), 2.27-1.82 (m, 11H) | 365 |
| 106 | 9.25 (s, 1H), 8.84 (d, J = 4.0 Hz, 1H), 8.36 (s, 1H), 8.24 (s, 1H), 8.18 (d, J = 6.0 Hz, 1H), 7.92-7.84 (m, 2H), 7.43 (dd, J = 12.0 Hz, 5.0 Hz, 1H), 2.79-2.77 (m, 1H), 2.65 (s, 3H), 2.25-1.57 (m, 11H) | 366 |
| 107 | 8.69 (d, J = 5.0 Hz, 1H), 8.54 (d, J = 5.0 Hz, 1H), 8.23-8.17 (m, 3H), 7.86-7.83 (m, 1H), 7.43-7.41 (m, 1H), 7.27-7.25 (m, 1H), 2.77-2.74 (m, 1H), 2.63 (s, 3H), 2.26-1.82 (m, 11H) | 366 |
| 108 | 8.54 (d, J = 5.0 Hz, 1H), 8.22-8.17 (m, 2H), 7.85 (m, 1H), 7.43-7.39 (m, 2H), 7.10 (s, 1H), 2.77-2.75 (m, 1H), 2.47 (s, 3H), 2.27-1.84 (m, 11H) | 371 |
| 109 | 8.53 (d, J = 4.5 Hz, 1H), 8.21-8.16 (m, 2H), 7.92 (s, 1H), 7.86-7.83 (m, 1H), 7.43-7.41 (m, 1H), 6.04 (s, 1H), 2.74-2.72 (m, 4H), 2.29-1.78 (m, 11H) | 371 |
| 110 | 8.54 (d, J = 4.0 Hz, 1H), 8.37 (d, J = 3.0 Hz, 1H), 8.27-8.18 (m, 3H), 8.06 (s, 1H), 7.86 (t, J = 8.0 Hz, 1H), 7.53-7.42 (m, 2H), 2.78-2.76 (m, 1H), 2.27-1.84 (m, 11H) | 369 |
| 111 | 8.52 (d, J = 4.5 Hz, 1H), 8.33 (s, 1H), 8.23 (s, 1H), 8.19 (s, 1H), 8.17 (d, J = 7.5 Hz, 1H), 8.06 (d, J = 8.0 Hz, 1H), 7.85-7.82 (m, 1H), 7.64 (dd, J = 8.0 Hz, 1.5 Hz, 1H), 7.42-7.39 (m, 1H), 2.77-2.75 (m, 1H), 2.39 (s, 3H), 2.27-1.80 (m, 11H) | 365 |

TABLE 3-continued

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 112 | 8.54 (d, J = 5.0 Hz, 1H), 8.38 (d, J = 5.0 Hz, 1H), 8.25 (m, 2H), 8.18 (d, J = 8.0 Hz, 1H), 8.00 (s, 1H), 7.85 (t, J = 8.0 Hz, 1H), 7.42-7.39 (m, 1H), 7.22 (d, J = 5.0 Hz, 1H), 2.77-2.75 (m, 1H), 2.43 (s, 3H), 2.27-1.84 (m, 11H) | 365 |
| 113 | 8.73 (s, 1H), 8.54 (d, J = 5.0 Hz, 2H), 8.23-8.16 (m, 2H), 7.89-7.84 (m, 2H), 7.44-7.42 (m, 1H), 6.24 (s, 1H), 2.77-2.75 (m, 1H), 2.40 (s, 3H), 2.32-1.81 (m, 11H) | 365 |
| 114 | 8.54 (d, J = 4.0 Hz, 1H), 8.23 (s, 1H), 8.18 (d, J = 8.0 Hz, 1H), 7.85 (t, J = 7.5 Hz, 1H), 7.55 (s, 1H), 7.51 (d, J = 6.5 Hz, 1H), 7.44-7.27 (m, 3H), 6.22 (s, 1H), 2.75-2.73 (m, 1H), 2.42 (s, 3H), 2.40-1.80 (m, 11H) | 364 |
| 115 | 8.54 (d, J = 5.0 Hz, 1H), 8.22 (s, 1H), 8.18 (d, J = 7.5 Hz, 1H), 7.85 (t, J = 8.0 Hz, 1H), 7.72 (s, 1H), 7.61 (d, J = 8.0 Hz, 1H), 7.47-7.27 (m, 3H), 6.20 (s, 1H), 2.76-2.73 (m, 1H), 2.30-1.80 (m, 11H) | 384 |
| 116 | 8.35 (s, 1H), 8.10 (s, 1H), 8.00 (d, J = 8.0 Hz, 1H), 7.75 (t, J = 7.5 Hz, 1H), 7.24-7.43 (m, 3H), 2.80 (m, 1H), 2.60 (s, 3H), 2.57 (s, 3H), 1.78-2.30 (m, 11H) | 397 |
| 117 | 8.28 (s, 1H), 7.97 (d, J = 8.0 Hz, 1H), 7.72 (t, J = 7.5 Hz, 1H), 7.36-7.50 (m, 3H), 7.25-7.29 (m, 1H), 7.19 (t, J = 1.0 Hz, 1H), 6.20 (s, 1H), 2.74-2.76 (m, 1H), 2.58 (s, 3H), 1.78-2.32 (m, 11H) | 382 |
| 118 | 8.30 (s, 1H), 7.98 (d, J = 7.5 Hz, 1H), 7.73 (t, J = 8.0 Hz, 1H), 7.48-7.60 (m, 2H), 7.22-7.32 (m, 3H), 6.20 (s, 1H), 2.72-2.78 (m, 1H), 2.58 (s, 3H), 2.41 (s, 3H), 1.78-2.32 (m, 11H) | 378 |
| 119 | 8.54 (d, J = 5.0 Hz, 1H), 8.32 (s, 1H), 8.25 (s, 1H), 8.18 (d, J = 8.0 Hz, 1H), 7.98 (d, J = 7.5 Hz, 1H), 7.87-7.83 (m, 1H), 7.73-7.70 (m, 1H), 7.43-7.41 (m, 1H), 7.27-7.26 (m, 1H), 2.79-2.77 (m, 1H), 2.57 (s, 3H), 1.78-2.32 (m, 11H) | 365 |
| 120 | 8.86 (d, J = 5.0 Hz, 1H), 8.31 (s, 1H), 8.21 (s, 1H), 7.98 (d, J = 8.0 Hz, 1H), 7.90 (d, J = 5.5 Hz, 1H), 7.73 (t, J = 8.0 Hz, 1H), 7.22-7.30 (m, 1H), 2.75-2.83 (m, 4H), 2.58 (s, 3H), 1.78-2.32 (m, 11H) | 380 |
| 121 | 9.22 (d, J = 2.0 Hz, 1H), 8.98 (d, J = 5.0 Hz, 1H), 8.31 (s, 1H), 8.18 (s, 1H), 8.09-8.12 (m, 1H), 7.97 (d, J = 8.0 Hz, 1H), 7.72 (t, J = 8.0 Hz, 1H), 7.22-7.30 (m, 1H), 2.75-2.82 (m, 1H), 2.57 (s, 3H), 1.78-2.32 (m, 11H) | 366 |
| 122 | 8.40 (s, 1H), 8.00 (d, J = 7.5 Hz, 1H), 7.74-7.79 (m, 3H), 7.41-7.54 (m, 3H), 7.27 (s, 1H), 6.24 (s, 1H), 2.75 (m, 1H), 2.60 (s, 3H), 1.76-2.32 (m, 1H) | 364 |
| 123 | 8.35 (s, 1H), 8.10 (s, 1H), 8.00 (d, J = 8.0 Hz, 1H), 7.75 (t, J = 7.5 Hz, 1H), 7.24-7.43 (m, 3H), 2.80 (m, 1H), 2.60 (s, 3H), 2.57 (s, 3H), 1.78-2.30 (m, 11H) | 397 |
| 124 | 8.86 (d, J = 5.0 Hz, 1H), 8.31 (s, 1H), 8.21 (s, 1H), 7.98 (d, J = 8.0 Hz, 1H), 7.90 (d, J = 5.5 Hz, 1H), 7.73 (t, J = 8.0 Hz, 1H), 7.22-7.30 (m, 1H), 2.75-2.83 (m, 4H), 2.58 (s, 3H), 1.78-2.32 (m, 11H) | 380 |
| 125 | 8.28 (s, 1H), 7.97 (d, J = 8.0 Hz, 1H), 7.72 (t, J = 7.5 Hz, 1H), 7.36-7.50 (m, 3H), 7.25-7.29 (m, 1H), 7.19 (t, J = 1.0 Hz, 1H), 6.18 (s, 1H), 2.72-2.78 (m, 1H), 2.56 (s, 3H), 1.78-2.32 (m, 11H) | 382 |
| 126 | 8.54 (d, J = 5.0 Hz, 1H), 8.32 (s, 1H), 8.25 (s, 1H ), 8.18 (d, J = 8.0 Hz, 1H), 7.98 (d, J = 7.5 Hz, 1H), 7.87-7.83 (m, 1H), 7.73-7.70 (m, 1H), 7.43-7.41 (m, 1H), 7.27-7.26 (m, 1H), 2.77-2.79 (m, 1H), 2.57 (s, 3H), 1.78-2.32 (m, 11H) | 365 |
| 127 | 9.22 (d, J = 2.0 Hz, 1H), 8.98 (d, J = 5.0 Hz, 1H), 8.31 (s, 1H), 8.18 (s, 1H), 8.09-8.12 (m, 1H), 7.97 (d, J = 8.0 Hz, 1H), 7.72 (t, J = 8.0 Hz, 1H), 7.22-7.30 (m, 1H), 2.75-2.82 (m, 1H), 2.57 (s, 3H), 1.78-2.32 (m, 11H) | 366 |
| 128 | 8.37 (d, J = 3.0 Hz, 1H), 8.31 (s, 1H), 8.17-8.22 (m, 1H), 8.05 (s, 1H), 7.98 (d, J = 7.5 Hz, 1H), 7.72 (t, J = 8.0 Hz, 1H), 7.48-7.55 (m, 1H), 7.25-7.30 (m, 1H), 2.73-2.80 (m, 1H), 2.57 (s, 3H), 1.78-2.30 (m, 11H) | 383 |
| 129 | 8.35 (s, 1H), 8.00 (d, J = 8.0 Hz, 1H), 7.85 (d, J = 3.5 Hz, 1H), 7.74 (t, J = 7.5 Hz, 1H), 7.56 (d, J = 3.0 Hz, 1H), 7.45 (s, 1H), 7.24-7.32 (m, 1H), 2.78 (m, 1H), 2.60 (s, 3H), 1.78-2.32 (m, 11H) | 371 |
| 130 | 8.40 (d, J = 5.5 Hz, 1H), 8.35 (s, 1H), 8.29 (s, 1H), 7.89-8.02 (m, 2H), 7.72 (t, J = 8.0 Hz, 1H), 7.15-7.33 (m, 2H), 2.76 (m, 1H), 2.58 (s, 3H), 2.42 (s, 3H), 1.75-2.28 (m, 11H) | 379 |
| 131 | 8.32 (s, 1H), 8.20 (m, 1H), 8.12 (m, 1H), 8.05 (s, 1H), 7.97 (m, 1H), 7.70 (t, J = 8.0 Hz), 7.23-7.29 (m, 2H), 3.91 (s, 3H), 2.78 (m, 1H), 2.57 (s, 3H), 1.78-2.30 (m, 11H) | 395 |
| 132 | 9.19 (s, 1H), 8.61 (s, 1H), 8.35 (s, 1H), 7.98-8.03 (m, 2H), 7.72-7.75 (t, J = 8.0 Hz, 1H), 7.29 (s, 1H), 2.82 (m, 1H), 2.61 (s, 3H), 2.59 (s, 3H), 1.82-2.32 (m, 11H) | 380 |
| 133 | 9.19 (s, 1H), 8.61 (s, 1H), 8.03 (s, 1H), 7.36 (s, 1H), 7.11 (s, 1H), 2.79 (m, 1H), 2.61 (s, 3H), 2.48 (s, 3H), 1.80-2.32 (m, 11H) | 386 |
| 134 | 9.17 (s, 1H), 8.60 (s, 1H), 7.99 (s, 1H), 7.57 (s, 1H), 7.50-7.60 (m, 1H), 7.28-7.40 (m, 2H), 6.20 (s, 1H), 2.78 (m, 1H), 2.61 (s, 3H), 2.40 (s, 3H), 1.78-2.32 (m, 11H) | 379 |
| 135 | 9.19 (s, 1H), 8.61 (s, 1H), 7.82-8.09 (m, 4H), 7.06-7.12 (m, 1H), 2.80 (m, 1H), 2.61 (s, 3H), 1.78-2.32 (m, 11H) | 384 |
| 136 | 9.16 (s, 1H), 8.60 (s, 1H), 7.99 (s, 1H), 7.20-7.30 (m, 2H), 6.89-6.97 (m, 1H), 6.27 (s, 1H), 2.75 (m, 1H), 2.60 (s, 3H), 1.78-2.31 (m, 11H) | 401 |
| 137 | 9.19 (s, 1H), 8.61 (s, 1H), 8.35 (s, 1H), 7.98-8.03 (m, 2H), 7.72-7.75 (t, J = 8.0 Hz, 1H), 7.29 (s, 1H), 2.82 (m, 1H), 2.61 (s, 3H), 2.59 (s, 3H), 1.82-2.32 (m, 11H) | 380 |
| 138 | 9.19 (s, 1H), 8.61 (s, 1H), 8.03 (s, 1H), 7.36 (s, 1H), 7.11 (s, 1H), 2.79 (m, 1H), 2.61 (s, 3H), 2.48 (s, 3H), 1.80-2.32 (m, 11H) | 386 |

TABLE 3-continued

Analytical data of compounds of formula I

| Example No. | ¹H NMR (400 or 500 MHz, CDCl₃), δ (PPM) | ESI-MS m/z (M + H)⁺⁾ |
|---|---|---|
| 139 | 9.17 (s, 1H), 8.60 (s, 1H), 7.99 (s, 1H), 7.57 (s, 1H), 7.50-7.60 (m, 1H), 7.28-7.40 (m, 2H), 6.20 (s, 1H), 2.78 (m, 1H), 2.61 (s, 3H), 2.40 (s, 3H), 1.78-2.32 (m, 11H) | 379 |
| 140 | 9.19 (s, 1H), 8.61 (s, 1H), 7.82-8.09 (m, 4H), 7.06-7.12 (m, 1H), 2.80 (m, 1H), 2.61 (s, 3H), 1.78-2.32 (m, 11H) | 384 |
| 141 | 8.54 (d, J = 4.0 Hz, 1H), 8.23 (s, 1H), 8.18 (d, J = 8.0 Hz, 1H), 7.88 (t, J = 7.5 Hz, 1H), 7.55 (s, 1H), 7.53 (d, J = 6.5 Hz, 1H), 7.27-7.50 (m, 3H), 6.20 (s, 1H), 2.75 (m, 1H), 2.44 (s, 3H), 1.78-2.32 (m, 11H) | 364 |
| 142 | 8.54 (d, J = 5.0 Hz, 1H), 8.30 (s, 1H), 8.20 (d, J = 7.5 Hz, 1H), 7.88 (t, J = 8.0 Hz, 1H), 7.36-7.50 (m, 4H), 7.16-7.22 (m, 1H), 6.20 (s, 1H), 2.75 (m, 1H), 1.78-2.32 (m, 11H) | 368 |
| 143 | 8.54 (d, J = 5.0 Hz, 1H), 8.30 (s, 1H), 8.20 (d, J = 7.5 Hz, 1H), 7.88 (t, J = 8.0 Hz, 1H), 7.35-7.48 (m, 2H), 7.10 (s, 1H), 2.76 (m, 1H), 2.47 (s, 3H), 1.78-2.32 (m, 11H) | 371 |
| 144 | 8.86 (d, J = 5.0 Hz, 1H), 8.52-8.58 (m, 1H), 8.18-8.32 (m, 3H), 7.83-7.92 (m, 2H), 7.40-7.50 (m, 1H), 2.81 (m, 1H), 2.80 (s, 3H), 1.78-2.32 (m, 11H) | 366 |
| 145 | 8.54 (d, J = 4.0 Hz, 1H), 8.20-8.45 (m, 4H), 8.06 (s, 1H), 7.95 (t, J = 8.0 Hz, 1H), 7.44-7.60 (m, 2H), 2.76-2.81 (m, 1H), 1.78-2.32 (m, 11H) | 369 |
| 146 | 8.54 (d, J = 4.0 Hz, 1H), 8.28 (s, 1H), 7.80-8.20 (m, 5H), 7.42-7.50 (m, 1H), 7.06-7.12 (m, 1H), 2.75 (m, 1H), 1.78-2.32 (m, 11H) | 369 |
| 147 | 8.54 (d, J = 4.0 Hz, 1H), 8.25 (s, 1H), 8.20 (d, J = 7.8 Hz, 1H), 8.10 (s, 1H), 7.85 (t, J = 8.0 Hz, 1H), 7.20-7.47 (m, 3H), 2.75-2.82 (m, 1H), 2.56 (s, 3H), 1.78-2.32 (m, 11H) | 383 |
| 148 | 8.54 (d, J = 4.0 Hz, 1H), 8.25 (s, 1H), 8.20 (d, J = 8.0 Hz, 1H), 8.0 (s, 1H), 7.40-7.98 (m, 5H), 6.25 (s, 1H), 2.80 (m, 1H), 1.78-2.40 (m, 11H) | 418 |
| 149 | 8.54 (d, J = 4.0 Hz, 1H), 8.24 (s, 1H), 8.20 (d, J = 8.0 Hz, 1H), 7.40-8.05 (m, 6H), 6.25 (s, 1H), 2.75-2.80 (m, 1H), 1.78-2.40 (m, 11H) | 375 |
| 150 | 8.54 (d, J = 4.0 Hz, 1H), 8.25 (s, 1H), 8.20 (d, J = 8.0 Hz, 1H), 7.89 (t, J = 7.8 Hz, 1H), 7.80 (s, 1H), 7.42-7.78 (m, 3H), 6.20 (s, 1H), 2.80 (m, 1H), 1.78-2.40 (m, 11H) | 393 |
| 151 | 9.18 (s, 1H), 8.61 (s, 1H), 8.00 (s, 1H), 7.75-7.80 (m, 1H), 7.07-7.20 (m, 2H), 6.81-6.90 (m, 1H), 2.75 (m, 1H), 2.63 (s, 3H), 1.78-2.32 (m, 11H) | 401 |
| 152 | 9.20 (s, 1H), 8.72 (s, 1H), 7.95-8.11 (m, 3H), 7.76 (s, 1H), 7.08-7.12 (m, 1H), 2.80 (m, 1H), 2.63 (s, 3H), 1.78-2.32 (m, 11H) | 384 |
| 153 | 9.20 (s, 1H), 8.73 (s, 1H), 8.00 (s, 1H), 7.82 (s, 1H), 7.70-7.75 (m, 1H), 7.48-7.54 (m, 1H), 6.20 (s, 1H), 2.80 (m, 1H), 2.63 (s, 3H), 1.78-2.40 (m, 11H) | 408 |
| 154 | 9.17 (s, 1H), 8.59 (s, 1H), 8.36 (d, J = 3.0 Hz, 1H), 8.18-8.21 (m, 1H), 8.04 (s, 1H), 8.00 (s, 1H), 7.50-7.54 (m, 1H), 2.76-2.79 (m, 1H), 2.59 (s, 3H), 1.78-2.32 (m, 11H) | 384 |
| 155 | 9.16 (s, 1H), 8.60 (s, 1H), 8.25-8.30 (m, 1H), 8.00 (s, 1H), 7.80 (s, 1H), 7.26-7.35 (m, 1H), 2.80 (m, 1H), 2.60 (s, 3H), 1.78-2.32 (m, 11H) | 402 |
| 156 | 9.18 (s, 1H), 8.85 (d, J = 5.1 Hz, 1H), 8.60 (s, 1H), 8.19 (s, 1H), 8.00 (s, 1H), 7.88 (d, J = 5.0 Hz, 1H), 2.77-2.83 (m, 1H), 2.77 (s, 3H), 2.60 (s, 3H), 1.78-2.32 (m, 11H). | 381 |
| 157 | 9.18 (s, 1H), 8.85 (d, J = 5.1 Hz, 1H), 8.60 (s, 1H), 8.19 (s, 1H), 8.00 (s, 1H), 7.88 (d, J = 5.0 Hz, 1H), 2.77-2.83 (m, 1H), 2.77 (s, 3H), 2.60 (s, 3H), 1.78-2.32 (m, 11H). | 381 |
| 158 | 9.17 (s, 1H), 8.57 (s, 1H), 8.51-8.54 (m, 1H), 8.23 (s, 1H), 8.15-8.19 (m, 1H), 8.01 (s, 1H), 7.82-7.87 (m, 1H), 7.39-7.44 (m, 1H), 2.77-2.82 (m, 1H), 2.60 (s, 3H), 1.78-2.32 (m, 11H). | 366 |
| 159 | 9.17 (s, 1H), 8.57 (s, 1H), 8.51-8.54 (m, 1H), 8.23 (s, 1H), 8.15-8.19 (m, 1H), 8.01 (s, 1H), 7.82-7.87 (m, 1H), 7.39-7.44 (m, 1H), 2.77-2.82 (m, 1H), 2.60 (s, 3H), 1.78-2.32 (m, 11H). | 366 |
| 160 | 9.17 (s, 1H), 8.60 (s, 1H), 7.99 (s, 1H), 7.36-7.49 (m, 3H), 7.15-7.22 (m, 1H), 6.18 (s, 1H), 2.73-2.78 (m, 1H), 2.60 (s, 3H), 1.78-2.32(m, 11H). | 383 |
| 161 | 9.17 (s, 1H), 8.60 (s, 1H), 7.99 (s, 1H), 7.36-7.49 (m, 3H), 7.15-7.22 (m, 1H), 6.18 (s, 1H), 2.73-2.78 (m, 1H), 2.60 (s, 3H), 1.78-2.32 (m, 11H), | 383 |
| 162 | 9.39 (d, J = 2.0 Hz, 1H), 8.75 (d, J = 2.5 Hz, 1H), 8.47-8.51 (m, 1H), 7.95 (s, 1H), 7.72 (t, J = 2.0 Hz, 1H), 7.58-7.63 (m, 1H), 7.42-7.50 (m, 1H), 7.32-7.40 (m, 1H), 6.20 (s, 1H), 2.75 (m, 1H), 1.78-2.32 (m, 11H) | 385 |
| 163 | 9.39 (d, J = 2.0 Hz, 1H), 8.75 (d, J = 2.5 Hz, 1H), 8.47-8.51 (m, 1H), 7.95 (s, 1H), 7.72 (t, J = 2.0 Hz, 1H), 7.58-7.63 (m, 1H), 7.42-7.50 (m, 1H), 7.32-7.40 (m, 1H), 6.20 (s, 1H), 2.75 (m, 1H), 1.78-2.32 (m, 11H) | 385 |
| 164 | 9.18 (s, 1H), 8.61 (s, 1H), 8.24 (m, 2H), 8.02 (s, 1H), 7.95 (s, 1H), 7.72-7.69 (m, 1H), 7.04 (s, 1H), 2.61 (s, 3H), 2.58-2.56 (m, 1H), 2.30-2.05 (m, 5H), 1.91-1.73 (m, 6H) | 366 |
| 165 | 9.34 (s, 1H), 9.17 (s, 1H), 8.61 (s, 1H), 8.21 (s, 1H) 8.01 (s, 1H), 7.83 (s, 1H), 2.60-2.54 (m, 4H), 2.45 (s, 3H), 2.30-2.20 (m, 3H), 2.11-2.07 (m, 2H), 1.96-1.73 (m, 6H) | 381 |
| 166 | 9.10 (s, 1H), 8.54 (s, 1H), 8.46 (d, J = 5.5 Hz, 1H), 7.93-7.90 (m, 2H), 7.84 (s, 1H), 2.53-2.50 (m, 7H), 2.18-1.65 (m, 11H) | 381 |
| 167 | 9.17 (s, 1H), 8.79 (m, 1H), 8.61 (s, 1H), 7.97 (s, 1H), 6.52 (d, J = 1.0 Hz, 1H), 2.60-2.57 (m, 4H), 2.34 (s, 3H), 2.28-2.21 (m, 3H), 2.11-2.01 (m, 2H), 1.93-1.75 (m, 5H), 1.73-1.70 (m, 1H) | 386 |

TABLE 3-continued

Analytical data of compounds of formula I

| Example No. | $^1$H NMR (400 or 500 MHz, CDCl$_3$), δ (PPM) | ESI-MS m/z (M + H)$^{+)}$ |
|---|---|---|
| 168 | 9.26 (m, 1H), 9.17 (s, 1H), 8.61 (s, 1H), 7.98 (s, 1H), 7.46 (d, J = 3.5 Hz, 1H), 6.98 (d, J = 3.5 Hz, 1H), 2.61-2.57 (m, 4H), 2.31-2.20 (m, 3H), 2.11-2.04 (m, 2H), 1.92-1.71 (m, 6H) | 372 |
| 169 | 8.33 (s, 1H), 8.00-7.79 (m, 3H), 7.74-7.71 (m, 1H), 7.60-7.57 (m, 1H), 7.28-7.27 (m, 1H), 6.90 (d, J = 7.5 Hz, 1H), 2.58 (m, 4H), 2.43 (s, 3H), 2.24-2.00 (m, 5H), 1.91-1.84 (m, 6H) | 379 |
| 170 | 8.86 (d, J = 7.5 Hz, 1H), 8.21 (s, 1H), 8.02 (d, J = 10.0 Hz, 1H), 7.92-7.88 (m, 2H), 7.58 (m, 1H), 6.89 (d, J = 7.5 Hz, 1H), 2.78 (s, 3H), 2.58-2.55 (m, 1H), 2.43 (s, 3H), 2.24-2.05 (m, 6H), 1.91-1.84 (m, 5H) | 380 |
| 171 | 8.02 (d, J = 7.5 Hz, 1H), 7.86 (s, 1H), 7.58-7.56 (m, 1H), 7.36 (s, 1H), 7.09 (s, 1H), 6.89 (d, J = 7.5 Hz, 1H), 2.56-2.54 (m, 1H), 2.46 (s, 3H), 2.44 (s, 3H), 2.27-2.05 (m, 5H), 1.92-1.84 (m, 6H) | 385 |
| 172 | 8.02 (d, J = 7.5 Hz, 1H), 7.88-7.86 (m, 2H), 7.57-7.64 (m, 2H), 7.42 (s, 1H), 6.89 (d, J = 7.5 Hz, 1H), 2.58-2.57 (m, 1H), 2.43 (s, 3H), 2.24-2.05 (m, 5H), 1.91-1.84 (m, 6H) | 371 |
| 173 | 9.25 (d, J = 7.5 Hz, 1H), 8.36 (s, 1H), 8.03-7.88 (m, 3H), 7.60-7.56 (m, 1H), 6.89 (d, J = 7.5 Hz, 1H), 2.65 (s, 3H), 2.58-2.57 (m, 1H), 2.43 (s, 3H), 2.24-2.05 (m, 5H), 1.91-1.77(m, 6H) | 380 |
| 174 | 9.40 (d, J = 7.5 Hz, 1H), 8.75 (s, 1H), 8.52 (s, 1H), 8.03-7.86 (m, 3H), 7.60-7.56 (m, 1H), 6.89 (d, J = 7.5 Hz, 1H), 2.58 (m, 1H), 2.43 (s, 3H), 2.24-2.05 (m, 5H), 1.91-1.77(m, 6H) | 366 |
| 175 | 8.04-8.03 (m, 2H), 7.61-7.50 (m, 3H), 7.32-7.27 (m, 2H), 6.90 (d, J = 7.5 Hz, 1H), 6.22 (s, 1H), 2.53 (m, 1H), 2.46 (s, 3H), 2.42 (s, 3H), 2.14-1.88 (m, 5H), 1.86-1.72 (m, 6H) | 378 |
| 176 | 8.01 (d, J = 7.5 Hz, 1H), 7.90 (s, 1H), 7.71-7.70 (m, 1H), 7.60-7.57 (m, 2H), 7.46-7.45 (m, 1H), 7.37-7.34 (m, 1H), 6.89 (d, J = 7.0 Hz, 1H), 6.25 (s, 1H), 2.51-2.49 (m, 1H), 2.44 (s, 3H), 2.24-2.00 (m, 5H), 1.89-1.82(m, 6H) | 398 |
| 177 | 8.53 (d, J = 7.5 Hz, 1H), 8.25 (s, 1H), 8.17-8.16 (m, 1H), 8.03-8.01 (m, 1H), 7.92 (s, 1H), 7.84-7.82 (m, 1H), 7.58-7.55 (m, 1H), 7.42-7.40 (m, 1H), 6.88-6.87 (m, 1H), 2.60 (m, 1H), 2.43 (s, 3H), 2.24-2.00 (m, 5H), 1.89-1.76 (m, 6H) | 365 |
| 178 | 8.53 (d, J = 6.0 Hz, 1H), 8.31 (s, 1H), 8.05-7.74 (m, 3H), 7.73 (t, J = 8.0 Hz, 1H), 7.29-7.27 (m, 1H), 2.64-2.57 (m, 7H), 2.27-1.72 (m, 11H) | 380 |
| 179 | 8.87 (d, J = 5.0 Hz, 1H), 8.54 (d, J = 5.5 Hz, 1H), 8.20 (s, 1H), 7.99 (d, J = 5.5 Hz, 1H), 7.89 (d, J = 5.0 Hz, 1H), 2.79 (s, 3H), 2.61 (d, J = 5.0 Hz, 3H), 2.58 (s, 1H), 2.23 (d, J = 6.0 Hz, 3H), 2.08-2.06(m, 2H), 1.93-1.81 (m, 7H) | 381 |
| 180 | 8.54 (d, J = 6.0 Hz, 1H), 7.98 (d, J = 6.0 Hz, 1H), 7.89 (s, 1H), 7.37 (s, 1H), 7.12 (d, J = 1.5 Hz, 1H), 2.62-2.48(m, 7H), 2.25-1.73 (m, 11H) | 386 |
| 181 | 8.53 (d, J = 7.5 Hz, 1H), 8.00-7.95 (m, 2H), 7.56-7.53 (m, 2H), 7.32-7.30 (m, 2H), 6.21 (s, 1H), 2.60 (s, 3H), 2.58 (m, 1H), 2.55 (s, 3H), 2.24-2.05 (m, 5H), 1.91-1.71 (m, 6H) | 379 |
| 182 | 8.53 (d, J = 7.5 Hz, 1H), 7.98-7.95 (m, 2H), 7.71-7.63 (m, 2H), 7.48-7.36 (m, 2H), 6.21 (s, 1H), 2.60 (s, 3H), 2.58 (m, 1H), 2.24-2.05 (m, 5H), 1.91-1.71 (m, 6H) | 399 |
| 183 | 9.31 (s, 1H), 8.32 (s, 1H), 8.22 (s, 1H), 7.98 (d, J = 7.5 Hz, 1H), 7.88 (s, 1H), 7.74-7.71 (m, 1H), 7.28-7.27 (m, 1H), 2.64-2.62 (m, 1H), 2.61 (s, 3H), 2.46 (s, 3H), 2.27-1.75 (m, 11H) | 380 |
| 184 | 9.35 (s, 1H), 8.22 (s, 1H), 7.72 (s, 1H), 7.38 (s, 1H), 7.12 (s, 1H), 2.61-2.58 (m, 1H), 2.48 (s, 3H), 2.47 (s, 3H), 2.25-1.88 (m, 11H) | 386 |
| 185 | 9.35 (s, 1H), 8.23 (s, 1H), 7.79 (s, 1H), 7.72 (s, 1H), 7.61 (d, J = 6.5 Hz, 1H), 7.48 (d, J = 8.0 Hz, 1H), 7.38 (t, J = 8.0 Hz, 1H), 6.18 (s, 1H), 2.57-2.54 (m, 1H), 2.47 (s, 3H), 2.29-1.75 (m, 11H) | 399 |
| 186 | 9.49 (s, 1H), 8.82 (s, 1H), 8.45 (s, 1H), 8.25 (s, 1H), 8.07 (d, J = 8.0 Hz, 1H), 7.89 (s, 1H), 7.80 (d, J = 3.0 Hz, 1H), 7.58 (d, J = 8.0 Hz, 1H), 7.49-7.46 (m, 1H), 7.33-7.32 (m, 1H), 2.26-1.65 (m, 12H) | 384 |
| 187 | 9.57 (s, 1H), 8.35 (s, 1H), 8.24 (s, 1H), 7.89 (s, 1H), 7.55 (s, 1H), 7.51-7.49 (m, 1H), 7.33-7.30 (m, 2H), 6.20 (s, 1H), 2.57-2.55 (m, 1H), 2.39 (s, 3H), 2.31-1.71 (m, 11H) | 385 |

4. Pharmacological Evaluation of Compounds of the Invention

Compounds of the present invention have been tested in vitro and in vivo, and can be tested in vitro and in vivo, in the assays as described below.

In Vitro Assays

Radioligand Binding Assays

Binding assays were performed as described in [J. A. O'Brien et al. Mol. Pharmacol., 2003, 64, 731-740] with slight modifications, including that a radioligand that binds to the methyl-5-(2-pyridinylethynyl)pyridine (MPEP) binding site was used in place of [$^3$H]-MPEP. Briefly, after thawing, the membrane homogenates were resuspended in 50 mM Tris-HCl and 0.9% NaCl binding buffer at pH 7.4 to a final assay concentration of 20 μg is protein/well for radioligand filtration binding. Incubations included 5 nM radioligand, membranes and either buffer or varying concentrations of compound. Samples were incubated for 60 min at room temperature with shaking. Non-specific binding was defined with 10 μM cold MPEP when using the radioligand. After incubation, samples were filtered over a GF/C filter (presoaked in 0.25% polyethyleneimine (PEI)) and then washed 4 times using a Tomtec® Harvester 96® Mach III cell harvester (Tomtec, Hamden, Conn.) with 0.5 mL ice-cold 50 mM Tris- HCl (pH 7.4). IC$_{50}$ values were derived from the inhibition curve and Ki values were calculated according to the Cheng and Prusoff equation of Ki=IC$_{50}$/(1+[L]/Kd) described in [Y. Cheng and W. H. Prusoff Biochem. Pharmacol. 1973, 22, 3099-3108] where [L] is the concentration of radioligand and Kd is its dissociation constant at the receptor, derived from the saturation isotherm. The Ki values of compounds of the invention were <10 µM. The Ki values of representative compounds were listed in Table 4.

Calcium Mobilization Assay to Test for Negative or Positive Allosteric Activity

The cDNA for rat metabotropic glutamate receptor 5 (rmGluR5) and the cDNA for human metabotropic glutamate receptor 5 (rmGluR5) were generous gifts from S. Nakanishi (Kyoto University, Kyoto, Japan). The rmGluR5 or rmGluR5 was stably expressed in a HEK 293 cell line and grown in Dulbecco's Modified Eagle Medium (DMEM) (Invitrogen, Carlsbad, Calif.) with supplements (10% bovine calf serum, 4 mM glutamine, 100 units/mL penicillin, 100 µg/mL streptomycin and 0.75 mM G1418) at 37° C., 5% CO$_2$. Twenty-four hours prior to assay, cells were seeded into 384-well black wall microtiter plates coated with poly-D-lysine. Just prior to assay, media was aspirated and cells dye-loaded (25 µL/well) with 3 µM Fluo-4/0.01% pluronic acid in assay buffer (Hank's Balanced Saline Solution (HBSS)): 150 mM NaCl, 5 mM KCl, 1 mM CaCl$_2$, 1 mM MgCl$_2$, plus 20 mM N-2-Hydroxyethylpiperazine-N'-2-ethanesulfonic acid (HEPES), pH 7.4, 0.1% bovine serum albumin (BSA) and 2.5 mM probenicid) for 1 hour in 5% CO$_2$ at 37° C. After excess dye was discarded, cells were washed in assay buffer and layered with a final volume equal to 30 µL/well. Basal fluorescence is monitored in a fluorometric imaging plate reader (FLIPR) (Molecular Devices, Sunnyvale, Calif.) with an excitation wavelength of 488 nm and an emission range of 500 to 560 nm. Laser excitation energy was adjusted so that basal fluorescence readings were approximately 10,000 relative fluorescent units. Cells were stimulated with an EC$_{20}$ or an EC$_{80}$ concentration of glutamate in the presence of a compound to be tested, both diluted in assay buffer, and relative fluorescent units were measured at defined intervals (exposure=0.6 sec) over a 3 min period at room temperature. Basal readings derived from negative controls were subtracted from all samples. Maximum change in fluorescence was calculated for each well. Concentration-response curves derived from the maximum change in fluorescence were analyzed by non-linear regression (Hill equation). A negative modulator can be identified from these concentration-response curves if a compound produces a concentration dependent inhibition of the EC$_{80}$ glutamate response. Representative Examples were tested in the above assay using hmGluR5, and FLIPR maximum inhibition ranged from about 70% to about 100%, while FLIPR IC$_{50}$ ranged from about 0.32 nM to about 1 µM. The IC$_{50}$ values of representative compounds were listed in Table 4.

A positive modulator (PAM) can be identified from these concentration-response curves if a compound produces a concentration dependent increase in the EC$_{20}$ glutamate response.

A silent allosteric modulator (SAM) can be identified based on results from both the radioligand assay and the calcium mobilization assay. If a compound actively binds to an allosteric site of the receptor based on the radioligand assay, but has no measurable intrinsic efficacy in the calcium mobilization assay, the compound is a SAM.

TABLE 4

In vitro activity of representative compounds

| Example No. | hmGluR5 Ki (nM) | hmGluR5 FLIPR IC$_{50}$ (nM) | hmGlu5 FLIPR % inhibition |
|---|---|---|---|
| 2 | 27 | 3.7 | 89 |
| 6 | 78 | 9 | 92 |
| 15 | 340 | 26 | 88 |
| 36 | 280 | 35 | 87 |
| 126 | 39 | 0.32 | 86 |
| 160 | 35 | 3.9 | 89 |
| 161 | 1200 | 134 | 90 |
| 171 | 65 | 4.7 | 94 |
| 176 | 500 | 33 | 91 |
| 178 | 370 | 38 | 90 |

In Vivo Assays

Compounds of formula (I) can be tested for in vivo anxiolytic effect in a mouse marble burying (mMB) assay similar to that described in [K. Njung'e, K. and S. L. Handley, *Pharmacology Biochemistry and Behavior*, 1991, 38, 63-67].

Anxiolytic effect in vivo can also be tested via a modified Geller-Seifter conflict test described in [N. A. Moore et al. *Behavioural Pharmacology*. 1994, 5, 196-202].

The "Vogel Conflict Test" as described by Vogel et al. [*Psychopharmacologia*, 1971, 21, 1-7] also can be used to detect anxiolytic activity of a compound of formula (I) because anxiolytics increase punished drinking.

Compounds of the invention also can be evaluated in vivo for anxiolytic effects using a light-enhanced startle (LES) reflex method as that described in [Walker and Davis. *Biol. Psychiatry*, 1997, 42, 461-471].

Anxiolytic-like properties also can be evaluated using these additional tests: (1) social interaction described in [S. E. File and P. Seth *European Journal of Pharmacology*, 2003. 463, 35-53], and (2) elevated plus-maze described in [S. M. Korte and S. F. De Boer *European Journal of Pharmacology*, 2003, 463, 163-175].

Compounds of formula (I) can be evaluated in vivo for antidepressive effects. An assessment of depression-like actions can be measured using a forced swim test similar to that described in [J. F. Cryan, et al. *Neuroscience and Biobehavioral Reviews* 2005, 29, 547-569.]

Antidepressive effect also can be evaluated using the Flinders Sensitive Line (FSL) rat in the FST and social interaction test as described in [D. H. Overstreet and G. Griebel *Pharmacol Biochem Behav.*, 2005, 82, 1: 223-227].

Anxiolytic and antidepressive effects also can be evaluated using a paradigm for decreased HPA axis feedback (David et al., 2007, SFN meeting in San Diego). This model based on the chronic delivery of corticosterone in the drinking water, causes anxiety- and depression-like behaviors in mice.

Parkinson's disease (PD) can be assessed by measuring the neurotoxicity of MPTP in rats as described in [E. H. Lee et al. *Chin. J. Physiol.*, 1992, 35, 4: 317-36]. Also, experimentally induced striatal DA depletion in animals is a valid model of Parkinsonism, as described in [W. Schultz *Prog. Neurobiol.*, 1982, 18, 2-3: 121-66]. The capacity of certain substances to damage catecholaminergic neurons has been used extensively to produce DA deficiency in animals, as described in [L. E. Annett et al. *Exp. Neurol.*, 1994, 125, 2: 228-46]. PD can also be assessed by measuring the neurotoxicity induced by 6-hydroxydopamine (6-OHDA) as described in [N. Breysse et al. *J. Neurosci.*, 2002, 22, 13: 5669-5678; D. Rylander et al. *J. Pharmacol. Exp. Ther.*, 2009, 330, 1: 227-235; and L. Chen et al., "Chronic, systemic treatment with a metabotropic glutamate receptor 5 antagonist in 6-hydroxydopamine partially lesioned rats reverses abnormal firing of dopaminergic neurons," *Brain Res.*, 2009, 1286, 192-200].

Fragile X Syndrome can be assessed using the fmrl$^{imlCgr}$ mouse model as described in [Q. J. Yan et al. *Neuropharmacol.*, 2005, 49, 1053-1066], as well as the Fmrl knockout mice with a selective reduction in mGluR5 expression as described in [G. Dölen et al. *Neuron*, 2007, 56, 955-962].

Preclinically, animals also can be evaluated for blockade/attenuation of symptoms associated with schizophrenia. Positive symptoms in animal models of schizophrenia can be evaluated by measuring changes in the overall level of activity of dopamine (DA) activity with concomitant parallel changes in locomotor activity as described in [R. Depoortere et al. *Neuropsychopharmacology*, 2003, 28, 11: 1889-902], D-amphetamine (AMPH) and phencyclidine (PCP) via induction of model psychosis or locomotor hyperactivity as described in [W. J. Freed et al. *Neuropharmacology*, 1984, 23, 2A: 175-81; F. Sams-Dodd *Neuropsychopharmacology*, 1998 19, 1: 18-25]. For example, Depoortere et al., 2003, have described tests for evaluating locomotor activity, catalepsy, climbing and stereotypy, which relate to positive symptomology and side effect profile, by characterizing compounds with typical and atypical antipsychotic efficacy. Attenuation in apomorphine-induced climbing, stereotypy and catalepsy (AIC) can be evaluated as described in [Y. K. Fung et al. *Pharmacol. Biochem. Behav.*, 1986, 24, 1: 139-41 and Y. K. Fung et al. *Steroids*, 1987, 49, 4-5: 287-94]. Additionally, negative symptoms of schizophrenia can be evaluated by measuring social interaction under the influence of NMDA antagonists such as PCP, as described in F. Sams-Dodd, 1998, supra.

Cognitive symptoms of memory, including those from Alzheimer's disease, can be evaluated by such models as the Fear Conditioning Paradigm described in [T. J. Gould et al. *Behav. Pharmacol.*, 2002, 13, 4: 287-94, and A. O. Hamm et al. *Brain*, 2003, 126, Pt 2: 267-75] and the Radial Arm Test described in [J. P. Aggleton et al. *Behav. Brain Res.*, 1996, 19, 2: 133-46], while spatial reference memory and learning can be evaluated in the Morris watermaze test as described in [Morris. *Learn. Motiv.*, 1981, 12, 239-260; B. Bontempi et al. *Eur. J. Neurosci.* 1996, 8, 11: 2348-60].

Additionally, with respect to cognition, memory and hippocampal hypo-functioning can be assessed by measuring the restoration of synaptic plasticity in ovariectomized (OVX) female rats as described in [M. Day and M. Good *Neurobiol. Learn. Mem.*, 2005, 83, 1: 13-21]. Further, changes in attention function because of schizophrenia can be examined by the Five (5) Choice Serial Reaction Time Test (5CSRT) described in [J. L. Muir et al. *Psychopharmacology (Berl)*, 1995, 118, 1: 82-92 and Robbins et al. *Ann. N.Y. Acad. Sci.*, 1998, 846, 222-37].

Human patients can be evaluated for cognitive diseases or disorders by any of the tests within the skill of those in the art.

Analgesic activity can be evaluated by neuropathic pain model (the "Chung model") as described in [Kim and Chung, *Pain*, 1992, 50, 355-363]. Analgesic/anti-inflammatory activity can be evaluated in vivo using the Formalin Paw Test in the mouse such as that described by [Wheeler-Aceto et al, *Psychopharmacology*, 1991, 104, 35-44).

Multiple sclerosis can be evaluated by the experimental autoimmune encephalomyelitis (EAE) model described in [H. Y. Liu et al. *J. Neurosci. Res.*, 2002, 70, 2: 238-48].

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

Each reference cited in the present application, including literature references, books, patents and patent applications, is incorporated herein by reference in its entirety.

What is claimed is:

1. A compound having the formula (I):

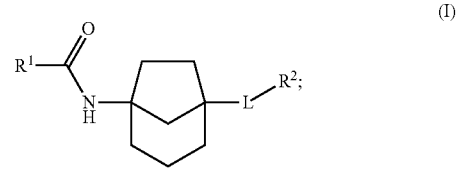

wherein:
L is —NHCO— or —CONH—; and
R$^1$ and R$^2$ are each independently alkyl, cycloalkyl, ketocycloalkyl, heterocyclyl, aryl or heteroaryl, which is optionally mono-, di-, or tri-substituted independently with alkyl, alkoxy, halogen, cyano, nitro, trifluoroalkyl, amino, alkylamino, dialkylamino, acyl, aryl, heteroaryl, heterocyclyl, heterocyclyl-R$^3$, —NHR$^3$, —N(alkyl)R$^3$, —C(O)NHR$^3$, —C(O)N(alkyl)R$^3$, —NHC(O)R$^3$, —N(alkyl)C(O)R$^3$, —OH or —OR$^3$, wherein:
R$^3$ is C$_1$-C$_6$alkyl or C$_1$-C$_6$cycloalkyl, which is optionally substituted with halogen, —CN, —NH$_2$, —NH(C$_1$-C$_3$alkyl), —N(C$_1$-C$_3$alkyl)$_2$, C$_1$-C$_3$alkylheterocyclyl, C$_1$-C$_3$alkylcarbamate, —C(O)NH(C$_1$-C$_3$alkyl), —C(O)N(C$_1$-C$_3$alkyl)$_2$, —NHC(O)—C$_1$-C$_3$alkyl, —N(C$_1$-C$_3$alkyl)-C(O)—C$_1$-C$_3$alkyl, OH, or —O—C$_1$-C$_6$alkyl; or
a pharmaceutically acceptable salt thereof.

2. The compound of claim 1 wherein R$^1$ and R$^2$ are each independently aryl or heteroaryl, which is optionally mono-, di-, or tri-substituted independently with alkyl, alkoxy, halogen, cyano, nitro, trifluoroalkyl, amino, alkylamino, dialkylamino, acyl, —OH or —OR$^3$; and wherein R$^3$ is C$_1$-C$_6$alkyl.

3. The compound of claim 1 or 2 wherein the heteroaryl is selected from the group consisting of optionally mono-, di-, or tri-substituted pyridinyl, pyridazinyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, oxazolyl, 2-quinolinyl, 2-quinazolinyl and 3-phenyl-2-quinolinyl.

4. The compound of claim 1 wherein L is —NHCO—.

5. The compound of claim 1 wherein L is —CONH—.

6. The compound of claim 1, wherein R$^1$ is optionally mono-, di-, or tri-substituted aryl.

7. The compound of claim 1, wherein R$^1$ is selected from the group consisting of optionally mono-, di-, or tri-substituted pyridinyl, pyridazinyl or triazinyl.

8. The compound of claim 1, wherein R$^2$ is optionally mono-, di-, or tri-substituted aryl.

9. The compound of claim 1, wherein R$^2$ is selected from the group consisting of optionally mono-, di-, or tri-substituted pyridinyl, pyridazinyl or triazinyl.

10. The compound of claim 1 selected from the group consisting of:
N,N-bicyclo[3.2.1]octane-1,5-diyl)dipicolinamide;
6-methyl-pyridine-2-carboxylic acid [5-(3-chloro-benzoylamino)-bicyclo[3.2.1]oct-1-yl]-amide;
N,N-bicyclo[3.2.1]octane-1,5-diyl)bis(6-methylpicolinamide);

6-methyl-pyrazine-2-carboxylic acid {5-[(pyridine-2-carbonyl)-amino]-bicyclo[3.2.1]oct-1-yl}-amide;
N,N-(bicyclo[3.2.1]octane-1,5-diyl)bis(6-methylpyrazine-2-carboxamide);
6-methyl-pyrazine-2-carboxylic acid [5-(3-fluoro-benzoylamino)-bicyclo[3.2.1]oct-1-yl]-amide;
6-methyl-pyrazine-2-carboxylic acid [5-(4-fluoro-benzoylamino)-bicyclo[3.2.1]oct-1-yl]-amide;
2-methyl-pyrimidine-4-carboxylic acid {5-[(6-methyl-pyrazine-2-carbonyl)-amino]-bicyclo[3.2.1]oct-1-yl}-amide;
N-(5-(3-chlorobenzamido)bicyclo[3.2.1]octan-1-yl)-4-methylpyrimidine-2-carboxamide;
N-(5-(3-chlorobenzamido)bicyclo[3.2.1]octan-1-yl)pyrimidine-2-carboxamide;
N-(5-(3-chlorobenzamido)bicyclo[3.2.1]octan-1-yl)pyrimidine-4-carboxamide;
N-(5-(3-chlorobenzamido)bicyclo[3.2.1]octan-1-yl)thiazole-2-carboxamide;
N-(5-(3-chlorobenzamido)bicyclo[3.2.1]octan-1-yl)-2-methylpyrimidine-4-carboxamide;
N-(5-(3-chlorobenzamido)bicyclo[3.2.1]octan-1-yl)-4-methylthiazole-2-carboxamide;
N-(5-(3-chlorobenzamido)bicyclo[3.2.1]octan-1-yl)-2-methylthiazole-5-carboxamide;
N-(5-(3-chlorobenzamido)bicyclo[3.2.1]octan-1-yl)-5-fluoropicolinamide;
N-(5-(3-chlorobenzamido)bicyclo[3.2.1]octan-1-yl)-5-methylpicolinamide;
N-(5-(3-chlorobenzamido)bicyclo[3.2.1]octan-1-yl)-4-methylpicolinamide;
N-(5-(3-chlorobenzamido)bicyclo[3.2.1]octan-1-yl)-5-methylnicotinamide;
N-(5-(3-fluorobenzamido)bicyclo[3.2.1]octan-1-yl)pyrazine-2-carboxamide;
N-(5-(3-fluorobenzamido)bicyclo[3.2.1]octan-1-yl)picolinamide;
N-(5-(3-fluorobenzamido)bicyclo[3.2.1]octan-1-yl)isonicotinamide;
N-(5-(3-fluorobenzamido)bicyclo[3.2.1]octan-1-yl)-5-methylpicolinamide;
N-(5-(3-fluorobenzamido)bicyclo[3.2.1]octan-1-yl)-6-methylpicolinamide;
N-(5-(3-fluorobenzamido)bicyclo[3.2.1]octan-1-yl)-2-methylpyrimidine-4-carboxamide;
N-(5-(3-fluorobenzamido)bicyclo[3.2.1]octan-1-yl)nicotinamide;
N-(5-{(3-fluorobenzoyl)amino]bicyclo[3.2.1]oct-1-yl}pyrimidine-2-carboxamide;
N-(5-(3-fluorobenzamido)bicyclo[3.2.1]octan-1-yl)-4-methylpyrimidine-2-carboxamide;
N-(5-(3-fluorobenzamido)bicyclo[3.2.1]octan-1-yl)-4-methylthiazole-2-carboxamide;
N-(5-(3-fluorobenzamido)bicyclo[3.2.1]octan-1-yl)-2-methylthiazole-5-carboxamide;
N-(5-(3-fluorobenzamido)bicyclo[3.2.1]octan-1-yl)-4-methylpicolinamide;
N-(5-(3-fluorobenzamido)bicyclo[3.2.1]octan-1-yl)-5-methylnicotinamide;
N-(5-(3-fluorobenzamido)bicyclo[3.2.1]octan-1-yl)pyrimidine-4-carboxamide;
N-(5-(3-fluorobenzamido)bicyclo[3.2.1]octan-1-yl)thiazole-2-carboxamide;
N-(5-(3-methylbenzamido)bicyclo[3.2.1]octan-1-yl)nicotinamide;
N-(5-(3-methylbenzamido)bicyclo[3.2.1]octan-1-yl)isonicotinamide;
6-methyl-N-(5-(3-methylbenzamido)bicyclo[3.2.1]octan-1-yl)pyrazine-2-carboxamide;
4-methyl-N-(5-(3-methylbenzamido)bicyclo[3.2.1]octan-1-yl)pyrimidine-2-carboxamide;
5-methyl-N-(5-(3-methylbenzamido)bicyclo[3.2.1]octan-1-yl)nicotinamide;
N-(5-(3-methylbenzamido)bicyclo[3.2.1]octan-1-yl)pyrimidine-2-carboxamide;
N-(5-(3-methylbenzamido)bicyclo[3.2.1]octan-1-yl)pyrimidine-4-carboxamide;
N-(5-(3-methylbenzamido)bicyclo[3.2.1]octan-1-yl)thiazole-2-carboxamide;
2-methyl-N-(5-(3-methylbenzamido)bicyclo[3.2.1]octan-1-yl)pyrimidine-4-carboxamide;
4-methyl-N-(5-(3-methylbenzamido)bicyclo[3.2.1]octan-1-yl)thiazole-2-carboxamide;
2-methyl-N-(5-(3-methylbenzamido)bicyclo[3.2.1]octan-1-yl)thiazole-5-carboxamide;
5-fluoro-N-(5-(3-methylbenzamido)bicyclo[3.2.1]octan-1-yl)picolinamide;
5-methyl-N-(5-(3-methylbenzamido)bicyclo[3.2.1]octan-1-yl)picolinamide;
4-methyl-N-(5-(3-methylbenzamido)bicyclo[3.2.1]octan-1-yl)picolinamide;
N-(5-(5-fluoropicolinamido)bicyclo[3.2.1]octan-1-yl)-2-methylpyrimidine-4-carboxamide; and
5-fluoro-N-(5-(6-methylpicolinamido)bicyclo[3.2.1]octan-1-yl)picolinamide; or a pharmaceutically acceptable salt thereof.

11. The compound of claim 1 selected from the group consisting of:
N-(5-(5-fluoropicolinamido)bicyclo[3.2.1]octan-1-yl)-6-methylpyrazine-2-carboxamide;
5-methyl-N-(5-(6-methylpyrazine-2-carboxamido)bicyclo[3.2.1]octan-1-yl)pyrazine-2-carboxamide;
5-methyl-N-(5-(3-methylbenzamido)bicyclo[3.2.1]octan-1-yl)pyrazine-2-carboxamide;
N-(5-(3-fluorobenzamido)bicyclo[3.2.1]octan-1-yl)-5-methylpyrazine-2-carboxamide;
N-(5-(3-chlorobenzamido)bicyclo[3.2.1]octan-1-yl)-5-methylpyrazine-2-carboxamide;
N-(5-{(5-methylpyrazin-2-yl)carbonyl)amino)}bicyclo[3.2.1]oct-1-yl)pyrimidine-4-carboxamide;
N-(5-(5-methylpyrazine-2-carboxamido)bicyclo[3.2.1]octan-1-yl)thiazole-2-carboxamide;
N-(5-benzamidobicyclo[3.2.1]octan-1-yl)-5-methylpyrazine-2-carboxamide;
4-methyl-N-(5-(5-methylpyrazine-2-carboxamido)bicyclo[3.2.1]octan-1-yl)pyrimidine-2-carboxamide;
2-methyl-N-(5-(5-methylpyrazine-2-carboxamido)bicyclo[3.2.1]octan-1-yl)pyrimidine-4-carboxamide;
5-methyl-N-(5-{[(4-methyl-1,3-thiazol-2-yl)carbonyl]amino}bicyclo[3.2.1]oct-1-yl)pyrazine-2-carboxamide;
N-(5-{[(5-fluoropyridin-2-yl)carbonyl]amino}bicyclo[3.2.1]oct-1-yl)-5-methylpyrazine-2-carboxamide;
5-methyl-N-(5-(5-methylpicolinamido)bicyclo[3.2.1]octan-1-yl)pyrazine-2-carboxamide;
5-methyl-N-(5-(4-methylpicolinamido)bicyclo[3.2.1]octan-1-yl)pyrazine-2-carboxamide;
N-(5-(3-fluoro-6-methylpicolinamido)bicyclo[3.2.1]octan-1-yl)-6-methylpyrazine-2-carboxamide;
N-(5-(2-fluorobenzamido)bicyclo[3.2.1]octan-1-yl)-6-methylpyrazine-2-carboxamide;
N-(5-(3,5-difluorobenzamido)bicyclo[3.2.1]octan-1-yl)-6-methylpyrazine-2-carboxamide;

6-methyl-N-(5-(nicotinamido)bicyclo[3.2.1]octan-1-yl) pyrazine-2-carboxamide;
N-(5-(3-chlorobenzamido)bicyclo[3.2.1]octan-1-yl)-6-methylpyrazine-2-carboxamide;
4-methyl-N-(5-(6-methylpyrazine-2-carboxamido)bicyclo[3.2.1]octan-1-yl)pyrimidine-2-carboxamide;
N-(5-(6-methylpyrazine-2-carboxamido)bicyclo[3.2.1]octan-1-yl)pyrimidine-4-carboxamide;
N-(5-(6-methylpyrazine-2-carboxamido)bicyclo[3.2.1]octan-1-yl)thiazole-2-carboxamide;
N-(5-benzamidobicyclo[3.2.1]octan-1-yl)-6-methylpyrazine-2-carboxamide;
4-methyl-N-(5-(6-methylpyrazine-2-carboxamido)bicyclo[3.2.1]octan-1-yl)thiazole-2-carboxamide;
6-methyl-N-(5-(5-methylpicolinamido)bicyclo[3.2.1]octan-1-yl)pyrazine-2-carboxamide;
6-methyl-N-(5-(4-methylpicolinamido)bicyclo[3.2.1]octan-1-yl)pyrazine-2-carboxamide;
6-methyl-N-(5-(5-methylnicotinamido)bicyclo[3.2.1]octan-1-yl)pyrazine-2-carboxamide;
6-methyl-N-(5-(pyrazine-2-carboxamido)bicyclo[3.2.1]octan-1-yl)pyrazine-2-carboxamide;
N-(5-(6-methylpyrazine-2-carboxamido)bicyclo[3.2.1]octan-1-yl)pyrimidine-2-carboxamide;
6-methyl-N-(5-(6-methylpicolinamido)bicyclo[3.2.1]octan-1-yl)pyrazine-2-carboxamide;
6-methyl-N-(5-(5-methylnicotinamido)bicyclo[3.2.1]octan-1-yl)picolinamide;
6-methyl-N-(5-(3-methylbenzamido)bicyclo[3.2.1]octan-1-yl)picolinamide;
N-(5-(6-methylpicolinamido)bicyclo[3.2.1]octan-1-yl) pyrazine-2-carboxamide;
N-(5-(6-methylpicolinamido)bicyclo[3.2.1]octan-1-yl) pyrimidine-2-carboxamide;
N-(5-(6-methylpicolinamido)bicyclo[3.2.1]octan-1-yl) pyrimidine-4-carboxamide;
N-(5-(6-methylpicolinamido)bicyclo[3.2.1]octan-1-yl) thiazole-2-carboxamide;
N-(5-benzamidobicyclo[3.2.1]octan-1-yl)-6-methylpicolinamide;
5-methyl-N-(5-(6-methylpicolinamido)bicyclo[3.2.1]octan-1-yl)pyrazine-2-carboxamide;
4-methyl-N-(5-(6-methylpicolinamido)bicyclo[3.2.1]octan-1-yl)pyrimidine-2-carboxamide;
2-methyl-N-(5-(6-methylpicolinamido)bicyclo[3.2.1]octan-1-yl)pyrimidine-4-carboxamide;
2-methyl-N-(5-(6-methylpicolinamido)bicyclo[3.2.1]octan-1-yl)thiazole-5-carboxamide;
6-methyl-N-(5-(5-methylpicolinamido)bicyclo[3.2.1]octan-1-yl)picolinamide;
6-methyl-N-(5-(4-methylpicolinamido)bicyclo[3.2.1]octan-1-yl)picolinamide;
N-(5-(3-fluoro-6-methylpicolinamido)bicyclo[3.2.1]octan-1-yl)pyrazine-2-carboxamide;
pyrazine-2-carboxylic acid [5-(3-trifluoromethyl-benzoylamino)-bicyclo[3.2.1]oct-1-yl]-amide;
pyrazine-2-carboxylic acid [5-(3-cyano-benzoylamino)-bicyclo[3.2.1]oct-1-yl]-amide;
pyrazine-2-carboxylic acid {5-(3-fluoro-pyridine-2-carbonyl]-amino]-bicyclo[3.2.1]oct-1-yl}-amide;
N-(5-(3-methylbenzamido)bicyclo[3.2.1]octan-1-yl) pyrazine-2-carboxamide;
N-(5-(3-chlorobenzamido)bicyclo[3.2.1]octan-1-yl)pyrazine-2-carboxamide; and
2-methyl-N-(5-(pyrazine-2-carboxamido)bicyclo[3.2.1]octan-1-yl)pyrimidine-4-carboxamide; or a pharmaceutically acceptable salt thereof.

12. The compound of claim 1 selected from the group consisting of:
4-methyl-N-(5-(pyrazine-2-carboxamido)bicyclo[3.2.1]octan-1-yl)thiazole-2-carboxamide;
N-(5-(5-fluoropicolinamido)bicyclo[3.2.1]octan-1-yl) pyrazine-2-carboxamide;
N-(5-(4-methylpicolinamido)bicyclo[3.2.1]octan-1-yl) pyrazine-2-carboxamide;
2-methyl-N-(5-(picolinamido)bicyclo[3.2.1]octan-1-yl) pyrimidine-4-carboxamide;
6-methyl-N-(5-(picolinamido)bicyclo[3.2.1]octan-1-yl) picolinamide;
5-methyl-N-(5-(picolinamido)bicyclo[3.2.1]octan-1-yl) pyrazine-2-carboxamide;
4-methyl-N-(5-(picolinamido)bicyclo[3.2.1]octan-1-yl) pyrimidine-2-carboxamide;
4-methyl-N-(5-(picolinamido)bicyclo[3.2.1]octan-1-yl) thiazole-2-carboxamide;
2-methyl-N-(5-(picolinamido)bicyclo[3.2.1]octan-1-yl) thiazole-5-carboxamide;
5-fluoro-N-(5-(picolinamido)bicyclo[3.2.1]octan-1-yl)picolinamide;
5-methyl-N-(5-(picolinamido)bicyclo[3.2.1]octan-1-yl) picolinamide;
4-methyl-N-(5-(picolinamido)bicyclo[3.2.1]octan-1-yl) picolinamide;
N-(5-(5-methylnicotinamido)bicyclo[3.2.1]octan-1-yl)picolinamide;
N-(5-(3-methylbenzamido)bicyclo[3.2.1]octan-1-yl)picolinamide;
N-(5-(3-chlorobenzamido)bicyclo[3.2.1]octan-1-yl)picolinamide;
3-fluoro-6-methyl-pyridine-2-carboxylic acid {(1S,5R)-5-[(6-methyl-pyridine-2-carbonyl)-amino]-bicyclo[3.2.1]oct-1-yl}-amide;
6-methyl-pyridine-2-carboxylic acid [(1R,5S)-5-(3-fluoro-benzoylamino)-bicyclo[3.2.1]oct-1-yl]-amide;
6-methyl-pyridine-2-carboxylic acid [(1R,5S)-5-(3-methyl-benzoylamino)-bicyclo[3.2.1]oct-1-yl]-amide;
6-methyl-pyridine-2-carboxylic acid {(1R,5S)-5-[(pyridine-2-carbonyl)-amino]-bicyclo[3.2.1]oct-1-yl}-amide;
2-methyl-pyrimidine-4-carboxylic acid {(1S,5R)-5-[(6-methyl-pyridine-2-carbonyl)-amino]-bicyclo[3.2.1]oct-1-yl}-amide;
pyrimidine-4-carboxylic acid {(1S,5R)-5-[(6-methyl-pyridine-2-carbonyl)-amino]-bicyclo[3.2.1]oct-1-yl}-amide;
6-methyl-pyridine-2-carboxylic acid ((1S,5R)-5-benzoylamino-bicyclo[3.2.1]oct-1-yl)-amide;
3-fluoro-6-methyl-pyridine-2-carboxylic acid {(1R,5S)-5-[(6-methyl-pyridine-2-carbonyl)-amino]-bicyclo[3.2.1]oct-1-yl}-amide;
2-methyl-pyrimidine-4-carboxylic acid {(1R,5S)-5-[(6-methyl-pyridine-2-carbonyl)-amino]-bicyclo[3.2.1]oct-1-yl}-amide
6-methyl-pyridine-2-carboxylic acid [(1S,5R)-5-(3-fluoro-benzoylamino)-bicyclo[3.2.1]oct-1-yl]-amide
6-methyl-pyridine-2-carboxylic acid {(1S,5R)-5-[(pyridine-2-carbonyl)-amino]-bicyclo[3.2.1]oct-1-yl}-amide
pyrimidine-4-carboxylic acid {(1R,5S)-5-[(6-methyl-pyridine-2-carbonyl)-amino]-bicyclo[3.2.1]oct-1-yl}-amide;
5-fluoro-N-((1R,5S)-5-(6-methylpicolinamido)bicyclo[3.2.1]octan-1-yl)picolinamide;

6-methyl-pyridine-2-carboxylic acid {(1S,5R)-5-[(thiazole-2-carbonyl)-amino]-bicyclo[3.2.1]oct-1-yl}-amide;
6-methyl-N-((1R,5S)-5-(4-methylpicolinamido)bicyclo[3.2.1]octan-1-yl)picolinamide;
5-methoxy-N-((1R,5S)-5-(6-methylpicolinamido)bicyclo[3.2.1]octan-1-yl)picolinamide;
6-methyl-pyrazine-2-carboxylic acid {(1S,5R)-5-[(6-methyl-pyridine-2-carbonyl)-amino]-bicyclo[3.2.1]oct-1-yl}-amide;
6-methyl-pyrazine-2-carboxylic acid {(1S,5R)-5-[(4-methyl-thiazole-2-carbonyl)-amino]-bicyclo[3.2.1]oct-1-yl}-amide;
6-methyl-pyrazine-2-carboxylic acid [(1S,5R)-5-(3-methyl-benzoylamino)-bicyclo[3.2.1]oct-1-yl]-amide;
6-methyl-pyrazine-2-carboxylic acid {(1S,5R)-5-[(3-fluoro-pyridine-2-carbonyl)-amino]-bicyclo[3.2.1]oct-1-yl}-amide;
6-methyl-pyrazine-2-carboxylic acid [(1R,5S)-5-(3,5-difluoro-benzoylamino)-bicyclo[3.2.1]oct-1-yl]-amide;
6-methyl-pyrazine-2-carboxylic acid {(1R,5S)-5-[(6-methyl-pyridine-2-carbonyl)-amino]-bicyclo[3.2.1]oct-1-yl}-amide;
6-methyl-pyrazine-2-carboxylic acid {(1R,5S)-5-[(4-methyl-thiazole-2-carbonyl)-amino]-bicyclo[3.2.1]oct-1-yl}-amide;
6-methyl-pyrazine-2-carboxylic acid [(1R,5S)-5-(3-methyl-benzoylamino)-bicyclo[3.2.1]oct-1-yl]-amide;
6-methyl-pyrazine-2-carboxylic acid {(1R,5S)-5-[(3-fluoro-pyridine-2-carbonyl)-amino]-bicyclo[3.2.1]oct-1-yl}-amide;
pyridine-2-carboxylic acid [(1S,5R)-5-(3-methyl-benzoylamino)-bicyclo[3.2.1]oct-1-yl]-amide;
pyridine-2-carboxylic acid [(1S,5R)-5-(3-fluoro-benzoylamino)-bicyclo[3.2.1]oct-1-yl]-amide;
pyridine-2-carboxylic acid {(1S,5R)-5-[(4-methyl-thiazole-2-carbonyl)-amino]-bicyclo[3.2.1]oct-1-yl}-amide;
2-methyl-pyrimidine-4-carboxylic acid {(1R,5S)-5-[(pyridine-2-carbonyl)-amino]-bicyclo[3.2.1]oct-1-yl}-amide;
5-fluoro-pyridine-2-carboxylic acid {(1R,5S)-5-[(pyridine-2-carbonyl)-amino]-bicyclo[3.2.1]oct-1-yl}-amide;
6-fluoro-pyridine-2-carboxylic acid {(1R,5S)-5-[(pyridine-2-carbonyl)-amino]-bicyclo[3.2.1]oct-1-yl}-amide;
3-fluoro-6-methyl-pyridine-2-carboxylic acid {(1R,5S)-5-[(pyridine-2-carbonyl)-amino]-bicyclo[3.2.1]oct-1-yl}-amide;
pyridine-2-carboxylic acid [(1S,5R)-5-(3-trifluoromethyl-benzoylamino)-bicyclo[3.2.1]oct-1-yl]-amide;
pyridine-2-carboxylic acid [(1S,5R)-5-(3-cyano-benzoylamino)-bicyclo[3.2.1]oct-1-yl]-amide; and
pyridine-2-carboxylic acid [(1S,5R)-5-(3-cyano-5-fluoro-benzoylamino)-bicyclo[3.2.1]oct-1-yl]-amide; or a pharmaceutically acceptable salt thereof.

13. The compound of claim 1 selected from the group consisting of:
6-methyl-pyrazine-2-carboxylic acid [(1S,5R)-5-(2,5-difluoro-benzoylamino)-bicyclo[3.2.1]oct-1-yl]-amide;
6-methyl-pyrazine-2-carboxylic acid {(1S,5R)-5-[(6-fluoro-pyridine-2-carbonyl)-amino]-bicyclo[3.2.1]oct-1-yl}-amide;
6-methyl-pyrazine-2-carboxylic acid [(1S,5R)-5-(3-cyano-5-fluoro-benzoylamino)-bicyclo[3.2.1]oct-1-yl]-amide;
6-methyl-pyrazine-2-carboxylic acid {(1S,5R)-5-[(5-fluoro-pyridine-2-carbonyl)-amino]-bicyclo[3.2.1]oct-1-yl}-amide
6-methyl-pyrazine-2-carboxylic acid {(1S,5R)-5-[(3,5-difluoro-pyridine-2-carbonyl)-amino]-bicyclo[3.2.1]oct-1-yl}-amide;
2-methyl-pyrimidine-4-carboxylic acid {(1S,5R)-5-[(6-methyl-pyrazine-2-carbonyl)-amino]-bicyclo[3.2.1]oct-1-yl}-amide;
2-methyl-pyrimidine-4-carboxylic acid {(1R,5S)-5-[(6-methyl-pyrazine-2-carbonyl)-amino]-bicyclo[3.2.1]oct-1-yl}-amide;
6-methyl-pyrazine-2-carboxylic acid {(1R,5S)-5-[(pyridine-2-carbonyl)-amino]-bicyclo[3.2.1]oct-1-yl}-amide;
6-methyl-pyrazine-2-carboxylic acid {(1S,5R)-5-[(pyridine-2-carbonyl)-amino]-bicyclo[3.2.1]oct-1-yl}-amide;
6-methyl-pyrazine-2-carboxylic acid [(1R,5S)-5-(3-fluoro-benzoylamino)-bicyclo[3.2.1]oct-1-yl]-amide;
6-methyl-pyrazine-2-carboxylic acid [(1S,5R)-5-(3-fluoro-benzoylamino)-bicyclo[3.2.1]oct-1-yl]-amide;
6-methyl-pyrazine-2-carboxylic acid [(1R,5S)-5-(3-fluoro-benzoylamino)-bicyclo[3.2.1]oct-1-yl]-amide;
pyrazine-2-carboxylic acid [(1S,5R)-5-(3-chloro-benzoylamino)-bicyclo[3.2.1]oct-1-yl]-amide;
pyrazine-2-carboxylic acid [(1R,5S)-5-(3-chloro-benzoylamino)-bicyclo[3.2.1]oct-1-yl]-amide;
6-methyl-N-(5-(pyridin-2-ylcarbamnoyl)bicyclo[3.2.1]octan-1-yl)pyrazine-2-carboxamide;
6-methyl-N-(5-(6-methylpyrazin-2-ylcarbamoyl)bicyclo[3.2.1]octan-1-yl)pyrazine-2-carboxamide;
6-methyl-N-(5-(2-methylpyrimidin-4-ylcarbamoyl)bicyclo[3.2.1]octan-1-yl)pyrazine-2-carboxamide;
6-methyl-N-(5-(4-methylthiazol-2-ylcarbamoyl)bicyclo[3.2.1]octan-1-yl)pyrazine-2-carboxamide;
6-methyl-N-(5-(thiazol-2-ylcarbamioyl)bicyclo[3.2.1]octan-1-yl)pyrazine-2-carboxamide;
6-methyl-N-(5-(6-methylpyridin-2-ylcarbamoyl)bicyclo[3.2.1]octan-1-yl)picolinamide;
2-methyl-N-(5-(6-methylpyridin-2-ylcarbamioyl)bicyclo[3.2.1]octan-1-yl)pyrimidine-4-carboxamide;
4-methyl-N-(5-(6-methylpyridin-2-ylcarbamoyl)bicyclo[3.2.1]octan-1-yl)thiazole-2-carboxamide;
N-(5-(6-methylpyridin-2-ylcarbamoyl)bicyclo[3.2.1]octan-1-yl)thiazole-2-carboxamide;
5-methyl-N-(5-(6-methylpyridin-2-ylcarbamioyl)bicyclo[3.2.1]octan-1-yl)pyrazine-2-carboxamide;
N-(5-(6-methylpyridin-2-ylcarbamoyl)bicyclo[3.2.1]octan-1-yl)pyrazine-2-carboxamide;
5-(3-methylbenzamido)-N-(6-methylpyridin-2-yl)bicyclo[3.2.1]octane-1-carboxamide;
5-(3-chlorobenzamido)-N-(6-methylpyridin-2-yl)bicyclo[3.2.1]octane-1-carboxamide;
N-(5-(6-methylpyridin-2-ylcarbamoyl)bicyclo[3.2.1]octan-1-yl)picolinamide;
6-methyl-N-(5-(2-methylpyrimidin-4-ylcarbamoyl)bicyclo[3.2.1]octan-1-yl)picolinamide;
2-methyl-N-(5-(2-methylpyrimidin-4-ylcarbamoyl)bicyclo[3.2.1]octan-1-yl)pyrimidine-4-carboxamide;
4-methyl-N-(5-(2-methylpyrimidin-4-ylcarbamoyl)bicyclo[3.2.1]octan-1-yl)thiazole-2-carboxamide;
5-(3-methylbenzamido)-N-(2-methylpyrimidin-4-yl)bicyclo[3.2.1]octane-1-carboxamide;
5-(3-chlorobenzamido)-N-(2-methylpyrimidin-4-yl)bicyclo[3.2.1]octane-1-carboxamide;

6-methyl-N-(5-(6-methylpyrazin-2-ylcarbamoyl)bicyclo[3.2.1]octan-1-yl)picolinamide,
4-methyl-N-(5-(6-methylpyrazin-2-ylcarbamoyl)bicyclo[3.2.1]octan-1-yl)thiazole-2-carboxamide;
5-(3-chlorobenzamido)-N-(6-methylpyrazin-2-yl)bicyclo[3.2.1]octane-1-carboxamide;
5-(3-chlorobenzamido)-N-(pyridin-3-yl)bicyclo[3.2.1]octane-1-carboxamide; and
5-(3-chlorobenzamido)-N-(pyrazin-2-yl)bicyclo[3.2.1]octane-1-carboxamide; or a pharmaceutically acceptable salt thereof.

14. A pharmaceutical composition comprising a compound of claim 1 and a pharmaceutically acceptable carrier.

15. The compound of claim 1, wherein the compound is selected from the group consisting of N-(5-(3-fluorobenzamido)bicyclo[3.2.1]octan-1-yl)-5-methylnicotinamide; N-(5-(3-methylbenzamido)bicyclo[3.2.1]octan-1-yl)nicotinamide; 6-methyl-pyridine-2-carboxylic acid [(1R,5S)-5-(3-fluoro-benzoylamino)-bicyclo[3.2.1]oct-1-yl]-amide; 6-methyl-pyridine-2-carboxylic acid [(1R,5S)-5-(3-methyl-benzoylamino)-bicyclo[3.2.1]oct-1-yl]-amide; 3-fluoro-6-methyl-pyridine-2-carboxylic acid {(1R,5S)-5-[(6-methyl-pyridine-2-carbonyl)-amino]-bicyclo[3.2.1]oct-1-yl}-amide; 6-methyl-pyrazine-2-carboxylic acid [(1R,5S)-5-(3,5-difluoro-benzoylamino)-bicyclo[3.2.1]oct-1-yl]-amide; 6-methyl-pyrazine-2-carboxylic acid {(1S,5R)-5-[(3-fluoro-pyridine-2-carbonyl)-amino]-bicyclo[3.2.1]oct-1-yl}-amide; 6-methyl-pyrazine-2-carboxylic acid {(1S,5R)-5-[(6-methyl-pyridine-2-carbonyl)-amino]-bicyclo[3.2.1]oct-1-yl}-amide; 6-fluoro-pyridine-2-carboxylic acid {(1R,5S)-5-[(pyridine-2-carbonyl)-amino]-bicyclo[3.2.1]oct-1-yl}-amide; and 6-methyl-pyrazine-2-carboxylic acid [(1S,5R)-5-(3-fluoro-benzoylamino)-bicyclo[3.2.1]oct-1-yl]-amide; or a pharmaceutically acceptable salt thereof.

16. The compound of claim 1, wherein the compound is selected from the group consisting of N,N-bicyclo[3.2.1]octane-1,5-diyl)dipicolinamide; N,N-(bicyclo[3.2.1]octane-1,5-diyl)bis(6-methylpyrazine-2-carboxamide; N-(5-(3-fluorobenzamido)bicyclo[3.2.1]octan-1-yl)isonicotinamide; N-(5-[(3-fluorobenzoyl)amino]bicyclo[3.2.1]oct-1-yl}pyrimidine-2-carboxamide; 6-methyl-pyridine-2-carboxylic acid {(1R,5S)-5-[(pyridine-2-carbonyl)-amino]-bicyclo[3.2.1]oct-1-yl}-amide; 5-fluoro-N-((1R,5S)-5-(6-methylpicolinamido)bicyclo[3.2.1]octan-1-yl)picolinamide; 6-methyl-pyrazine-2-carboxylic acid {(1R,5S)-5-[(3-fluoro-pyridine-2-carbonyl)-amino]-bicyclo[3.2.1]oct-1-yl}-amide; pyridine-2-carboxylic acid [(1S,5R)-5-(3-fluoro-benzoylamino)-bicyclo[3.2.1]oct-1-yl]-amide; pyridine-2-carboxylic acid [(1S,5R)-5-(3-trifluoromethyl-benzoylamino)-bicyclo[3.2.1]oct-1-yl]-amide; and 6-methyl-pyrazine-2-carboxylic acid [(1R,5S)-5-(3-fluoro-benzoylamino)-bicyclo[3.2.1]oct-1-yl]-amide; or a pharmaceutically acceptable salt thereof.

\* \* \* \* \*